(12) United States Patent
Amirouche et al.

(10) Patent No.: US 8,663,538 B2
(45) Date of Patent: Mar. 4, 2014

(54) METHOD OF MAKING A MEMBRANE FOR USE WITH A FLOW CONTROL SYSTEM FOR A MICROPUMP

(75) Inventors: Farid Amirouche, Highland Park, IL (US); Matthew Cantwell, Northbrook, IL (US)

(73) Assignee: Picolife Technologies, LLC, Deerfield, IL (US)

( * ) Notice: Subject to any disclaimer, the term of this patent is extended or adjusted under 35 U.S.C. 154(b) by 245 days.

(21) Appl. No.: 13/174,643

(22) Filed: Jun. 30, 2011

(65) Prior Publication Data

US 2011/0309552 A1   Dec. 22, 2011

Related U.S. Application Data

(63) Continuation-in-part of application No. PCT/US2009/059020, filed on Sep. 30, 2009.

(60) Provisional application No. 61/152,165, filed on Feb. 12, 2009, provisional application No. 61/448,050, filed on Mar. 1, 2011.

(51) Int. Cl.
*B29C 43/38* (2006.01)
(52) U.S. Cl.
USPC .................................................. 264/331.11
(58) Field of Classification Search
CPC ........................................................ B29C 43/38
USPC ..................................................... 264/331.11
See application file for complete search history.

(56) References Cited

U.S. PATENT DOCUMENTS

| | | | |
|---|---|---|---|
| 2,398,435 | A | 4/1946 | Marks |
| 3,137,242 | A | 6/1964 | Hahn |
| 3,498,228 | A | 3/1970 | Blumle et al. |

(Continued)

FOREIGN PATENT DOCUMENTS

| | | |
|---|---|---|
| EP | 0 024 431 B1 | 8/1985 |
| EP | 0 299 628 A1 | 1/1989 |

(Continued)

OTHER PUBLICATIONS

"Sylgard 184", Dow Corning, 2007, accessed at http://ncnc.engineering.ucdavis.edu/pages/equipment/Sylgard_184_data_sheet.pdf.*

(Continued)

*Primary Examiner* — Yogendra Gupta
*Assistant Examiner* — Alison Hinenlang
(74) *Attorney, Agent, or Firm* — Finnegan, Henderson, Farabow, Garrett & Dunner, LLP

(57) ABSTRACT

A method of making a membrane for use with a flow control system is disclosed. A female mold body portion and a male mold body portion are provided. A body portion support member configured to receive at least a portion of the female body portion and at least a portion of the male body portion is provided. The female and male body portions are separated from one another Membrane manufacturing material is provided to a concave portion of the female mold body portion. The sleeve is moved downward. The lower mold portion is lowered until it is just short of its final intended position. Excess membrane manufacturing material, if any, is removed from around the seam of the mold. The upper mold portion is lowered the remaining distance so that the two mold portions are separated by the exact distance desired for the final membrane thickness.

21 Claims, 27 Drawing Sheets

(56) References Cited

U.S. PATENT DOCUMENTS

| | | | |
|---|---|---|---|
| 3,691,263 A | 9/1972 | Stoy et al. | |
| 3,771,694 A | 11/1973 | Kaminski | |
| 3,827,565 A | 8/1974 | Matsumura | |
| 3,889,710 A | 6/1975 | Brost | |
| 3,915,609 A | 10/1975 | Robinson | |
| 4,017,238 A | 4/1977 | Robinson | |
| 4,197,266 A | 4/1980 | Clark et al. | |
| 4,257,416 A | 3/1981 | Prager | |
| 4,340,048 A | 7/1982 | Eckenhoff | |
| 4,415,003 A | 11/1983 | Paradis et al. | |
| 4,498,843 A | 2/1985 | Schneider et al. | |
| 4,544,369 A | 10/1985 | Skakoon et al. | |
| 4,552,561 A | 11/1985 | Eckenhoff et al. | |
| 4,657,486 A | 4/1987 | Stempfle et al. | |
| 4,712,583 A | 12/1987 | Pelmulder et al. | |
| 4,731,726 A | 3/1988 | Allen, III | |
| 4,784,644 A | 11/1988 | Sawyer et al. | |
| 4,797,144 A | 1/1989 | DeMeritt et al. | |
| 4,840,754 A * | 6/1989 | Morgan | 264/2.2 |
| 4,936,833 A | 6/1990 | Sams | |
| 4,938,742 A | 7/1990 | Smits | |
| 4,946,448 A | 8/1990 | Richmond | |
| 4,947,856 A | 8/1990 | Beard | |
| 4,958,661 A | 9/1990 | Holtermann et al. | |
| 4,966,199 A | 10/1990 | Ruschke | |
| 5,019,974 A | 5/1991 | Beckers | |
| 5,050,612 A | 9/1991 | Matsumura | |
| 5,147,323 A | 9/1992 | Haber et al. | |
| 5,218,993 A | 6/1993 | Steinberg et al. | |
| 5,246,634 A | 9/1993 | Ichikawa et al. | |
| 5,370,635 A | 12/1994 | Strausak et al. | |
| 5,584,815 A | 12/1996 | Pawelka et al. | |
| 5,645,855 A | 7/1997 | Lorenz | |
| 5,674,557 A * | 10/1997 | Widman et al. | 264/2.3 |
| 5,709,662 A | 1/1998 | Olive et al. | |
| 5,762,632 A | 6/1998 | Whisson | |
| 5,775,671 A | 7/1998 | Cote, Sr. | |
| 5,822,715 A | 10/1998 | Worthington et al. | |
| 5,858,001 A | 1/1999 | Tsals et al. | |
| 6,003,736 A | 12/1999 | Ljunggren | |
| 6,017,331 A | 1/2000 | Watts et al. | |
| 6,056,718 A | 5/2000 | Funderburk et al. | |
| 6,305,661 B1 | 10/2001 | Kennedy | |
| 6,311,712 B1 | 11/2001 | Meyer | |
| 6,315,929 B1 | 11/2001 | Ishihara et al. | |
| 6,390,120 B1 | 5/2002 | Guala | |
| 6,409,707 B1 | 6/2002 | Guala | |
| 6,572,586 B1 | 6/2003 | Wojcik | |
| 6,627,124 B1 | 9/2003 | Herbrechtsmeier et al. | |
| 6,648,859 B2 | 11/2003 | Bitdinger et al. | |
| 6,723,086 B2 | 4/2004 | Bassuk et al. | |
| 6,813,906 B1 | 11/2004 | Hirota et al. | |
| 6,945,963 B2 | 9/2005 | Langley et al. | |
| 7,044,125 B2 | 5/2006 | Vedrine et al. | |
| 7,081,108 B2 | 7/2006 | Langley et al. | |
| 7,104,973 B2 | 9/2006 | Woolston et al. | |
| 7,123,985 B2 | 10/2006 | Wildsmith et al. | |
| 7,302,311 B2 | 11/2007 | Varis | |
| 7,407,490 B2 | 8/2008 | Bendsen et al. | |
| 7,470,266 B2 | 12/2008 | Massengale et al. | |
| 7,510,544 B2 | 3/2009 | Vilks et al. | |
| 7,537,590 B2 | 5/2009 | Santini, Jr. et al. | |
| 7,585,167 B2 | 9/2009 | Lawton et al. | |
| 7,637,899 B2 | 12/2009 | Woolston et al. | |
| 7,846,146 B2 | 12/2010 | Woolston et al. | |
| 7,850,663 B2 | 12/2010 | Sullivan et al. | |
| 7,896,002 B2 | 3/2011 | Watanabe | |
| 7,914,499 B2 | 3/2011 | Gonnelli et al. | |
| 7,935,280 B2 | 5/2011 | Lawton et al. | |
| 7,967,795 B1 | 6/2011 | Cabiri | |
| 8,021,334 B2 | 9/2011 | Shekalim | |
| 2002/0119711 A1 | 8/2002 | VanAntwerp et al. | |
| 2003/0100883 A1 | 5/2003 | Kristensen et al. | |
| 2003/0180164 A1 | 9/2003 | Bunner et al. | |
| 2004/0050104 A1 | 3/2004 | Ghosh et al. | |
| 2004/0176727 A1 | 9/2004 | Shekalim | |
| 2005/0065500 A1 | 3/2005 | Couvillon, Jr. et al. | |
| 2005/0192557 A1 | 9/2005 | Brauker et al. | |
| 2006/0021386 A1 * | 2/2006 | Wang | 65/323 |
| 2006/0073232 A1 | 4/2006 | Wang | |
| 2006/0145372 A1 | 7/2006 | Jones et al. | |
| 2007/0073230 A1 | 3/2007 | Jasperson et al. | |
| 2007/0087068 A1 | 4/2007 | Eiha et al. | |
| 2007/0225147 A1 | 9/2007 | Hayashi et al. | |
| 2007/0233008 A1 | 10/2007 | Kristensen et al. | |
| 2007/0299398 A1 | 12/2007 | Alferness et al. | |
| 2008/0169444 A1 | 7/2008 | Guala | |
| 2009/0062767 A1 | 3/2009 | Van Antwerp et al. | |
| 2009/0105658 A1 | 4/2009 | Jennewine | |
| 2010/0004603 A1 | 1/2010 | Kristensen et al. | |
| 2010/0081993 A1 | 4/2010 | O'Connor | |
| 2010/0185322 A1 | 7/2010 | Bylsma et al. | |
| 2010/0225013 A1 | 9/2010 | Eiha et al. | |
| 2010/0255366 A1 | 10/2010 | Myland | |
| 2010/0280461 A1 | 11/2010 | Forstreuter | |
| 2010/0317093 A1 | 12/2010 | Turewicz et al. | |
| 2011/0021905 A1 | 1/2011 | Patrick et al. | |
| 2011/0066131 A1 | 3/2011 | Cabiri | |
| 2011/0114744 A1 | 5/2011 | Ricciardi et al. | |
| 2011/0118675 A1 | 5/2011 | Miller et al. | |
| 2011/0137287 A1 | 6/2011 | Gonnelli et al. | |
| 2011/0168294 A1 | 7/2011 | Jakobsen et al. | |
| 2011/0251546 A1 | 10/2011 | Sullivan et al. | |
| 2011/0274566 A1 | 11/2011 | Amirouche et al. | |
| 2011/0308650 A1 | 12/2011 | Amirouche et al. | |
| 2011/0309229 A1 | 12/2011 | Amirouche et al. | |
| 2012/0002422 A1 | 1/2012 | Lia et al. | |
| 2012/0053571 A1 | 3/2012 | Petri | |
| 2013/0144214 A1 | 6/2013 | Amirouche et al. | |
| 2013/0144254 A1 | 6/2013 | Amirouche et al. | |

FOREIGN PATENT DOCUMENTS

| | | |
|---|---|---|
| GB | 2 248 891 A | 4/1992 |
| JP | 62-297120 A | 12/1987 |
| JP | 2007-015906 A | 1/2007 |
| JP | 2007-119280 A | 5/2007 |
| JP | 2008-96089 A | 4/2008 |
| WO | WO 03/047426 A1 | 6/2003 |
| WO | WO 2004/067964 A | 8/2004 |
| WO | WO 2006/111775 A | 10/2006 |
| WO | WO 2007/055642 A1 | 5/2007 |
| WO | WO 2009/048462 A1 | 4/2009 |
| WO | WO 2010/128914 A1 | 11/2010 |

OTHER PUBLICATIONS

"Silastic Biomedical Grade Liquid Silicone Rubbers", Dow Corning, 2006, accessed at http://www4.dowcorning.com/DataFiles/090007c880097f96.pdf.*

"Silastic BioMedical Grade ETR elastomers", Dow Corning, 2002-2011, accessed at http://www4.dowcorning.com/DataFiles/090007c88028669a.pdf.*

Davis, Robert; "Techniques for Improved Soft Lens Fitting"; Aug. 1, 2005, p. 2, accessed at http://www.clspectrum.com/articleviewer.aspx?articleid=12852.*

Pallikaris, Ioannis; "Intracorneal mico-lens a minimally invasive option for presbyopia"; Aug. 10, 2010, p. 1, paragraph 003, accessed at http://www.rigneygraphics.com/clients/presbia/website/newsmedia/pdfs/press-osn-presbia.pdf.*

A. Manz, N. Graber, and H. Widmer, "Miniaturized total chemical analysis systems: a novel concept of chemical sensing," Sensors and Actuators B, vol. 1, pp. 244-248, 1990.

C. Koch, V. Remcho, and J. Ingle, "PDMS and tubing-based peristaltic micropumps with direct actuation," Sensors and Actuators B, vol. 135, pp. 664-670, 2009.

H. van Lintel, F. V. de Pol, and S. Bouwstra, "A piezoelectric micropump based on micromachining of silicon," Sensors and Actuators A, vol. 15, p. 153-167, 1988.

N. Nguyen, X. Huang and T. Chuan, "MEMS-micropumps: a review," Journal of Fluids Engineering, vol. 124, p. 384-392, 2002.

(56) References Cited

OTHER PUBLICATIONS

A. Acevedo, Creation of Dual Chamber Micropump Using Rapid Prototyping, Milwaukee School of Engineering.
"Small, powerful, light, precise: micro diaphragm pumps made of plastics," Mar. 2009, [online] http://www.thinxxs.com/main/produkte/micropumps.html.
"Bartels micropumps," Apr. 2009, [online] http://www.bartelsmikrotechnik.de/index.php/micropumps.html.
"Precision products," Mar. 2009, [online] http://www.star-m.jp/eng/products/precision/index/html.
O. Jeong, S. Park, S. Yang, and J. Pak, "Fabrication of a peristaltic PDMS micropump," Sensors and Actuators A, vol. 123-124, pp. 453-458, 2005.
C. Yamahata, C. Lotto, E. Al-Assaf, and M. Gijs, "A PMMA valveless micropump using electromagnetic actuation," Microfluid Nanofluid, vol. 1, pp. 197-207, 2005.
T. Pan, S. McDonald, E. Kai, and B. Ziaie, "A magnetically driven PDMS micropump with ball check-valves," J. Micromech. Microeng, vol. 15, pp. 1021-1026, 2005.
F. Trenkle, S. Haeberle, and R. Zengerle, "Normally-closed peristaltic micropump with re-usable actuator and disposable fluidic chip," Sensors and Actuators B 54, Science Direct, vol. 1, pp. 1515-1518, 2011.
S. Ha, W. Cho, and Y. Ahn, "Disposable thermo-pneumatic micropump for bio lab-on-a-chip application," Microelectronic Engineering, vol. 86, pp. 1337-1339, 2009.
R. Irawan, S. Swaminathan, P. Aparajita, and S. Tjin, "Fabrication and performance testing of disposable micropump suitable for microfluidic chip," in Intl. Conf. on Biomedical and Pharmaceutical Engineering, Orchard Hotel, Singapore, Dec. 2006, pp. 252-255.
M. Zhu, P. Kirby, M. Wacklerle, M. Herz, and M. Richter, "Optimization design of multi-material micropump using finite element method," Sensors and Actuators A, vol. 149-1, pp. 130-135, 2009.
S. Bohm, W. Olthuis, and P. Bergveld, "A plastic micropump constructed with conventional techniques and materials," Sensors and Actuators A, vol. 77-3, pp. 223-228, 1999.
N. Nguyen and S. Wereley, Fundamentals and Applications of Microfluidics, ch. 3, Fabrication Techniques for Microfluidics, pp. 293-341(Artech House), 2002.
Y. Fu, H. Du, W. Huang, S. Zhang, and M. Hu, "Tini-based thin films in MEMS applications: a review," Sensors and Actuators A, vol. 112(23), pp. 395-408, 2004.
D. Laser and J. Santiago, "A review of micropumps," J. Micromech. Microeng., vol. 14(6), pp. 35-64, 2004.
V. Singhal, S. Garimella, and A. Raman, "Microscale pumping technologies for microchannel cooling systems," Appl Mech Rev, vol. 57(3), pp. 191-221, 2004.
N. Tsai and C. Sue, "Review of mems-based drug delivery and dosing systems," Sensors and Actuators A, vol. 134(2), pp. 555-564, 2007.
P. Dario, N. Croce, M. Carrozza, and G. Varallo, "A fluid handling system for a chemical microanalyzer," J. Micromech. Microeng., vol. 6, pp. 95-98, 1996.
H. Li, D. Roberts, et al., "A high frequency high flow rate piezoelectrically driven MEMS micropump," in Proceedings IEEE Solid State Sensors and Actuators Workshop, Hilton Head, SC, Jun. 2000.
K. Junwu, Y. Zhigang, P. Taijiang, C. Guangming, and W. Boda, "Design and test of a high-performance piezoelectric micropump for drug delivery," Sensors and Actuators A, vol. 121, pp. 156-161, 2005.
H. Ma, B. Hou, H. Wu, C. Lin, J. Gao, and M. Kou, "Development and application of a diaphragm micro-pump with piezoelectric device," Microsyst Technol, vol. 14, pp. 1001-1007, 2008.
S. Santra, P. Holloway, and C. Batich, "Fabrication and testing of a magnetically actuated micropump," Sensors and Actuators B, vol. 87, pp. 358-364, 2002.
M. Shen, C. Yamahata, and M. Gijs, "Miniaturized PMMA ball-valve micropump with cylindrical electromagnetic actuator," Microelectronic Engineering, vol. 85, pp. 1104-1107, 2008.
"Diabetes Basics: Diabetes Statistics," American Diabetes Association, [Online]. Available at: http://www.diabetes.org/diabetes-basics/. [Accessed May 14, 2012].
"Diabetic Neuropathy, Living With Numbness and Pain," A Diabetic Life, [Online], Available at: http://www.a-diabetic-life.com/diabetic-neuropathy.html. [Accessed May 5, 2012].
"Electromyogram (EMG)," Medicine.net.com, [Online], Available at: http://www.medicinenet.com/electromyogram/article.htm. [Accessed May 15, 2012].
"Nerve conduction velocity," MedlinePlus®, A Service of the U.S. National Library of Medicine, National Institutes of Health, [Online] Available at: http://www.nlm.nih.gov/medlineplus/ency/article/003927,htm; updated Jun. 18, 2011.
"Peripheral Neuropathy Fact Sheet," National Institute of Neurological Disorders and Stroke, NIH Publication No. 04-4853, [Online]. Available:http://www.ninds.nih.gov/disorders/peripheralneuropathy/detail_peripheralneuropathy.htm; updated Sep. 19, 2012.
"Peripheral Neuropathy Market Approaches US$1B by 2012," PR Newswire United Business Media [Online], Available at: http://www.prnewswire.co.uk/news-releases/peripheral-neuropathymarket-approaches-us1b-by-2012-154534705.html. Apr. 7, 2012.
Amirouche et al., "Current Micropump Technologies and Their Biomedical Applications," Microsystem Technology, 2009, pp. 647-666, vol. 15.
Anhalt et al., "Insulin Patch Pumps: Their Development and Future in Closed-Loop Systems," Diabetes Technology & Therapeutics, 2010, pp. 51-58, vol. 12.
Bak et al., "Multiple Insulin Injections Using a Pen Injector Versus Insulin Pump Treatment in Young Diabetic Patients," Diabetes Research, 1987, pp. 155-158, vol. 6.
Barbano et al., "Effectiveness, Tolerability, and Impact on Quality of Life of the 5% Lidocaine Patch in Diabetic Polyneuropathy," Archives of Neurology, 2004, pp. 914-918, vol. 61, No. 6.
Casella et al., "Accuracy and Precision of Low-Dose Insulin Administration," Pediatrics, 1993, pp. 1155-1157, vol. 91.
Einhorn et al., "Advances in Diabetes for the Millennium: Insulin Treatment and Glucose Monitoring," Medscape General Medicine, 2004, p. 8, vol. 6, (3 Suppl.) [Online], Available at: http://www.medscape.org/viewarticle/488996 (9 pages).
Elleri et al., "Closed-Loop Insulin Delivery for Treatment of Type 1 Diabetes," BMC Medical, 2011, p. 120, vol. 9 [Online]. Available at: http://www.biomedcentral.com/1741-7015/9/120 (9 pages).
Farnbach, "Peripheral Nerve Testing and Electromyography," [Online]. Available at: http://cal.vet.upenn.edu/projects/saortho/appendix_d/appd.htm. [Accessed May 18, 2012].
Galer et al., "The Lidocaine Patch 5% Effectively Treats All Neuropathic Pain Qualities: Results of a Randomized, Double-Blind, Vehicle-Controlled, 3-Week Efficacy Study with Use of the Neuropathic Pain Scale," The Clinical Journal of Pain, 2002, pp. 297-301, vol. 18, No. 5 (Abstract).
Gammaitoni et al., "Pharmacokinetics and Tolerability of Lidocaine Patch 5% with Extended Dosing," The Annals of Pharmacotherapy, 2002, pp. 236-240, vol. 36, No. 2 (Abstract).
Ignaut et al., "Comparative Device Assessments: Humalog KwikPen Compared with Vial and Syringe and FlexPen," The Diabetes Educator, 2009, pp. 789-798, vol. 35, No. 2.
International Search Report and Written Opinion issued in International Patent Application No. PCT/US2009/059020, mailed Mar. 9, 2010 (17 pages).
International Search Report and Written Opinion issued in International Patent Application No. PCT/US2012/066937, mailed Mar. 7, 2013 (7 pages).
International Search Report and Written Opinion issued in International Patent Application No. PCT/US2013/035918, mailed Jun. 21, 2013 (9 pages).
International Search Report and Written Opinion issued in International Patent Application No. PCT/US2013/035921, mailed Jul. 1, 2013 (11 pages).
Klonoff et al., "Insulin Pump Safety Meeting: Summary Report," Journal of Diabetes Science and Technology, 2009, pp. 396-402, vol. 3, No. 2.
Lee et al., "Microfluicic mixing: A review," Int. J. Mol. Sci., 2011, pp. 3263-3287, vol. 12.

(56) References Cited

OTHER PUBLICATIONS

Meece et al., "Effect of Insulin Pen Devices on the Management of Diabetes Mellitus," Am J Health-Syst. Pharm., 2008, pp. 1076-1082, vol. 65.

Melin et al., "A fast passive and planar liquid sample micromixer," Lab on a Chip, 2004, pp. 214-219, vol. 4.

Morrow, "Transdermal Patches Are More Than Skin Deep," Managed Care [Online]. Available at: http://www.managedcaremag.com/archives/0404/0404.biotech.html. Apr. 2004.

Mundell, "Antidepressant Cymbalta Might Ease Chemo-Linked Pain," MSN Health, [Online]. Available at: htpp://health.msn.com/health-topics/cancer/antidepressant-cymbalta-might-ease-chemo-linked-pain. 2013.

Nisar et al., "MEMS-based Micropumps in Drug Delivery and Biomedical Applications," Sensors and Actuators B, 2008, pp. 917-942, vol. 130.

Rapp et al., "Liga micropump for gases and liquids," Sensors and Actuators A, 1994, pp. 57-61, vol. 40, No. 1.

Richardson et al., "Peripheral Neuropathy: A True Risk Factor for Falls," The Journal of Gerontology: Series A, 1995, pp. 211-215, vol. 50, No. 4 (Abstract).

Roberts, "Blind Attack on Wireless Insulin Pumps Could Deliver Lethal Dose," Threatpost.com, The Kaspersky Lab Security News Service. Oct. 27, 2011, 2 pages.

Rosielle, "The Lidocaine Patch," Medical College of Wisconsin [Online]. Available: http://www.eperc.mcw.edu/EPERC/FastFactsIndex/ff_148.htm. [Accessed May 15, 2012].

Selam, "Evolution of Diabetes Insulin Delivery Devices," Journal of Diabetes Science and Technology, 2010, pp. 505-513, vol. 4, No. 3.

U.S. Appl. No. 13/174,598, filed Jun. 30, 2011, by Amirouche et al.: Non-Final Rejection, dated May 14, 2013.

U.S. Appl. No. 13/174,624, filed Jun. 30, 2011 by Amirouche et al.: Final Rejection, dated Nov. 21, 2012.

U.S. Appl. No. 13/174,624, filed Jun. 30, 2011 by Amirouche et al.: Non-Final Rejection, dated Feb. 8, 2013.

U.S. Appl. No. 13/174,624, filed Jun. 30, 2011 by Amirouche et al.: Non-Final Rejection, dated Jun. 28, 2012.

U.S. Appl. No. 13/416,249, filed Mar. 9, 2012, by Amirouche et al.

U.S. Appl. No. 13/448,013, filed Apr. 16, 2012, by Amirouche et al.

U.S. Appl. No. 13/470,140, filed May 11, 2012, by Amirouche et al.

U.S. Appl. No. 13/649,202, filed Oct. 11, 2012, by Amirouche.

U.S. Appl. No. 13/649,202, filed Oct. 11, 2012, by Amirouche: Non-Final Rejection, dated Jun. 18, 2013.

U.S. Appl. No. 13/692,868, filed Dec. 3, 2012, by Amirouche et al.

Yadav et al., "Various Non-Injectable Delivery Systems for the Treatment of Diabetes Mellitus," Endocrine, Metabolic & Immune Disorders-Drug Targets, 2009, pp. 1-13, vol. 9, No. 1.

\* cited by examiner

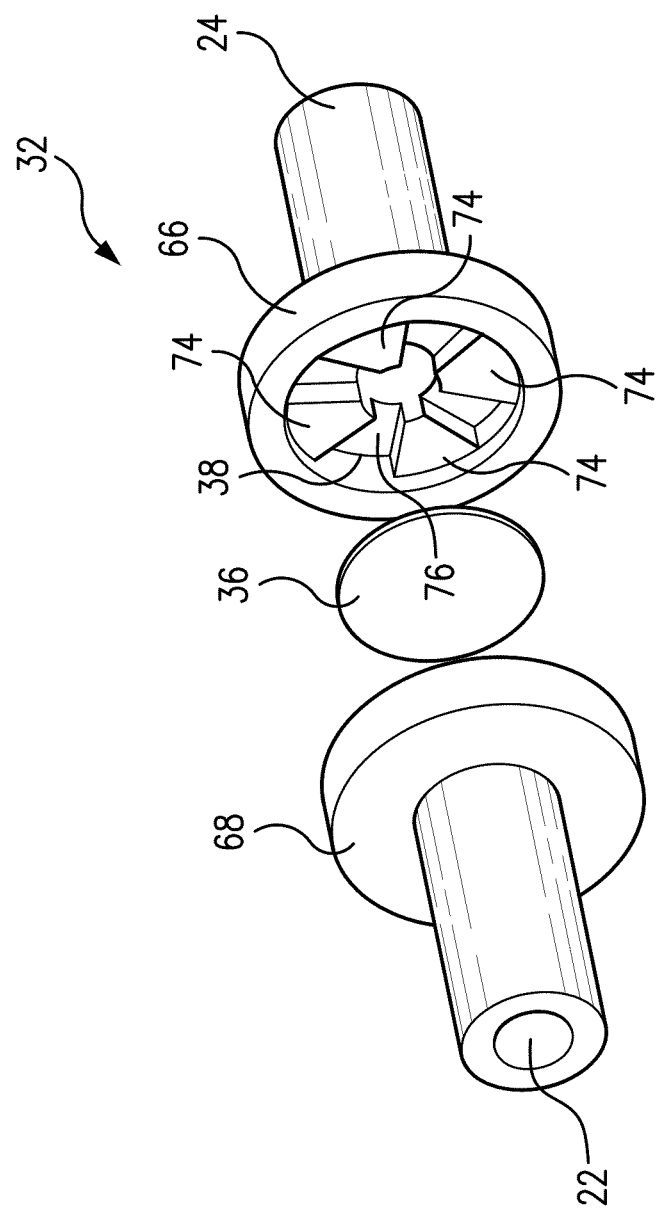

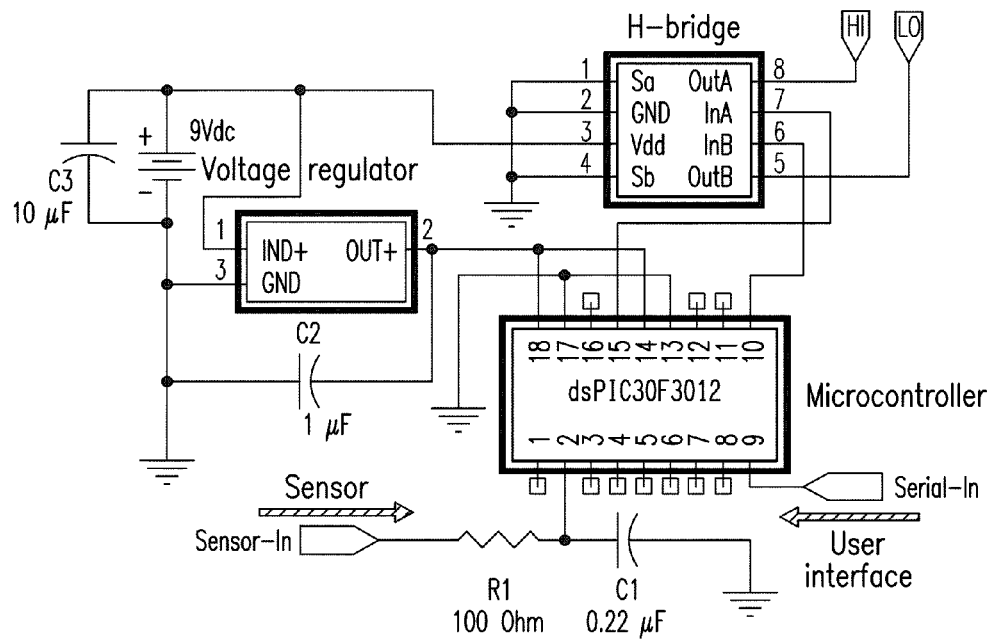
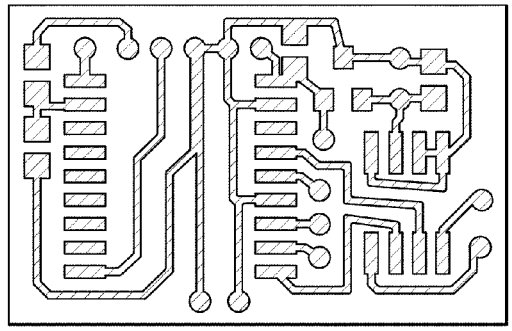
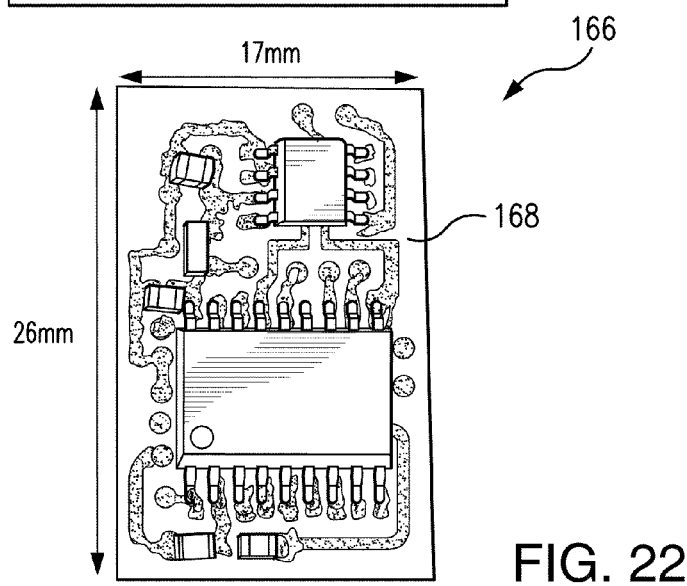
FIG. 22

METHOD OF MAKING A MEMBRANE FOR USE WITH A FLOW CONTROL SYSTEM FOR A MICROPUMP

CROSS REFERENCE TO RELATED APPLICATIONS

This application is a continuation-in-part of International Application No. PCT/US/059020, filed Sep. 30, 2009, which is herein incorporated in its entirety and which in turn claims priority to U.S. provisional patent application Ser. No. 61/152,165, filed Feb. 12, 2009. This application also claims priority to U.S. provisional patent application Ser. No. 61/448,050, filed Mar. 1, 2011.

FIELD OF THE INVENTION

The present disclosure relates to a method of making a membrane for use with a flow control system for a magnetically driven micropump for handling small fluid volumes. In particular, in association with a micropump including a magnetically actuated membrane to transfer fluids and an innovative flow control system therefor, a method of making a membrane designed particularly therefor is disclosed.

BACKGROUND OF THE INVENTION

The present disclosure relates to a method of making a membrane for use with a flow control system for a magnetically driven micropump for handling small fluid volumes. In particular, in association with a micropump including a magnetically actuated membrane to transfer fluids and an innovative flow control system therefor, a method of making a membrane designed particularly therefor is disclosed.

The field of microfluidics generally encompasses handling very small fluid volumes on the order of several nanoliters. Microfluidics has increasingly important applications in such fields as life sciences and chemical analysis. Microfluidics devices, also known as micromechanical systems (MEMS), include devices for fluid control, fluid measurement, medical testing, DNA and protein analysis, in vivo drug delivery, and other biomedical applications.

Typical fluid flow rates of micropumps range from approximately 0.1 microliter per minute to several (80-180) milliliters per minute. Flow rates on this order are useful in applications such as disposable micro total analysis systems (µTAS) or lab-on-a-chip (LOC) for chemical and biological analysis, point of care testing (POCT) for medical diagnostic testing, implantable drug delivery systems for medications (such as insulin) requiring a fine degree of regulation and precise control, and cardiology systems for blood transport and pressurization.

Since most of MEMS processing techniques evolved from microelectronics, the first silicon micropump was based on a piezoelectric actuation of a thin membrane in 1980s primarily for use in the controlled insulin delivery systems. This work demonstrated the feasibility of silicon-based micropump and inspired extensive research on silicon micropumps. Also, several commercially available implantable silicon micropumps were reported for insulin delivery and therapeutic agents dispensing through pharmaceutical and clinical therapy fields.

Recently, a number of polymeric materials and new microfabrication techniques, such as soft lithography, microstereolithography, micromolding and polymeric surface micromachining, have been investigated and developed for a growing trend of low cost, integrated and miniaturized disposable µTAS applications. Many polymeric materials including plastics and elastomers have been increasingly incorporated into other microdevices as substrates, structural membranes, and functional membranes due to their excellent mechanical properties, good chemical resistance, and low fabrication cost. Among the most popular polymers, polydimethylsiloxane (PDMS) has been extensively utilized in microfluidic devices because of excellent biocompatibility, simple fabrication process (molding and reversible bonding) and optical transparency (facilitating monitoring and interrogating) as well as elasticity (good sealing and connecting).

Silicon-based and plastic-based MEMS valveless micropumps are taken as an example to compare with a PDMS-based micropump. The fabrication process of the silicon-based MEMS micropump involved three subsequent Deep Reactive Ion Etching (DRIE) steps and one silicon-glass anodic bonding step while LIGA, microinjection, or hot embossing molding and multiple thin plate assembly with adhesives or bolts was involved for the plastic pumps. On the other hand, for a PDMS-based micropump only multilayer soft lithography processes and PDMS-PDMS bonding techniques are usually required. From the fabrication cost point of view, a MEMS PDMS-based micropump is considerably lower than the former two types of micropumps.

There is an increasing interest for embedded systems with feedback control and subsequent delivery of more than one drug, handling small and precise (accurate) volumes of fluids. Such applications include drug delivery pain management and micro total analysis systems (µTAS). A. Manz, N. Graber, and H. Widermer, "Miniaturized total chemical analysis systems: a novel concept of chemical sensing," *Sensors and Actuators B*, vol. 1, pp. 244-248, 1990. Micropumps are one of the main components of these systems and are often the limiting factor for size, weight and cost. For this purpose, a number of micropumps have been designed and fabricated utilizing a variety of different technologies.

These include modifications and downsizing, or scaling down, the current pumps used for insulin delivery. Commercial applications involving active micropumps, such as insulin delivery systems, are typically based on classical electrical motors in designs such as syringe pumps or peristaltic pumps. These designs are cost-effective, and trials have been performed to reduce their size. C. Koch, V. Remcho, and J. Ingle, "PDMS and tubing-based peristaltic micropumps with direct actuation," *Sensors and Actuators B*, vol. 135, pp. 664-670, 2009. However, the size of the electric motors which are necessary for delivering the desired forces prevents miniaturization below the 40-50 mm range. This severely limits the scope of applications to large and bulky drug delivery systems.

Silicon-based MEMS micropumps have been used, mostly by employing piezoelectric actuation. H. van Lintel, F. V. de Pol, and S. Bouwstra, "A piezoelectric micropump based on micromachining of silicon," *Sensors and Actuators A*, vol. 15, p. 153-167, 1988; N. Nguten, "Mems-micropumps: a review," *Journal of Fluids Engineering*, vol. 124, p. 384-392, 2002; F. Tray and W. Choong, *Creation of Dual Chamber Micropump Using Rapid Prototyping*, Kluwer Academic, 2002. However, the material cost of silicon and related fabrication issues burden its use.

Lower cost micropumps have been attempted using materials such as plastic, see, e.g., "Small, powerful, light, precise: micro diaphragm pumps made of plastics," March 2009, [online] http://www.thinxxs.com/main/produkte/micropumps.html; "Bartels micropumps," April 2009, [online] http://www.bartelsmikrotechnik.de; and "Precision products," March 2009, [online] http://www.starmicronics.co.jp, PDMS or PDMS+PMMA, see, e.g., O. Jeong, S. Park, S. Yang, and J. Pak, "Fabrication of a peristaltic PDMS micropump," *Sensors and Actuators A*, vol. 123-124, pp. 453-458, 2005; C. Yamahata, C. Lotto, E. A. Assaf, and M. Gijs, "A PMMA valveless micropump using electromagnetic actuation," *Microfluidics and Nanofluidics*, vol. 1, pp. 197-207, 2005; and T. Pan, S. McDonald, E. Kai, and B. Ziaie, "A magnetically driven PDMS micropump with ball check-valves," *J. Micromech. Microeng*, vol. 15, pp. 1021-1026, 2005.

Efforts at disposability have been made. See, e.g., F. Trenkle, S. Haeberle, and R. Zengerle, "Normally-closed peristaltic micropump with re-usable actuator and disposable fluidic chip," Sensors and Actuators B 54, *Science Direct, vol. 1*, pp. 1515-1518, 2011; S. Ha, W. Cho, and Y. Ahn, "Disposable thermo-pneumatic micropump for bio lab-on-a-chip application," *Microelectronic Engineering*, vol. 86, pp. 1337-1339, 2009; and R. Irawan, S. Swaminathan, P. Aparajita, and S. Tjin, "Fabrication and performance testing of disposable micropump suitable for microfluidic chip," in *Intl. Conf. on Biomedical and Pharmaceutical Engineering*, Orchard Hotel, Singapore, December 2006, pp. 252-255. However, the PDMS pumps described are based on expensive microfabrication techniques, which require costly equipment that utilizes an inherently slow process. This limits the ability for manufacturers to mass-produce these types of pumps.

Some studies have focused specifically on reducing fabrication costs by utilizing clever polymer based designs which can be produced with standard fabrication techniques. In M. Zhu, P. Kirby, M. Wacklerle, M. Herz, and M. Richter, "Optimization design of multi-material micropump using finite element method," *Sensors and Actuators A*, vol. 149-1, pp. 130-135, 2009, piezoelectric actuation was used to supply up to 1.8 mL/min with $44 \times 17 \times 8$ mm$^3$ pumps. In S. Bohm, W. Olthuis, and P. Bergveld, "A plastic micropump constructed with conventional techniques and materials," *Sensors and Actuators A*, vol. 77-3, pp. 223-228, 1999, both electromagnetic and piezoelectric actuators were used to supply up to 1.8 mL/min with a $10 \times 10 \times 8$ mm$^3$ pump (electromagnetic version) and 2.1 mL/min with a $12 \times 12 \times 2$ mm$^3$ pump (piezo version). They were successful in reducing manufacturing costs but not to the point desired for disposable systems. In the case of piezoelectric actuators, piezoelectric materials are expensive and they require high operating voltages. This requires the use of specialized, expensive, and bulky electronics, which is especially difficult to incorporate in embedded applications. In the case of electromagnetic actuators, an expensive and bulky coil is required inside the pump. In both cases, electrodes and supply wiring are needed in the pump body itself, which increases the volume and price of the pump.

For drug delivery and µTAS applications, disposable pumps would be especially desirable since it would eliminate the need for cleaning and sterilizing after each use and would decrease the risk of chemical impurities or biological contamination. Unfortunately, the relatively high cost of micropumps today prevents disposable use, which strongly limits the scope of their applications.

Another feature common to all of the aforementioned micropumps is an open-loop control system with flow rates dependent on the driving frequency alone. This often leads to a lack of reproducibility and a lack of flow rate predictability. As a result, the ability to supply precise flow rates and doses is severely impeded, making them poorly suited for applications such as drug delivery.

In each of the aforementioned systems, no provision of a method for producing the innovative and very small valve membrane disclosed herein is made.

Thus, a problem associated with devices that precede the present disclosure is that they do not provide, in combination with the other features and advantages disclosed herein, a method of manufacture of a suitable valve membrane to be installed in a flow control system for use with a micropump having a disposable subassembly that can be readily mated with an actuation assembly.

Yet another problem associated with devices that precede the present disclosure is that they do not provide, in combination with the other features and advantages disclosed herein, a method of manufacture of a suitable valve membrane to be installed in a flow control system for use with a micropump that can be readily configured for use in medical applications.

Still a further problem associated with devices that precede the present disclosure is that they do not provide, in combination with the other features and advantages disclosed herein, a method of manufacture of a suitable valve membrane to be installed in a flow control system for use with a micropump having a relative low cost of manufacture while at the same time providing a sterile product having disposable parts.

An additional problem associated with devices that precede the present disclosure is that they do not provide, in combination with the other features and advantages disclosed herein, a method of manufacture of a suitable valve membrane to be installed in a flow control system for use with a micropump having the requisite precision governing volumetric flowrate, which is particularly important in medical applications.

Another problem associated with devices that precede the present disclosure is that they do not provide, in combination with the other features and advantages disclosed herein, a method of manufacture of a suitable valve membrane to be installed in a flow control system for use with a micropump that prevents reverse flow or backflow, which is particularly important in medical applications.

An even further problem associated with devices that precede the present disclosure is that they do not provide, in combination with the other features and advantages disclosed herein, a method of manufacture of a suitable valve membrane to be installed in a flow control system for use with a micropump having an efficient power-consumption profile, thereby maximizing battery life.

There is a demand, therefore, to overcome the foregoing problems while at the same time providing a method of manufacture of a suitable valve membrane to be installed in a flow control system for use with a micropump that is relatively low in cost to manufacture and yet possesses extended durability.

SUMMARY OF THE INVENTION

The method of manufacture of a suitable valve membrane to be installed in a micropump disclosed herein is operated according to the principle that an oscillating membrane results in a variation of pressure in the dual chamber, which directs the dynamic flow of the fluidic conduit using dynamic conforming valves. Often, valves are incorporated as check valves in inlets and outlets of reciprocating micropumps in the forms of cantilever flaps, bridge membranes, spherical balls, mobile structures, nozzles/diffusers or Tesla elements.

More recently, however, as shown in the present disclosure, attention has been given to developing a new valve assembly that provides a dynamic conforming valve assembly, thereby providing better flow control and more effective prevention of backflow. A flow control system is disclosed for use with a micropump for pumping a fluid to be administered through a catheter. The flow control system includes a first body portion, a membrane and a second body portion. The first body portion has a membrane-receiving inner surface, an inlet aperture in fluid communication with the micropump, and a mating surface disposed about the membrane-receiving inner surface and configured to mate with a mating surface of the second body portion. The membrane has a reinforcement annulus configured to be received by the first body portion membrane-receiving inner surface and a domed portion oriented to be movable from a closed position, in sealable communication with the inlet aperture, and an open position, in spaced apart relation from the inlet aperture. The membrane is oriented and sized to be biased in the closed position. The second body portion has a membrane-receiving inner surface, an outlet aperture configured to communicate with the catheter, and a mating surface disposed about the membrane-receiving inner surface and configured to mate with the mating surface of the first body portion. At least a portion of the membrane reinforcement annulus is positioned within the inner surface of the first body portion. The first body portion mating surface is positioned and maintained in sealed relation with the second body portion mating surface. Operation of the micropump causes the fluid to (a) flow from the micropump to the first body inlet aperture, (b) exert a pressure sufficient to move the membrane from the closed position to an open position, (c) flow around the membrane and through the second body outlet aperture and into the catheter.

The micropump of the present disclosure consists of dual fluidic chambers comprising a first chamber and a second chamber and an oscillating actuation membrane disposed therebetween. The membrane is integrated with small bulk magnets and takes advantage of large attractive or repulsive magnetic forces and membrane deflection. The alternating, perpendicular magnetic forces on the membrane result in a large volumetric stroke, which is desired for a high flow rate micropump.

The pump assembly thus includes a flexible membrane disposed between the first chamber and the second chamber. The micropump also includes an actuator assembly configured to cooperate with the pump assembly. The actuator assembly includes a driver magnetically coupled to the membrane, and a sensor configured to detect the position of the membrane, wherein the driver applies a magnetic force to the membrane, causing the membrane to deflect, and wherein such deflection of the membrane results in a change of pressure within the first chamber and the second chamber thereby resulting in fluid flow.

The micropump assembly further includes a housing enclosing an actuator assembly configured to cooperate with the micropump cartridge. The actuator assembly includes a driver magnetically coupled to the membrane, and a first sensor configured to detect the position of the membrane, wherein the driver applies a magnetic force to the membrane, causing the membrane to deflect, and wherein such deflection of the membrane results in a change of pressure within the first chamber and the second chamber thereby resulting in fluid flow. The micropump assembly further including a controller coupled to the driver and configured to control the position of the membrane by receiving input from the first sensor and adjusting the magnetic force applied by the driver. The micropump assembly further including a power supply configured to energize the driver and the controller, wherein the housing is configured such that the micropump cartridge may be inserted into and retained within the actuator assembly.

As thus described, a compact micropump for fluidic/drug delivery applications is disclosed. The micropump can be assembled at low relative cost and provides a disposable pump having a two-component architecture, non-contact actuation, and using standard microfabrication techniques to the extent possible. Closed-loop control of the micropump is achieved by adding inexpensive and accurate sensors to the reusable component without adding the burden of additional cost to the disposable component. Despite its low fabrication cost and small physical size, the micropump performance exceeds design expectations. This is largely due to the pump geometry and dimensions. The micropump this disclosed is small and compact, including the actuators, the pump with fully incorporated valves, and the electronic driver circuit.

Thus, it is an object of the present disclosure to provide, in combination with the other features and advantages disclosed herein, a flow control system for use with a micropump for having a disposable subassembly that can be readily mated with an actuation assembly.

Yet another object of the present disclosure is to provide, in combination with the other features and advantages disclosed herein, a flow control system for use with a micropump that can be readily configured for use in medical applications.

Still a further object of the present disclosure is to provide, in combination with the other features and advantages disclosed herein, a flow control system for use with a micropump having a relative low cost of manufacture while at the same time providing a sterile product having disposable parts.

An additional object of the present disclosure is to provide, in combination with the other features and advantages disclosed herein, a flow control system for use with a micropump having the requisite precision governing volumetric flowrate, which is particularly important in medical applications.

Another object of the present disclosure is to provide, in combination with the other features and advantages disclosed herein, a flow control system for use with a micropump that prevents reverse flow or backflow, which is particularly important in medical applications.

An even further object of the present disclosure is to provide, in combination with the other features and advantages disclosed herein, a flow control system for use with a micropump having a efficient power-consumption profile, thereby maximizing battery life.

The following disclosure provides a flow control system for use with a micropump having the foregoing advantages while at the same time is relatively low in cost to manufacture and possesses extended durability.

BRIEF DESCRIPTION OF THE DRAWINGS

In the detailed description that follows, reference will be made to the following figures:

FIG. 7 is an exploded view of the portion of the preferred embodiment illustrated in FIG. 6;

FIG. 22 is a schematic and photographic illustration of a portion of the preferred embodiment of the micropump showing the electronics thereof;

DETAILED DESCRIPTION OF PREFERRED EMBODIMENTS

Figure 1:
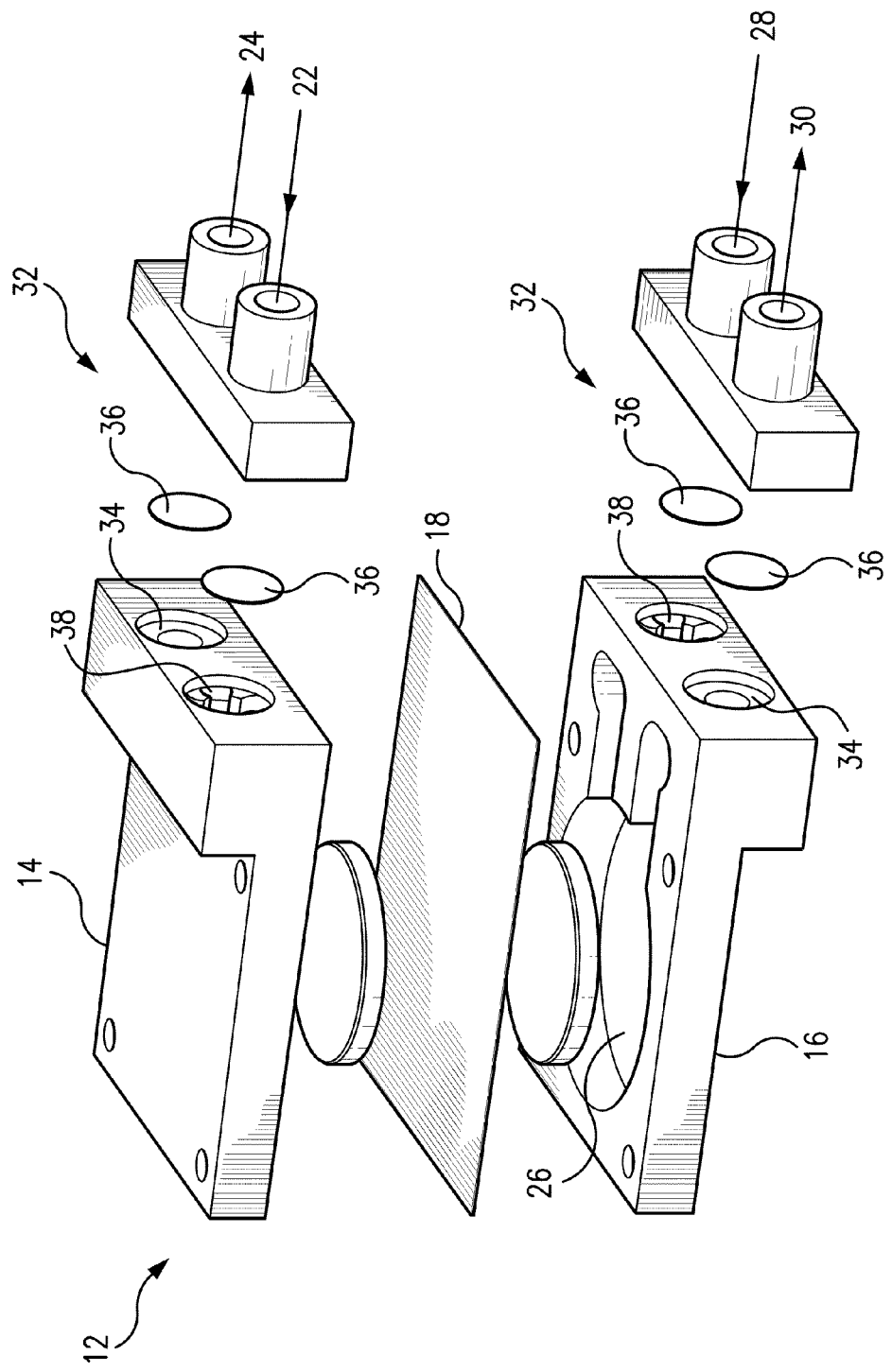
FIG. 1 is a perspective view of an exploded view of a portion of a preferred embodiment of a flow control system for a micropump as disclosed herein.
Figure 2:
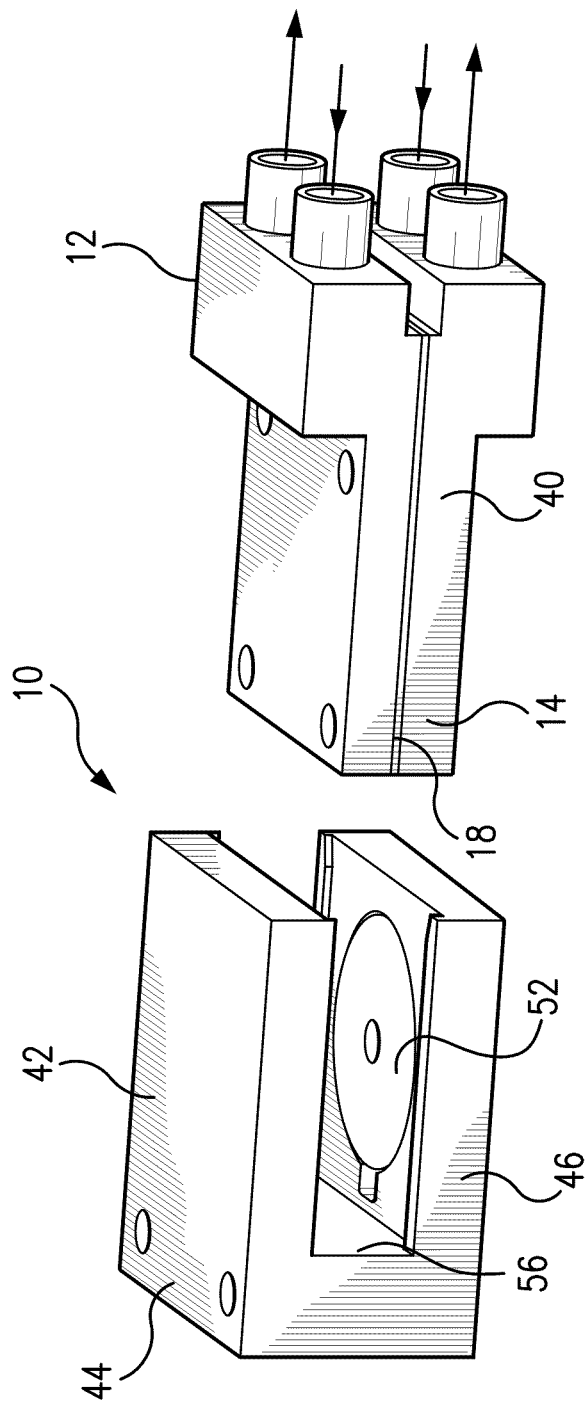
FIG. 2 is an alternative view of the portion of a preferred embodiment illustrated in FIG. 1 as shown in partially-assembled relation.

Referring now to FIGS. 1 and 2, the micropump 10 of the present disclosure includes a pump assembly 12 having a first pump body 14, a second pump body 16 and a flexible membrane 18 disposed therebetween. The first pump body 14 defines a first body flow path and includes a first chamber 20 (shown in FIG. 4). The first pump body 14 further includes a first inlet 22 and a first outlet 24 in fluid communication with the first chamber. Likewise, the second pump body 16 defines a second body flow path and includes a second chamber 26. The second pump body 16 further includes a second inlet 28 and a second outlet 30 in fluid communication with the second chamber 26.

Several proposed actuation mechanisms for micropumps have been reported already, mainly including piezoelectric, electrostatic, electromagnetic, and thermo-pneumatic and shape memory alloy, etc. The majority of the micropumps employ piezoelectric or electrostatic actuation, which operate at a relatively high frequency and require high voltage in magnitude of hundreds to thousands for minimal membrane displacements. As for the electromagnetic actuation, it demonstrates advantageous over other actuation approaches when large displacements, fast response time and relatively low power consumption are highly desired. Magnetic actuation of a membrane with integrated magnets can produce a few hundred μN and a large membrane deflection. These desired properties are highly appealing for many medical applications. Hence, the fluid-membrane coupling effect on the resonant frequency of an electromagnetically driven valveless micropump is discussed in details in the following sections.

The actuation force is applied through an oscillating membrane to drive the working medium in the pump. Therefore, reliability and performance of the micropump depend upon the dynamic characteristics of the composite membrane.

For an oscillating membrane, material properties such as the density, Young's modulus and Poisson's ratio, will significantly influence the natural frequency of the membrane. For example, in MEMS devices the majority of the membranes are integrated composite layers which include some sensing or actuating membrane layers. In this specific example, the characteristics are quite different from the individual material layers. Thus, the equivalent density of the composite layers has to be properly derived.

For a magnetically actuated membrane micropump, there are two schemes for creating the functional membrane. One is soft magnetic material electroplated on the membrane. Another is one or several permanent magnets manually assembled into the PDMS membrane. Then, an external magnetic field is applied either by which a permanent magnet or an integrated planar micro coil in the substrate to control the movement of the membrane. Since the dimension and layout of the bulk magnets embedded in the membrane can influence the distribution of electromagnetic force and the membrane stiffness, a composite membrane is fabricated herein with magnetic properties.

Silicon, silicon nitride and thin metal sheets are suitable as membrane materials for micropumps. For instance, a thin silicon membrane in the range of several micrometers can be realized with current micromachining techniques. However, the Young's modulus of silicon is 190 Gpa, which limits its application for the reciprocating pump. The pump membrane of the present disclosure is made with flexible materials, such as parylene, polyimide, SU-8 and PDMS. These membranes require small actuating pressure and have large deflection as well as large stroke volume. In an exemplary embodiment of the present disclosure, PDMS (Silastic Q7-4750 Silicone Elastomer, Dow Corning Corporation) is used for the micropump actuation membrane and the pump body is Computer Numerical Control (CNC) milled from an acrylic plastic.

Because of its low modulus and good compatibility with silicon and glass substrates, PDMS (Silastic Q7-4750 Silicone Elastomer, Dow Corning Corporation) is selected as the membrane material in the exemplary embodiment. Hard barium ferrite powders (UMBS-IB, Unimagnet Industry Co., Ltd, China) are mixed into PDMS (at 1:1 weight ratio) to develop an actuation membrane. The composite membrane has homogenous and isotropic material properties and can produce bi-directional deflections in an external magnetic field.

One-way flow assemblies 32 (shown more fully in FIG. 6, et seq.) each having a direction of desired flow are provided at both inlets 22, 28 and outlets 24, 30 to ensure proper flow control. Each of these flow assemblies 32 has a supply side seating surface 34, a valve membrane 36 and a discharge side seating surface 38. As will be discussed in greater detail, these are constructed and arranged to facilitate fluid flow in one direction only. It should be apparent that the first pump body 14 has identical features as the second pump body 16, some of which are not visible on both pump bodies 14, 16 as shown in FIGS. 1 and 2.

Referring now to FIG. 2, the micropump 10 may be configured as a pump cartridge 40 insertable into a driver 42. Pump cartridge 40 includes the first pump body 14, the second pump body 16, and the flexible membrane 18 disposed therebetween.

Figure 3:
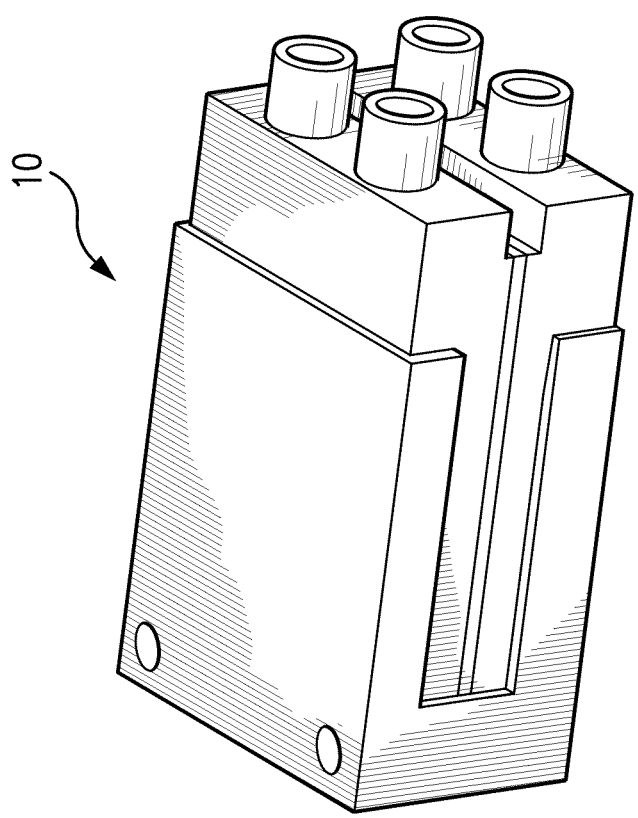
FIG. 3 is an alternative view of the portion of the preferred embodiment illustrated in FIG. 1 as shown in more fully assembled relation.

Driver 42 includes a first support 44 and a second support 46, the second support 46 being disposed separate and apart from the first support 44. The first support 44 includes a first recess (not shown) configured to receive a first solenoid or first activation coil 50 (shown schematically in FIG. 4). Likewise, the second support 46 includes a second recess 52 configured to receive a second solenoid or second activation coil 54 (shown schematically in FIG. 4). The first and second supports 42, 44 define a receptacle 56 configured to receive pump cartridge 38. The assembled micropump 10 is shown in FIG. 3.

Figure 4A:
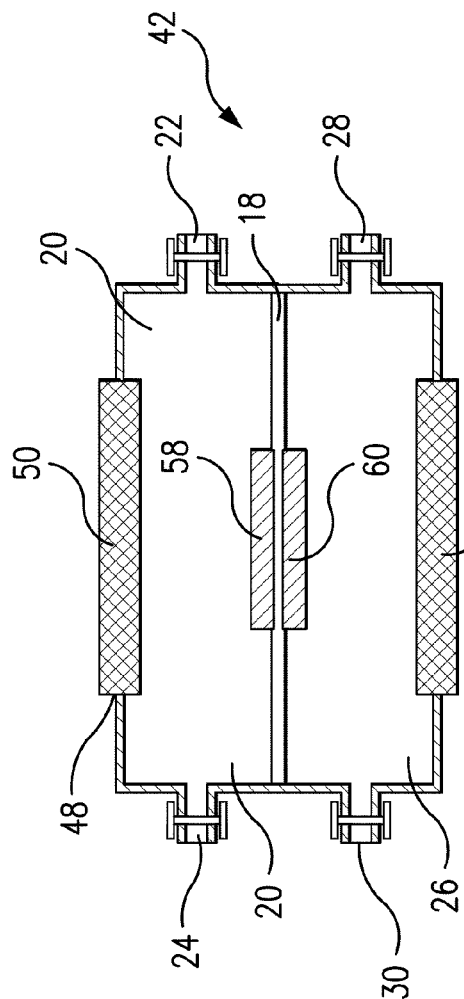
FIG. 4 is a schematic view of a portion of a preferred embodiment of a flow control system for a micropump illustrating features of the actuation principle thereof as disclosed herein.
Figure 4C:
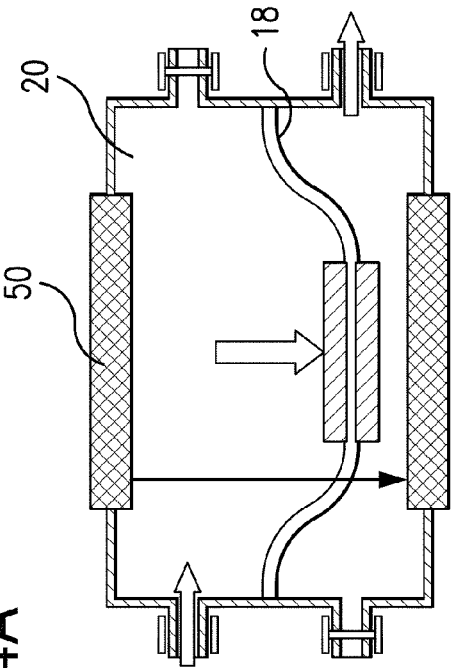
Figure 4B:
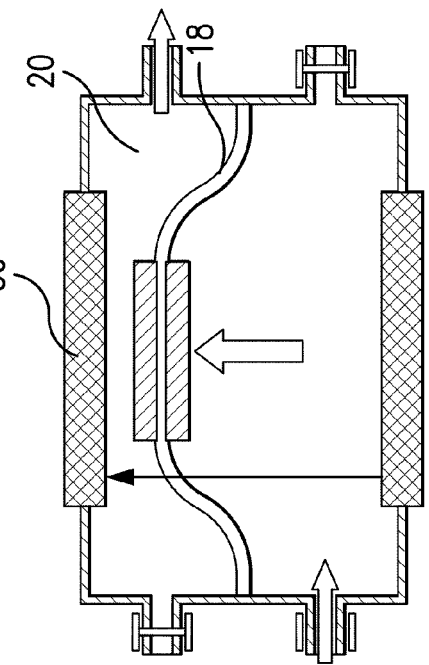
Figure 5C:
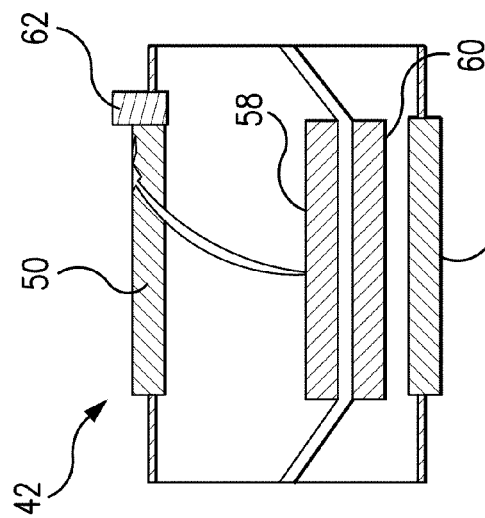
FIG. 5(c) is yet another schematic view of a portion of a preferred embodiment of a flow control system for a micropump illustrating additional features of the actuation principle thereof as disclosed herein.
Figure 5B:
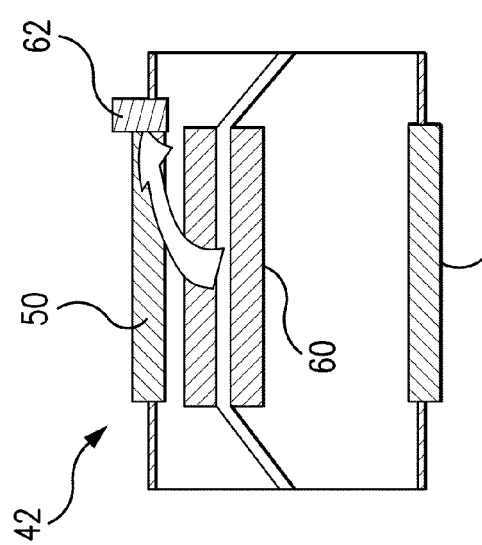
FIG. 5(b) is another schematic view of a portion of a preferred embodiment of a flow control system for a micropump illustrating additional features of the actuation principle thereof as disclosed herein.
Figure 5A:
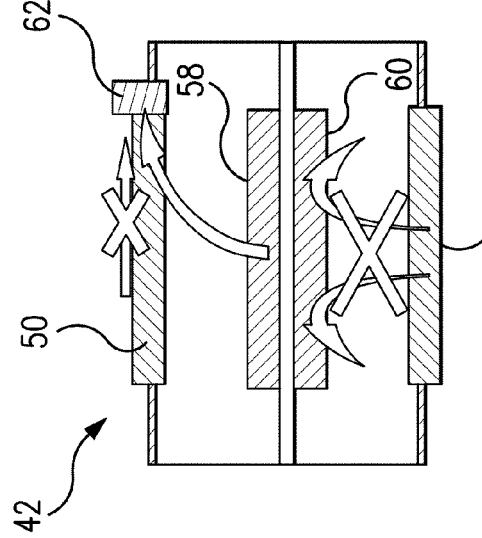
FIG. 5(a) is a schematic view of a portion of a preferred embodiment of a flow control system for a micropump illustrating additional features of the actuation principle thereof as disclosed herein.

Attention is now given to the workings of the driver 42. Referring now to FIGS. 4 and 5, schematic representations of the drive mechanism are provided. The need for non-contact actuation along with low driver voltages leads to the selection of electromagnetic actuation. The pump 10 (FIG. 3) operates by electromagnetically driving membrane magnets 58, 60 in a reciprocating motion within the pump bodies 14, 16. As the magnets 58, 60 and consequently the membrane 18 are displaced, a volumetric change occurs within the pumping chambers 20, 26. This change in volume causes an increased pressure on one side of the membrane 18 and simultaneously a pressure reduction on the other side of the membrane 18. These pressure fluctuations drive the one-way flow assemblies 32 in communication with each respective chamber 20, 26. The flow assemblies 32 are configured so as to be directionally opposed, which results in a net flow. This is more fully discussed as follows.

As shown schematically in FIG. 4, the two chambers 20, 26 work together. The high pressure side of the membrane 18 forces the corresponding first inlet (22) one-way flow assembly 32 closed and drives the fluid through the forward biased first outlet 24. At the same time, the low pressure side of the membrane 18 forces the corresponding second outlet (30) one-way flow assembly 32 closed and draws fluid in through the second inlet 28. When the direction of the membrane 18 is changed, the role of each chamber is reversed.

Figure 26:
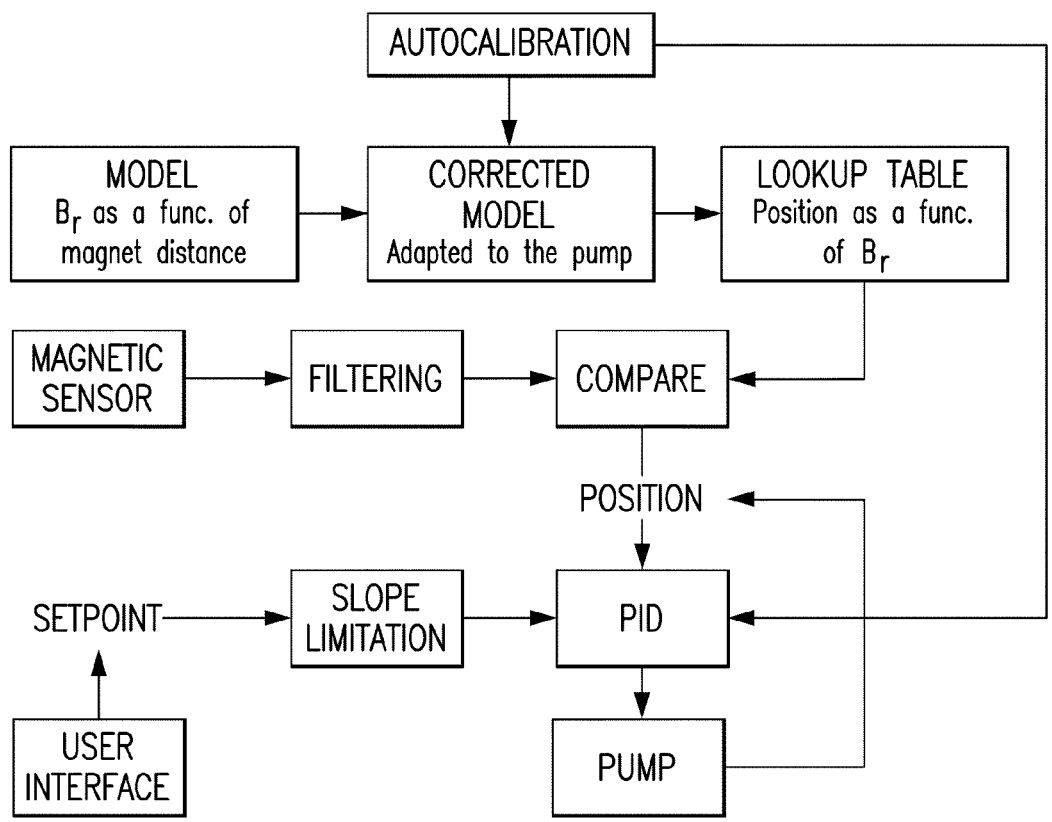
FIG. 26 is a flow chart depicting the principle of control of a preferred embodiment of a micropump.

Returning briefly to FIG. 5, in the micropump 10 of the present disclosure, a control system includes a sensor 62 and a controller (not shown). A schematic representation of the logic of a preferred control system is shown in FIG. 26, as discussed infra. In a preferred arrangement, the sensor 62 is a Hall effect sensor placed in proximity to an actuation coil 50. The flexible membrane 18 moves in reaction to the applied magnetic field (B) of the electromagnetic coils 50, 54. The position of the magnets 58, 60, and thus the deflection of the membrane 18 and the respective volumes of both chambers 20, 26, modifies the magnetic field configuration, which is sampled by the Hall effect sensor 62. A suitable sensor is, by way of example, an A 1301 linear Hall effect sensor manufactured by Allegro Microsystems having a sensitivity of 2.5 mV/Gauss. The position information is provided to the controller and is used to determine the position of the magnets 58, 60 to within an accuracy of 0.05 mm.

The controller dictates the motion of the magnets 58, 60 based on user-selected flow rate requirements. Several modes of operation may be configured, such as a low speed mode, for accurate dosing, or a high speed mode for high volumetric flow rates. The ability to measure the real-time position of the magnet is important because it enables closed-loop flow rate control, it prevents collisions between the magnets and chamber walls, which eliminates collision damage and reduces noise, and it enables high efficiency controlled resonance operating modes. Since the micropump 10 of the present disclosure consists of two separate parts, a contactless sensing system is necessary. It has been found that determining the position of the magnets 58, 60, and thus the membrane 18, is easily accomplished in a cost-effective manner by measuring the magnetic field produced by the magnets 58, 60.

A drawback to this approach has been magnetic noise due to the electromagnetic driver coils 50, 54, which is preferably suppressed. Therefore, the sensor 62 is positioned such that magnetic noise is minimized, as shown in FIG. 5. This is discussed further, infra.

Note that the actuation force is usable only when the position of the magnet (facing the coil) is stabilized by the torque. Otherwise, the induced torque tends to flip the magnet. With two coils, the magnet will always be attracted by one of the coils and be drawn to it in a stable configuration. The use of two coils also significantly improves the efficiency of actuation.

Second, double chambers are employed. As the pump has two opposing coils, it is possible to use a double-chambered architecture with the coils providing symmetric forces instead of the classical single-chamber configuration. This permits the exploitation of both directions of membrane travel, and hence, allows for a nearly continuous output flow.

Third, dual magnets are used. Double chamber designs inherently favor symmetric components. A thin membrane with a single magnet on each side has been selected as a chamber divider and actuation system. This not only provides a symmetric feature but also eases the assembly process by allowing the magnets to be attached to the membrane and held in place by their own magnetic attraction alone. Furthermore, affixing the magnets to the outside of the membrane permits changes to be made to the sizes or shapes of the membrane and magnets independently.

The construction of the preferred embodiment facilitates disposability. As shown in FIG. 2, the system is constructed and arranged to have two, distinct, interworking parts. The reusable part contains the majority of components: the coils, sensor and electronics. The disposable part contains the fluid, valves, membrane and magnets; everything is sealed with the focus on cost reduction. There is no physical contact between the reusable section and the magnets (or the fluid).

Figure 6A:
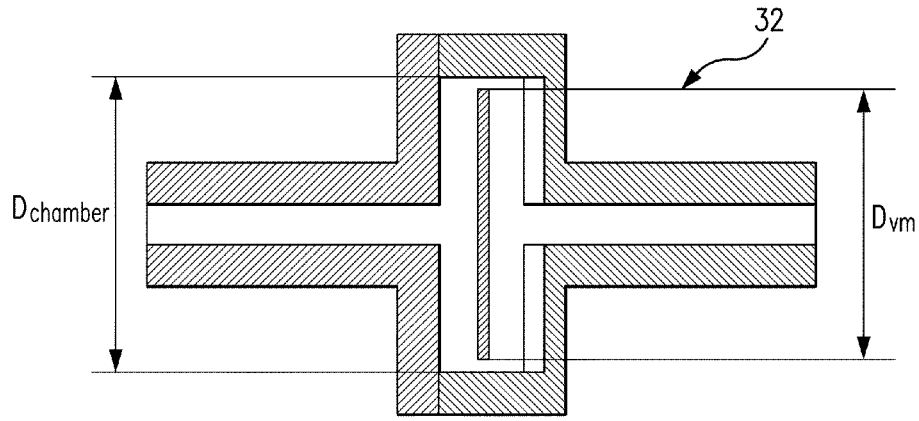
FIG. 6(a) is a schematic view of a portion of a preferred embodiment of a flow control system for a micropump illustrating a valve assembly thereof as disclosed herein.
Figure 6B:
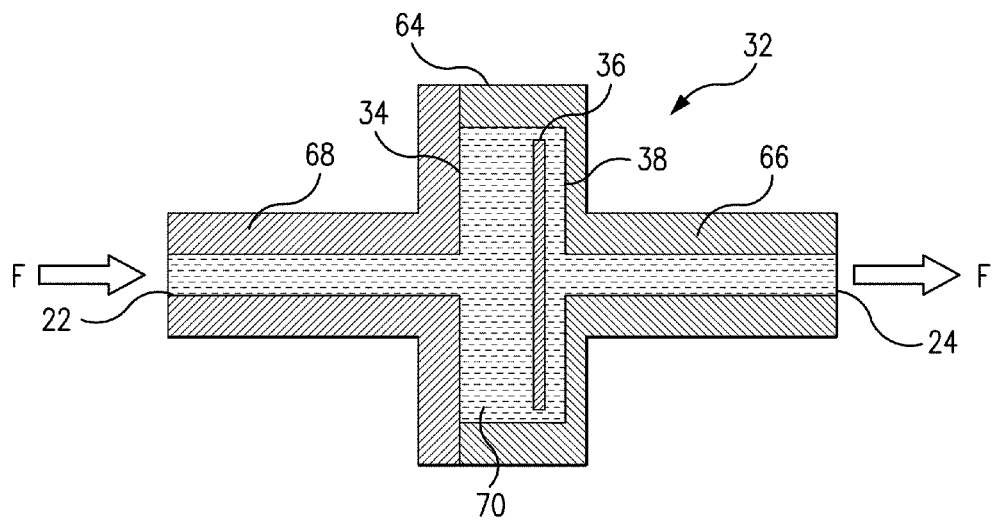
FIG. 6(b) is another schematic view of a portion of a preferred embodiment of a flow control system for a micropump illustrating a valve assembly thereof as disclosed herein.
Figure 6C:
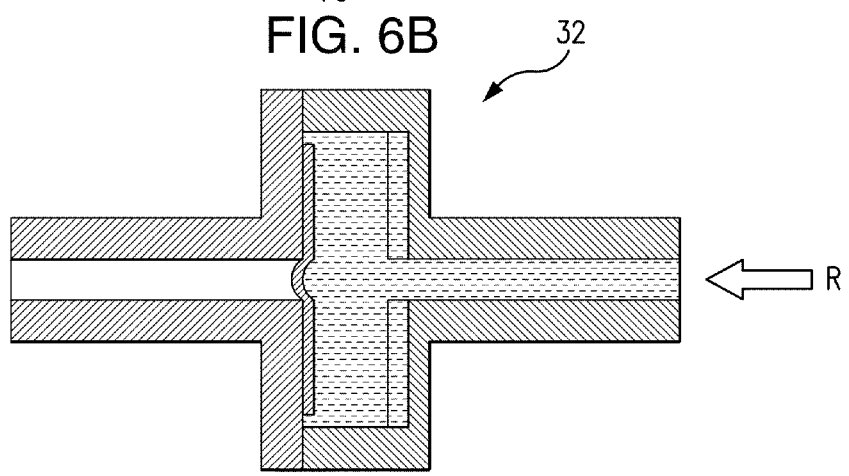
FIG. 6(c) is yet another schematic view of a portion of a preferred embodiment of a flow control system for a micropump illustrating a valve assembly thereof as disclosed herein.

Referring now to FIGS. 6 and 7, in a most simple embodiment, one-way flow assemblies 32 can be separately constructed apart from the other components of the micropump 10. These can then be positioned in the pump bodies in fluid communication with the chambers 20, 26. Ultimately, the one-way flow assemblies 32 are constructed and arranged to communicate with a reservoir of fluid to be pumped, e.g., a supply of insulin to be administered to a patient.

Referring now to FIG. 6, a schematic representation of the function of the one-way flow assemblies 32 is provided. Here, a one-way flow assembly 32 includes a housing 64, which may be formed from first and second housing components 66, 68 bonded together. Housing components 66, 68 define a generally cylindrically-shaped chamber 70 having a pair of generally flat, circular seating surfaces 34, 38 disposed apart and facing each other. These act as seats for the generally circular valve membrane 36 disposed within chamber 70.

The assembly 32 also includes an inlet 22 and an outlet 24 in fluid communication with the chamber 70. Valve membrane 36 is configured to float within chamber 70, and in a more preferred embodiment has a diameter, $D_{vm}$ approximately 80% of the diameter, $D_{chamber}$ of chamber 70.

Supply side seating surface 34, positioned adjacent inlet 22, is substantially solid. Thus, when the valve membrane 36 is in substantially seated contact with the supply side seating surface 34, fluid flow is stopped.

Referring now again to FIG. 6, whenever there exists a fluid pressure at the outlet 24, $P_{outlet}$, that is greater than the fluid pressure at the inlet 22, $P_{inlet}$, reverse fluid flow conditions will develop as shown in FIG. 6 (bottom figure) by arrow R. This reverse flow acts to sweep the valve membrane 36 towards the supply side seating surface 34. After the valve membrane 36 is seated against the supply side seating surface 34, the valve membrane 36 covers the inlet 22, substantially preventing reverse flow.

Looking in greater detail at the discharge side seating surface 38 as shown in FIG. 7, more detail is apparent.

Rather than being completely flat, the discharge side seating surface 38 shown thereby has pie-shaped raised plateaus 74 alternately disposed to thereon, intermittently separated by pie-shaped recesses 76. The outer edges of the pie-shaped recesses 76 extend beyond the diameter of the seated valve membrane 36 and their inner edges feed into the outlet 24. The fluid then can pass around the membrane 36 and through these pie-shaped recesses 76, thereby flowing through the outlet 24 in the forward fluid flow F direction. These plateaus 74 and recesses 76 provide a mechanism facilitating fluid flow while the valve membrane 36 is seated against the pie-shaped raised plateaus 74 disposed upon discharge side seating surface 38. In a more preferred configuration, there are four sets of alternating raised plateaus 74 and recesses 76, however any number that allows substantially unimpeded flow through the one-way flow assembly 32 while the valve membrane is seated against discharge seating surface 36 is acceptable.

Therefore, at any point where there exists fluid pressure at the inlet 22, $P_{inlet}$, that is greater than the fluid pressure at the outlet 24, $P_{outlet}$, forward fluid flow conditions will develop as shown by arrows F in FIG. 6 (middle figure). This forward flow sweeps the valve membrane 36 towards the discharge side seating surface 38, where it seats against the pie-shaped raised plateaus 74. Because the discharge side seating surface 38 contains pie-shaped recesses 76 that feed into outlet 24, fluid is allowed to flow around the valve membrane 36, through these recesses 76 and through outlet 24.

Figure 8A:
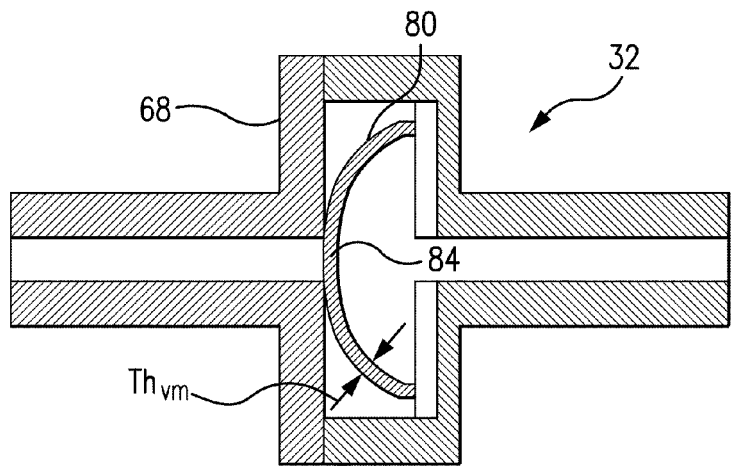
FIG. 8(a) is a schematic view of another portion of a preferred embodiment of a flow control system for a micropump illustrating a valve assembly thereof as disclosed herein.
Figure 8B:
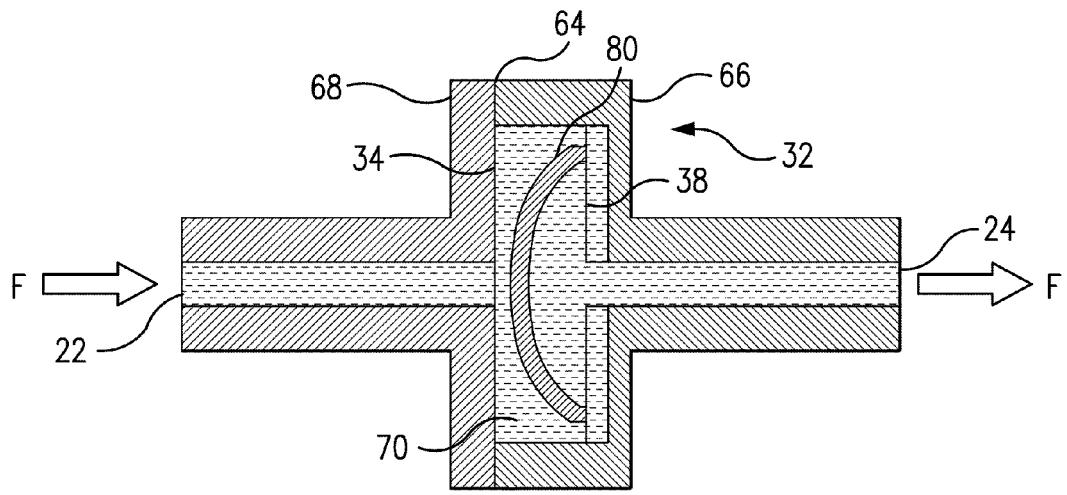
FIG. 8(b) is another schematic view of another portion of a preferred embodiment of a flow control system for a micropump illustrating a valve assembly thereof as disclosed herein.
Figure 8C:
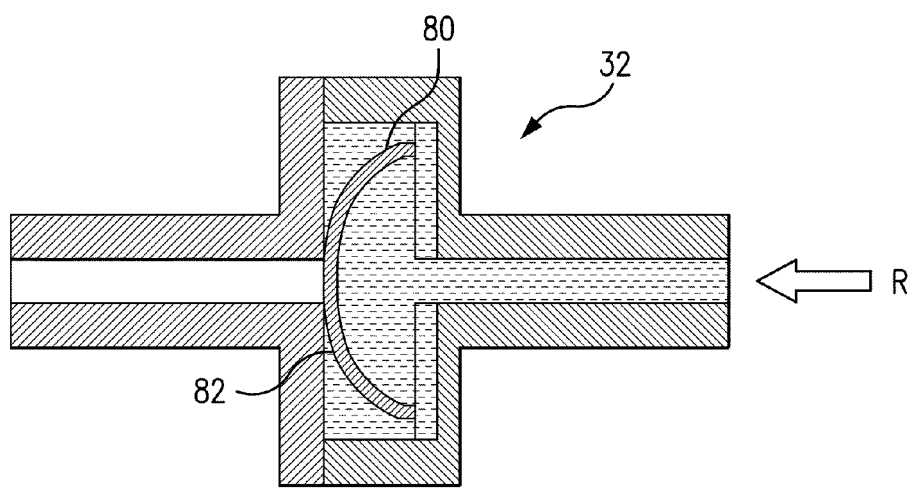
FIG. 8(c) is yet another schematic view of another portion of a preferred embodiment of a flow control system for a micropump illustrating a valve assembly thereof as disclosed herein.

Referring now to FIG. 8, an alternative, preferred embodiment for a valve membrane assembly 80 is shown. One-way flow is achieved in a somewhat similar fashion as that previously described, but specific design characteristics of the alternative embodiment valve membrane assembly 80 provide additional benefits. As before, the one-way flow assemblies 32 can be separately constructed apart from the other components of the micropump 10. These can then be positioned in the pump bodies in fluid communication with the chambers 20, 26. Ultimately, the one-way flow assemblies 32 are constructed and arranged to communicate with a reservoir of fluid to be pumped, e.g., a supply of insulin to be administered to a patient.

As before, a one-way flow assembly 32 includes a housing 64, which may be formed from a first and second housing component 66, 68 bonded together. Housing components 66, 68 define a generally cylindrically-shaped chamber 70 having a pair of generally flat, circular seating surfaces 34, 38 disposed apart and facing each other. These act as seats for the valve membrane assembly 80 disposed within chamber 70.

Figure 15:
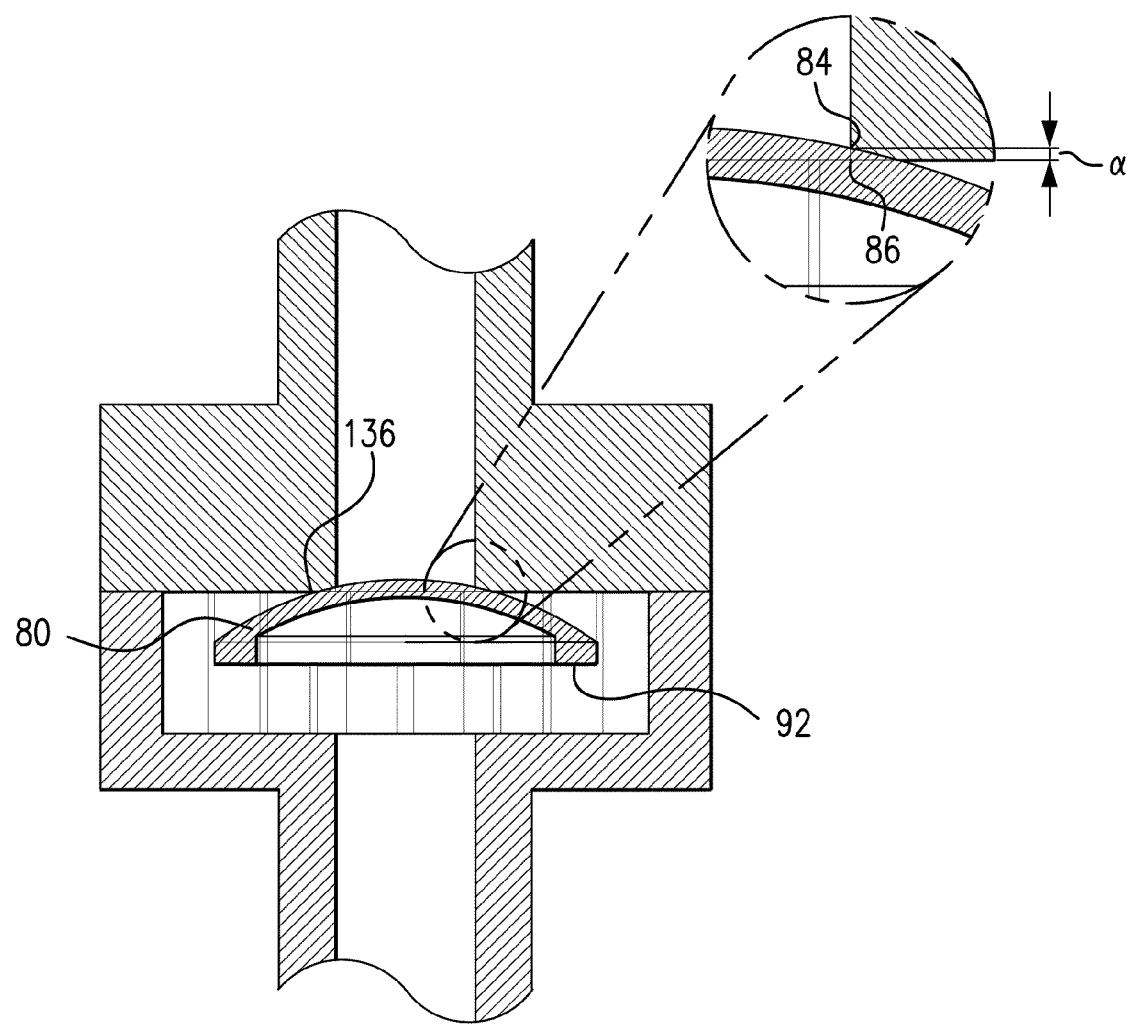
FIG. 15 is a cross-sectional view of a of a portion of a preferred embodiment of a flow control system for a micropump as disclosed herein.

In contrast with the earlier description, in FIG. 8, the valve membrane assembly 80 has a generally domed portion 82 having a spherical radius of curvature $R_{vm}$ and a nominal thickness of $Th_{vm}$. As further shown in the top portion of FIG. 8, the valve membrane assembly 80 is compressed somewhat during assembly of the two housing components 66, 68. It is this initial compression that is referred to herein as "pre-stressed." The effect of this arrangement is to preload the bias of the valve membrane assembly 80 against the supply side seating surface 34 and, due to its spherical shape, press a contact surface portion 84 of the valve membrane assembly 80 against the circular terminus 86 of the inlet 22, thereby sealing it against fluid flow (this is shown more fully in FIG. 15). As shown in FIG. 15, there is a preselected deflection a designed into the pre-stressed membrane. In the preferred embodiments described herein, a is equal to 0.002 inches. Because of its biased contact with the inlet 22, the pre-stressed valve membrane assembly 80 is constructed and arranged to require a finite amount of fluid pressure differential to be necessary before movement of the membrane assembly 80 away from the inlet 22 is effected. This finite amount of pressure is hereby referred to as the cracking pressure, $P_{cracking}$.

Consequently, reverse flow conditions are much less likely to occur. Rather than permitting reverse flow conditions to arise whenever fluid pressure at the outlet 24, $P_{outlet}$, is greater than the fluid pressure at the inlet 22, $P_{inlet}$, the valve membrane assembly 80 is already seated against the inlet 22 and biased to stay that way, even more substantially preventing reverse flow.

Indeed, a greater pressure differential is now required for flow to occur in the desired direction. Flow cannot occur until the sum of (a) the fluid pressure at the inlet 22, $P_{inlet}$, plus (b) the cracking pressure, $P_{cracking}$, is greater than (c) the fluid pressure at the outlet 24, $P_{outlet}$. Only then will forward fluid flow conditions develop, as shown by arrows F in FIG. 8 (middle figure). This forward flow moves the valve membrane assembly 80 from its biased position towards the discharge surface seating surface 38. Because the discharge surface seating surface 38 is constructed and arranged to permit fluid flow around the valve membrane, fluid flows around the valve membrane assembly 80, thereby flowing through the outlet 24 in the forward fluid flow F direction.

Figure 9A:
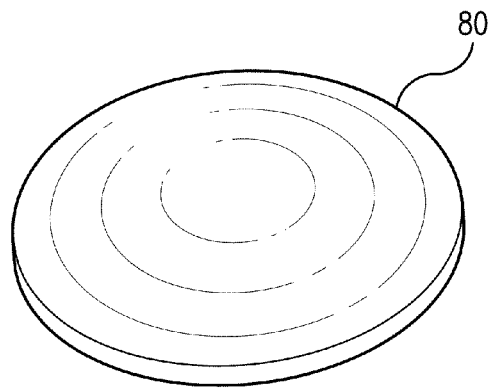
FIG. 9(a) is a top plan view of a portion of a preferred embodiment of a membrane for use with a flow control system for a micropump as disclosed herein.
Figure 9B:
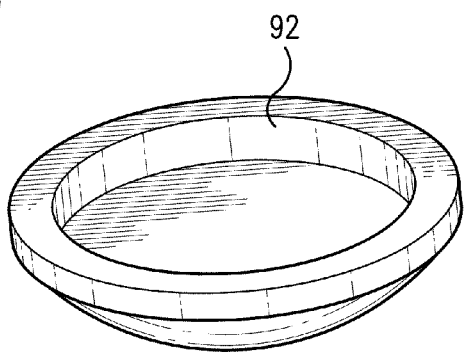
FIG. 9(b) is a bottom plan view of a portion of a preferred embodiment of a membrane for use with a flow control system for a micropump as disclosed herein.
Figure 10:
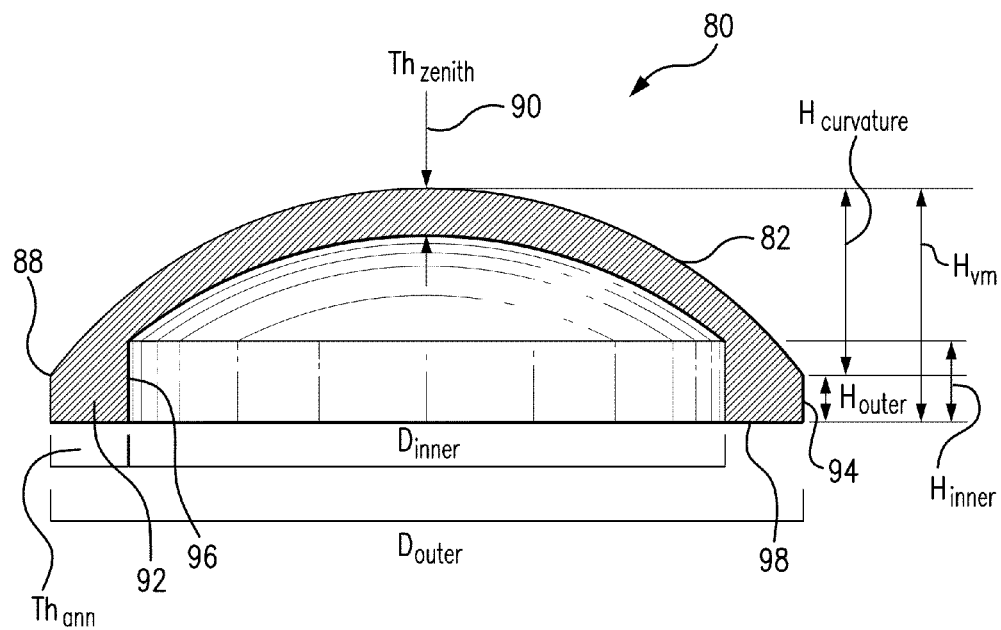
FIG. 10 is a cross-sectional view of the portion of a preferred embodiment shown in FIG. 9.

Referring now to FIGS. 9 and 10, more detail about a more preferred valve membrane assembly 80 is shown. The domed portion 82 has a spherical radius of curvature $R_{vm}$ and further has a thickness $Th_{dome}$. It is understood that the domed portion 82 could be provided with an outer radius of curvature and an inner radius of curvature, thereby yielding a more varying thickness. Extensive experimentation and computer modeling of fluid flow and valve membrane mechanical properties was done to determine optimum radii of curvatures for inner and outer portions of the domed hemisphere. In the preferred embodiment, however, the optimum radii of curvature for best combination of fast membrane response, reliable valve sealing and controllable fluid flow were selected to be the same and therefore the thickness of the valve membrane 80 varies as this selection would yield; i.e., thinnest near the reinforcement annulus 92 and thickest at the zenith 90. This thickness at the zenith 90 is $Th_{zenith}$.

The domed portion 82 is generally shaped as a portion of a sphere that has been intersected or cut by a plane, thereby defining a circular periphery 88 and having a dome zenith 90 located at the point on the dome that is equidistant from all points on the circular periphery 88. It is understood that any curved surface that terminates along a plane would have a generally circular periphery 88 and a zenith 90, regardless of whether the surface curvature precisely adhered to the contours of a sphere or was more ellipsoidal in its shape.

In a most preferred embodiment, the valve membrane assembly 80 has a reinforcement annulus 92 extending from the domed portion 82. As shown cross-sectionally in FIG. 10, the reinforcement annulus 88 has a unique shape. On its outer periphery, it presents a cylindrical outer surface 94 having a cylinder height $H_{outer}$ and a diameter $D_{outer}$. It presents a cylindrical inner surface 96 having a cylinder height $H_{inner}$ and a diameter $D_{inner}$. Its bottom terminus 98 is generally ring-like in contour and flat, having a thickness $Th_{ann}$ equal to one-half of $D_{outer}$ minus $D_{inner}$.

Viewed as in FIG. 10, the valve membrane assembly 80 has a working height $H_{vm}$ measured vertically from the dome zenith 90 to the bottom terminus 98, and has a curvature height $H_{curvature}$ measured vertically from the dome zenith 90 to the circular periphery 88.

Specific dimensions of preferred embodiments can be given using the variables defined above. Thus, for three examples, preferred dimensions are as follows (all units given in inches):

| Nominal Valve Size | ¼ inch valve membrane | 3/16 inch valve membrane | 3/16 inch valve membrane |
|---|---|---|---|
| $D_{outer}$ | 0.2500 | 0.1875 | 0.1875 |
| $D_{inner}$ | 0.2000 | 0.1475 | 0.1475 |
| $R_{curvature}$ | 0.1563 | 0.1250 | 0.1563 |
| $H_{outer}$ | 0.0150 | 0.0100 | 0.0100 |
| $H_{inner}$ | 0.0265 | 0.0150 | 0.0128 |
| $H_{curvature}$ | 0.0625 | 0.0423 | 0.0313 |
| $H_{vm}$ | 0.0775 | 0.0573 | 0.0413 |
| $Th_{annulus}$ | 0.0250 | 0.0200 | 0.0200 |
| $Th_{zenith}$ | 0.0150 | 0.0100 | 0.0100 |

Figure 11A:
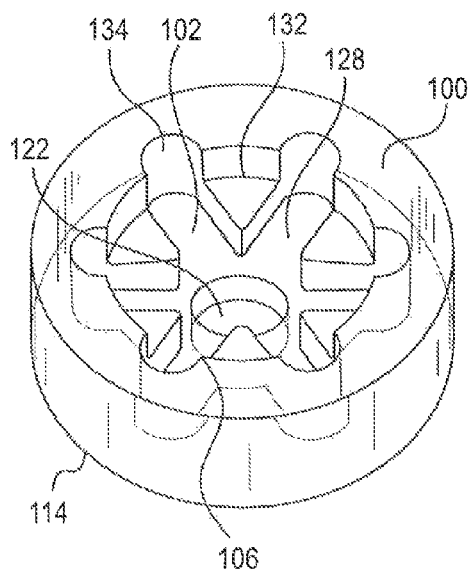
FIGS. 11(a) and (b) are top and bottom views, respectively, of a preferred embodiment of a membrane housing for use with a flow control system for a micropump as disclosed herein.
Figure 11B:
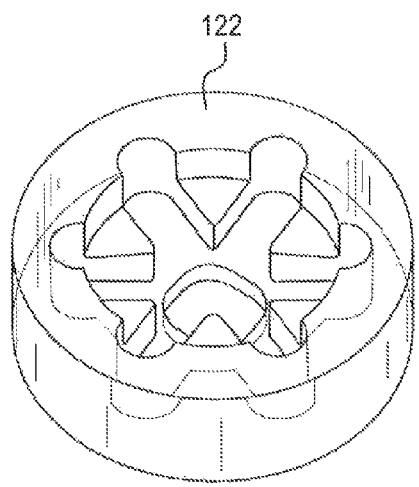
Figure 12A:
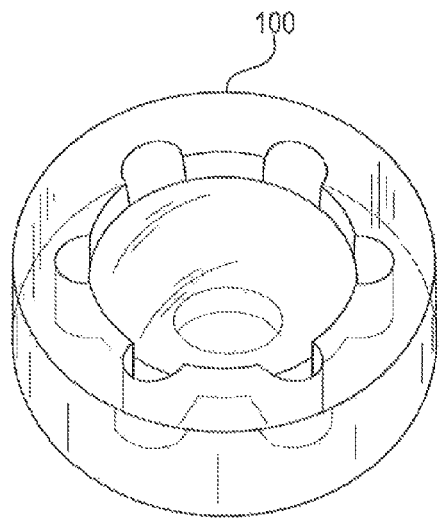
FIGS. 12(a) and (b) are top and bottom views, respectively, of the preferred embodiment shown in FIGS. 11(a) and 11(b) as fitted with a preferred embodiment of a membrane as disclosed herein for use with a flow control system for a micropump.
Figure 12B:
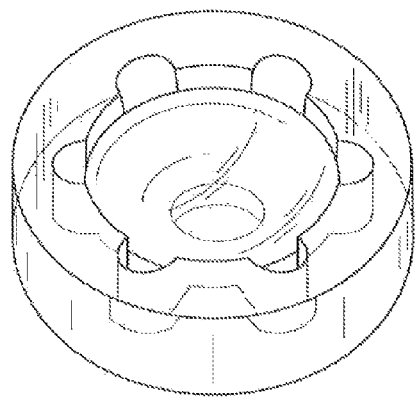
Figure 13A:
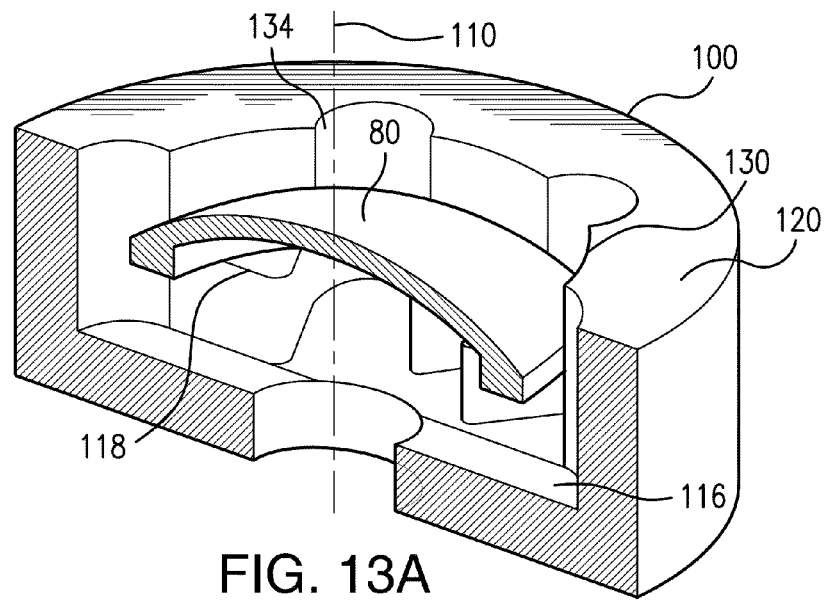
FIG. 13(a) is a cutaway illustration of the preferred embodiment shown in FIG. 12.
Figure 13B:
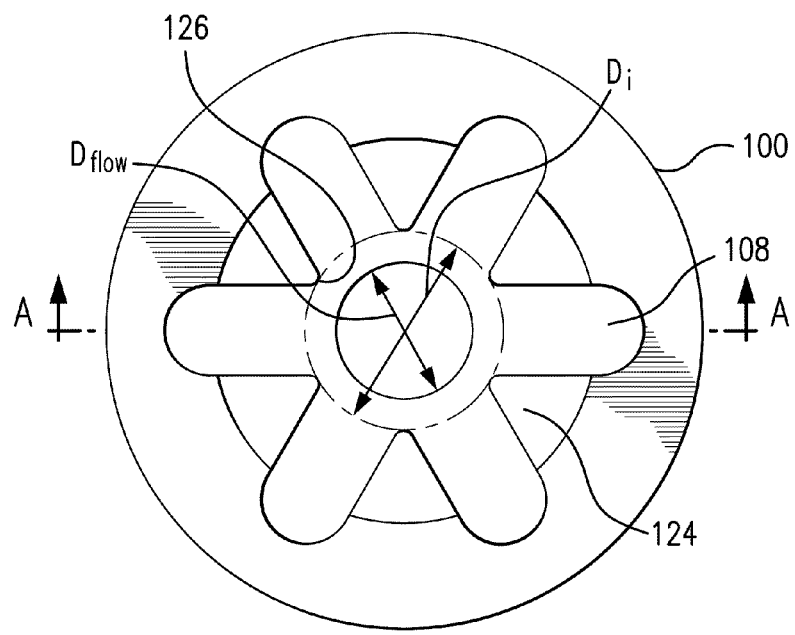
FIG. 13(b) is a top plan, schematic view of the preferred embodiment shown in FIG. 12.

Referring now to FIGS. 11 through 13, a more preferred embodiment of a discharge side seating assembly 100 is shown. The seating assembly 100 is separately constructed and arranged to receive a membrane assembly 80 (FIG. 11 shows an image of the seating assembly 100 on the left and a photograph of a seating assembly on the right). FIG. 12 illustrates the seating assembly 100 having a membrane assembly 80 inserted in place (FIG. 12 shows an image of the seating assembly 100 with the valve membrane assembly 80 seated therein on the left and a photograph of the same on the right). FIG. 13A illustrates a cross-sectional view of the seating assembly 100 with the membrane assembly 80 in place. FIG. 13B illustrates a top plan schematic view of the seating assembly 100 depicted in FIG. 12, without the membrane assembly 80 inserted in place. FIG. 13 C illustrates a schematic cutaway illustration of the preferred embodiment of the seating assembly 100 taken along the line A-A.

The seating assembly is provided with a more preferred arrangement of flow channels 102. As shown, there are six flow channels 102 and a seating surface 104 having an outer confine 106 thereabout. Semicircular flow passage spaces 108 extend radially outwardly from the axis 110 of the seating assembly 100.

Examining FIGS. 11 through 13 in more detail, it can be seen that the specific geometry is as follows. The overall outer shape of the seating assembly is that of a short cylinder having an axis 110, a top face 112 and a bottom face 114. Although the preferred embodiment is machined as a single piece, the seating assembly 100 can be described as having three layers 116, 118 and 120 each having a distinct radial profile and each sharing the same cylindrical outer wall.

First layer 116 has as its lower terminus the bottom face 114 of the assembly 100. First layer 116 is generally disc shaped and solid but for a center aperture 122 having a flow diameter $D_{flow}$ provided to facilitate fluid flow therethrough.

Second layer 118 overlays the first layer 116. Six generally pie-shaped, support surfaces 124 each extend radially inwardly in spaced apart relation, and each support surface 124 has an inner terminus 126. The inner termini 126 are equidistant from the axis 110 and thereby define an inner support diameter $D_i$. The inner support diameter $D_i$ is greater than the flow diameter $D_{flow}$ of the center aperture 122. It is understood that seating assembly 100 is sized particularly to fit valve assembly 80. Thus, the inner support diameter, $D_i$ must, at minimum, extend far enough to support the bottom terminus 98 of valve assembly 80. Therefore the maximum value for $D_i$ is equal to $D_{inner}$ shown in FIG. 10, of the particular valve assembly 80, that the discharge side seating surface 100 is intended to fit. The spaced apart relation of the support surfaces 124 defines six flow channels 128 therebetween. Extending outwardly from each flow channel 128 is a semicircular flow passage space 130.

Third layer 120 overlays second layer 118 and has as its upper terminus the top face 112 of the assembly 100. Third layer 120 has a generally disc-like, radial profile having an inner diameter boundary 132 that provides an outer confine 106 for a valve membrane. Extending outwardly from the inner diameter boundary 132 are six semicircular flow passage spaces 134, configured to align in axial profile with the semicircular flow passage spaces 130 of the second layer.

As thus configured, a pre-stressed valve membrane 80 for a micropump 10 with dynamic conforming flow assemblies 32 is disclosed. As used herein the valve membrane 80 is referred to as pre-stressed because there is an initial loading placed on the valve membrane 80 during assembly within the flow assembly 32. This is caused by the initial deflection of the domed shape of the valve membrane 80 that is created when the inlet terminus 86 (shown in FIG. 8) comes in contact with the contact surface portion 84 of the valve membrane 80. In a most preferred embodiment, the inlet termini 86 are micro-polished to provide a more secure valve seal.

A flow assembly seat depth is selected to provide optimum operational characteristics. The height of the valve seat is selected to be slightly less than the height of the valve membrane. The difference produces the pre-stressed effect (i.e. [Height of valve membrane]−[Height of valve seat]=[Interference distance]). The actual formula is however slightly more complicated since the formation of the port hole itself reduces the interference distance slightly as a result of the modified geometry. The domed, partially deflected, pre-stressed valve membrane 80 is geometrically formed from two offset spherical sections having the same radii of curvature, as discussed infra., producing a longitudinally non-uniform thickness.

This may be conceptually illustrated by comparing the spherical section of the valve membrane to the Northern hemisphere of the Earth. If one orients the North-pole to coincide with the highest point on the valve membrane (i.e. the center of the contact surface), the lines of longitude extend radially from this point. If one measures the membrane thickness along this line, one finds that the thickness changes continuously along the path, viz., the thickness of the contact surface is greater than the thickness of the medial-lateral sidewalls and is continuously variable along the entire length.

The membrane's non-uniform thickness and its base lead to the classification of three geometrically distinct regions (shown in FIG. 15): the contact surface 84, medial-lateral sidewalls 136 and the valve membrane base or lip 92.

The pre-stressed valve membranes 80 are preferably elastically deformable but still sufficiently stiff to provide quick closure times in operation. Preferably, the valve membranes 80 possess sufficient strength to support the reverse flow backpressures experienced in the operation of the micropump 10. Moreover, the valve membranes 80 are preferably biologically compatible, so that they can be used in connection with medical devices.

Performance during flow conditions operates as follows. In reverse flow conditions, the contact surface 84 mates with the inlet terminus 86. During this contact, the membrane 80 conforms to the inlet terminus 86 to ensure that the passageway for fluid is completely blocked. The thickness of the contact surface 84 relative to the thickness of the medial-lateral surfaces, or sidewalls, 136 aids the membrane 80 in withstanding reverse flow pressures. The relatively thicker contact surface 84 can facilitate better support across the inlet 22 than a thinner membrane could, and therefore can withstand larger pressure differentials.

In forward flow conditions, the medial-lateral surfaces 136 deform inward, allowing the contact surface 84 to maintain a smooth domed shape which minimizes surface friction. This ultimately leads to reduced back pressure. The sidewall deformation results in a change of height between the contact surface 84 and the inlet terminus 86, which opens a path for fluid flow.

The relative thickness of the medial-lateral sidewall 136 defines the working deformation for a given fluid flow. A relatively thin sidewall allows for low cracking and low back pressure. A relatively thick sidewall provides faster response time but results in a greater pressure drop across the valve.

The cracking pressure is directly related to both the pre-stressed force and the thickness of the medial-lateral walls. These walls essentially function as soft springs for supporting the contact surface. Increasing either the pre-stressed force or the wall thickness increases the cracking pressure but also enhances the frequency response; the converse is also true.

The membrane lip is provided as a thickened region at the base of the membrane. Its increased thickness forms a stiffer, more rigid base to help span the fluid channels without deforming. This helps to maintain the initial pre-stressed force throughout the lifespan of the valve. Mechanical stability and overall rigidity of the membrane is also improved by the lip which allows the membrane to maintain its spherical sectioned form even when freestanding. During operation, maintaining the integrity of the spherical shape insures balanced force distribution which yields smooth deformations and optimized surface flow.

The increased strength of the lip eliminates tearing or cracking of the membrane edge both during manufacturing as well as in operation. This increases manufacturing throughput and improves membrane lifespan.

The rigid flat base provided by the membrane lip also provides consistency in pre-stressing the membranes. The increased dimensional uniformity allows for an exact height of 0.0413 inches to be established. This provides a very precise pre-stressed load when used in conjunction with proper valve seat depth of 0.035 inches, labeled $H_{vs}$ on FIG. 13(c).

Optimizing the membrane's cross-sectional profile requires consideration of various competing factors. Through computer simulations as well as hands-on testing, dimensional changes were found to enhance one property and simultaneously adversely affect another. For example, increasing the thickness of the membrane improves the frequency response but adversely affects the cracking pressure, the induced channel cross-section, and the back pressure. Continuing study and an undue amount of modeling and experimentation led to the selection of the following parameters for a preferred embodiment.

More generally, it was determined that the following preferred ratios provide superior results: (a) a ratio of 6:5 for the thickness of the contact surface to the thickness of the medial-lateral sidewalls; (b) a ratio of 10:1 for the diameter of the membrane to the width of the membrane lip; (c) a ratio of 6:5 for the diameter of the membrane to the radius of curvature of the membrane; and (d) a ratio of 1:1 for the thickness of the contact surface to the height of the membrane lip.

Referring now to the structure of the valve body, a multi-channel membrane housing is disclosed. The channels in the valve housing are incorporated to provide a path for fluid to flow around the membrane in the forward biased condition, i.e. when the valve is open and fluid is flowing.

The channels are configured as follows. First, they preferably extend radially beyond the valve seat so as to permit the fluid to flow around the membrane. Next, the width of the channels should be minimized to reduce the distance which must be spanned by the membrane lip. Further, the sum of the cross-sectional areas of the portion of the channels that extend beyond the valve seat must be greater than or equal to each of the cross-sectional areas of the inlet and outlet tubes. Additionally, turbulence should be minimized wherever possible to reduce induced back-pressure. One preferred embodiment which satisfies these requirements is depicted in FIGS. 11, and 13.

Referring now to the characteristics of a preferred valve seat, the valve seat is configured to house the membrane, keep it centered, and define the pre-stressed load. FIG. 12 depicts the valve membrane housed in the valve seat and shows how the membrane is axially centered. FIG. 13 depicts a cross-sectional view of the membrane and illustrates the membrane lip in contact with the valve seat.

Figure 14:
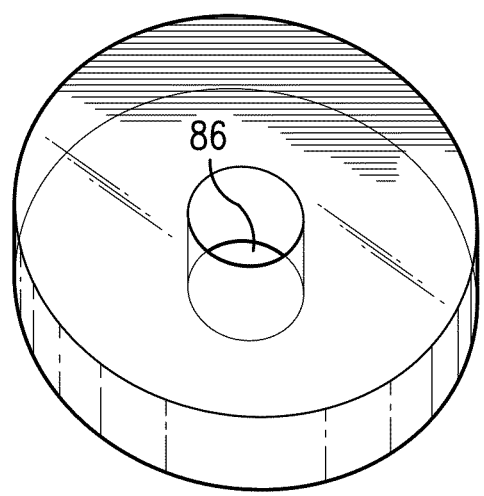
FIG. 14 is a top plan view of a portion of a preferred embodiment of a valve cover for use with a flow control system for a micropump as disclosed herein.

The valve assembly is provided with a micro-polished valve seal at the inlet terminus 86, shown in FIG. 14. The membrane conforms to the valve seal at the inlet terminus to ensure that the passageway for fluid is completely blocked; however, in order for this conformity to occur for small back-pressures, the valve seal at the inlet terminus on the body of the check valve must be very smooth. Therefore, it is helpful to be precise in manufacturing. Simply producing these parts using conventional machining techniques, such as carefully drilling the port hole, may not be sufficient to produce a defect-free surface, particularly at the sizes used in the preferred embodiment. Therefore, after drilling, the valve seals were micro-polished to a tolerance of 0.002 inches.

Referring now to the complete valve assembly, a flow analysis was performed to assess the membrane deflection in relation to the fluid velocity and changes in pressure. Wall thickness and channel dimensions were optimized to obtain desired performance.

Figure 13C:
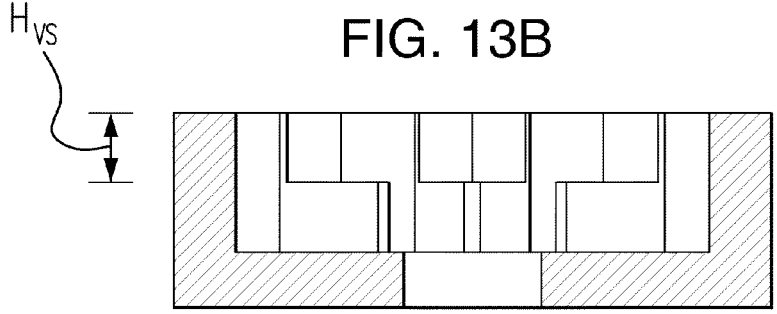
FIG. 13(c) is a schematic, cutaway illustration of the preferred embodiment shown in FIG. 13(b) taken along the line A-A.

To determine the desired pre-stressed load given the height of the valve membrane—dimension labeled $H_{vm}$ in FIG. 10, the valve seat height—dimension labeled $H_{vs}$ in FIG. 13(c) was selected to provide an interference fit between the membrane contact area and the valve cover seal. This interference fit is the difference between $H_{vm}$ and the slightly smaller $H_{vs}$. The magnitude of this interference is directly related to the pre-stressed force of the membrane. This distance is typically on the order of just a few thousandths of an inch, illustrated in FIG. 11.

During assembly, as the valve cover is mounted to the multi-channeled membrane housing, the interference causes the membrane to be compressed, which biases the valve in the closed position. The depth of the valve seat can be increased to reduce the cracking pressure. This will, however, reduce the pre-load force and the frequency response of the valve.

To determine the performance of the prototype, the cracking pressure was experimentally determined by slowly increasing the height of a water column until flow through the valve began. The height of the meniscus was then converted to a pressure using the known gravity and the density of the fluid.

To assess membrane deformation, the discrete check valve body was formed from a clear polymer, thereby permitting visual observation of the membrane deformation and dynamic behavior. By using a high speed camera, it was confirmed that the membrane lip/base stayed in contact with the valve seat while the membrane actively deformed to permit fluid flow.

The unique design of the valve membrane allows for precise fluidic flow control which would otherwise be difficult or impossible to achieve with a passive valve system. The exceptional characteristics of these dynamically conforming valves can largely be attributed to the implementation of a multi-channeled membrane housing, a customizable valve seat depth, and a domed, pre-stressed membrane. The domed, pre-stressed membrane provides a better seal, reduces stiction, minimizes backpressure, enhances the frequency response, and provides a means for obtaining diminished cracking pressures. The unique geometries yield a final prototype which is both small and compact making it suitable for embedded designs, permitting further reduction in the overall size of a given micropump.

Referring now to FIGS. 16 through 19, a mold 140 is disclosed for manufacturing the valve membrane 80. As shown, the mold 140 has three pieces; an upper portion 142, a lower portion 144 and a mold sleeve 146. Additionally, a method of producing the mold 140 is disclosed herein.

Figure 16:
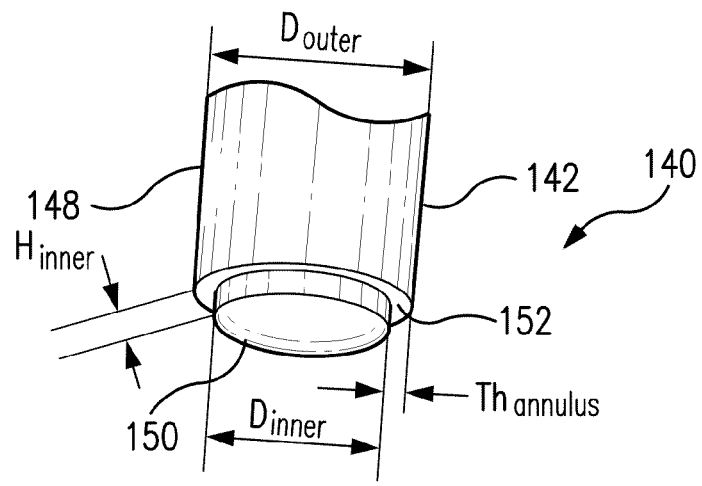
FIG. 16 is a plan perspective of the upper portion of a preferred embodiment of a mold for making a membrane for use with a flow control system for a micropump as disclosed herein.

Referring now to FIG. 16, the upper portion of the mold 142 is fabricated. Using a 1.7 inch long section of ¼ inch diameter aluminum round stock 148, a 5/16 inch diameter of curvature crown 150 was machined on one end using a lathe. Subsequently, a small notch 152 was carved out, 0.025 inches deep, along the edge where the crown 150 and the ¼ inch stock joined. The width of the notch 152 corresponds to the desired width of the reinforcing annulus of the valve membrane 80. The diameter of the rod corresponds to the outer diameter of the membrane 80. Finally, all surfaces were carefully polished to a mirror finish.

Figure 17:
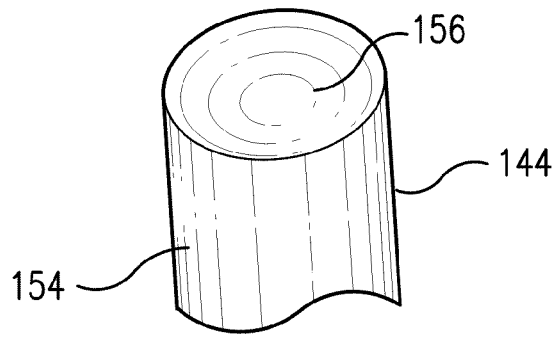
FIG. 17 is a plan perspective of a portion of the lower portion of a preferred embodiment of a mold for making a membrane for use with a flow control system for a micropump as disclosed herein.

Referring now to FIG. 17, the lower portion of the mold 144 is fabricated. Again using a 1.7 inch long section of ¼ inch diameter aluminum round stock 154, a 5/16 inch diameter of curvature concave dish 156 was machined on one end using a lathe. The dish 156 was roughed out using a ⁵⁄₁₆ inch ball end mill and then polished to a mirror finish.

Figure 18:
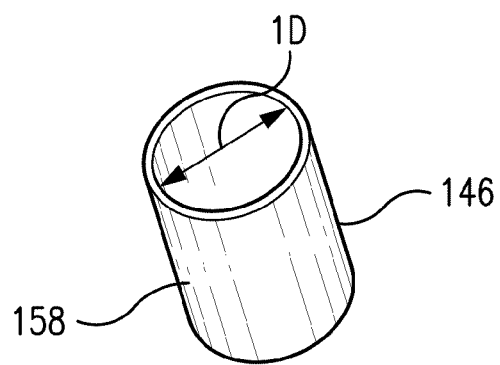
FIG. 18 is a plan perspective of a portion of a mold sleeve of a preferred embodiment of a mold for making a membrane for use with a flow control system for a micropump as disclosed herein.

Referring now to FIG. 18, the mold sleeve 146 is fabricated. The mold sleeve 146 was machined from an aluminum round 158 to have an interior diameter of ¼ inch so that it could precisely slide over the upper and lower mold portions 142, 144. The precise interior diameter was obtained using a 0.251 inch reamer, and subsequently polished to a mirror finish. See FIGS. 16-18. Thus, FIG. 16 illustrates the upper mold portion 142, FIG. 17 illustrates the lower mold portion 144 and FIG. 18 illustrates the mold sleeve 146 as produced and ready for fabricating valve membranes 80.

To prepare the materials used to create the membranes 80, the following protocol was followed. The valve membranes are produced from Sylgard 184 or Silastic Q7-4840, both made by Dow Corning Corporation. Experiments and modeling showed that these two materials perform similarly as valve membranes. This description specifies Sylgard 184, but is not intended to imply that it is the only PDMS material that makes an acceptable valve membrane. The Sylgard 184 is mixed in a ratio of 10:1 (base-to-reagent). If using Silastic Q7-4840, the A and B components are mixed in a ratio of 1:1. After mixing, the Sylgard (or Silastic) stock is left to sit for 10 minutes to allow air bubbles to exit the surface.

Fabrication is performed as follows. The tooling 140 created as described above is configured in a vertically oriented, collinear manner with the ball/crowned portion 150 above the concave portion 156. The upper and lower halves 142, 144 of the mold 140 are separated and lubricated using silicone lubricant. A small amount, e.g. a single drop, of premixed/degassed Sylgard 184 or Silastic Q7-4840 is added to the concave portion 156 of the lower portion 144.

The sleeve 146 is moved down the shaft to cover the joint between the upper and lower half of the mold. The sleeve performs two functions. First, it prevents hot air used to heat the mold from "blowing" away any of the silicone before it is cured. This is helpful to minimize the formation of voids and function in the membrane. Second, it provides a consistent, uniform circular edge around the base of the membrane. This is necessary to precisely place the membrane in the valve seat while maintaining the proper pre-stressed interference dimensions.

The upper mold portion 142 is then dropped into the lower mold portion 144 until it is 0.005" short of its final intended position. Excess Sylgard 184 (or Silastic Q7-4840), which may squirt out the sides, is wiped from around the seam of the mold 140. The upper mold portion 142 is then dropped the remaining distance so that the two mold portions 142, 144 are separated the exact distance desired for the final membrane thickness, $Th_{zenith}$, typically 0.015 or 0.010 inches. The entire setup is then heated to 300° F. for 14 minutes for Sylgard 184 or, for Silastic Q7-4840 to 302° F. for 5 minutes using a heat gun. The setup is subsequently allowed to cool for 2 minutes.

At this point, the membrane 80 is removed and inspected as follows. After cooling, the sleeve 146 is removed and the two halves 142, 144 of the mold 140 are separated. The membrane 80 is then carefully peeled off of whichever portion 142, 144 of the mold 140 to which it is stuck.

The valve membrane 80 is consequently formed with a ring around its perimeter; this is the reinforcement annulus 92. This reinforcement annulus 92 was deliberately created for mechanical stability and is a result of the notch 152 machined into the upper half 144 of the mold 140. See FIG. 9, showing the pre-stressed membrane 80 top (left) and bottom (right), and FIG. 10, showing the cross-sectional view of the pre-stressed membrane 80. The specific architecture of the reinforcement annulus 92 is therefore dictated by the machining of the tool 140. Thus, if different dimensions to the reinforcement annulus 92 are desired, adjustments to the machining of the tool 140 are made accordingly.

Figure 19:
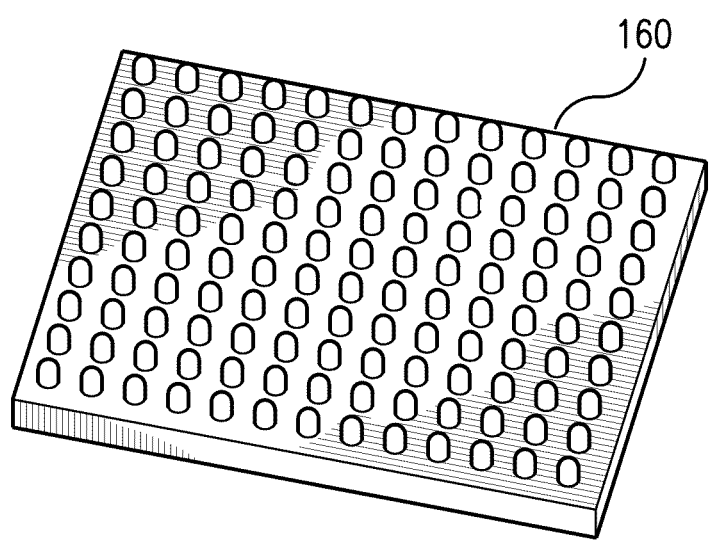
FIG. 19 is a top plan view of a portion of an alternative embodiment of a mold for making a membrane for use with a flow control system for a micropump as disclosed herein.

In mass production, different methods of manufacture are anticipated. This process can be mass produced by applying the concept of parallel processing, that is, if the bake time cannot be reduced, the way to increase throughput is to increase the number of pieces produced per bake cycle. Thus, a mass production mold 160 is required, as shown in FIG. 19.

Figure 20:
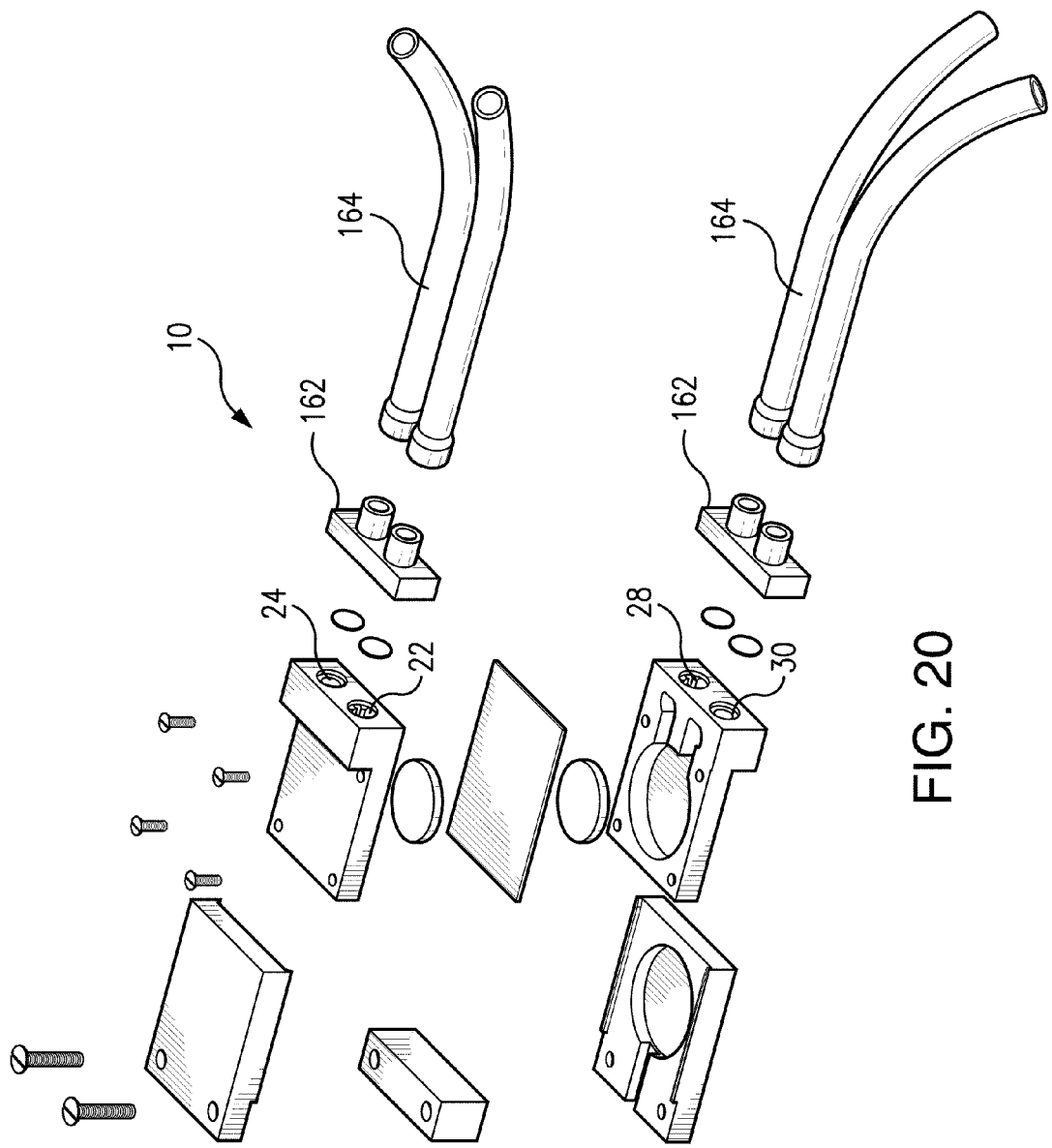
FIG. 20 is a perspective view of an exploded view of a portion of a preferred embodiment of a flow control system for a micropump as disclosed herein.
Figure 21:
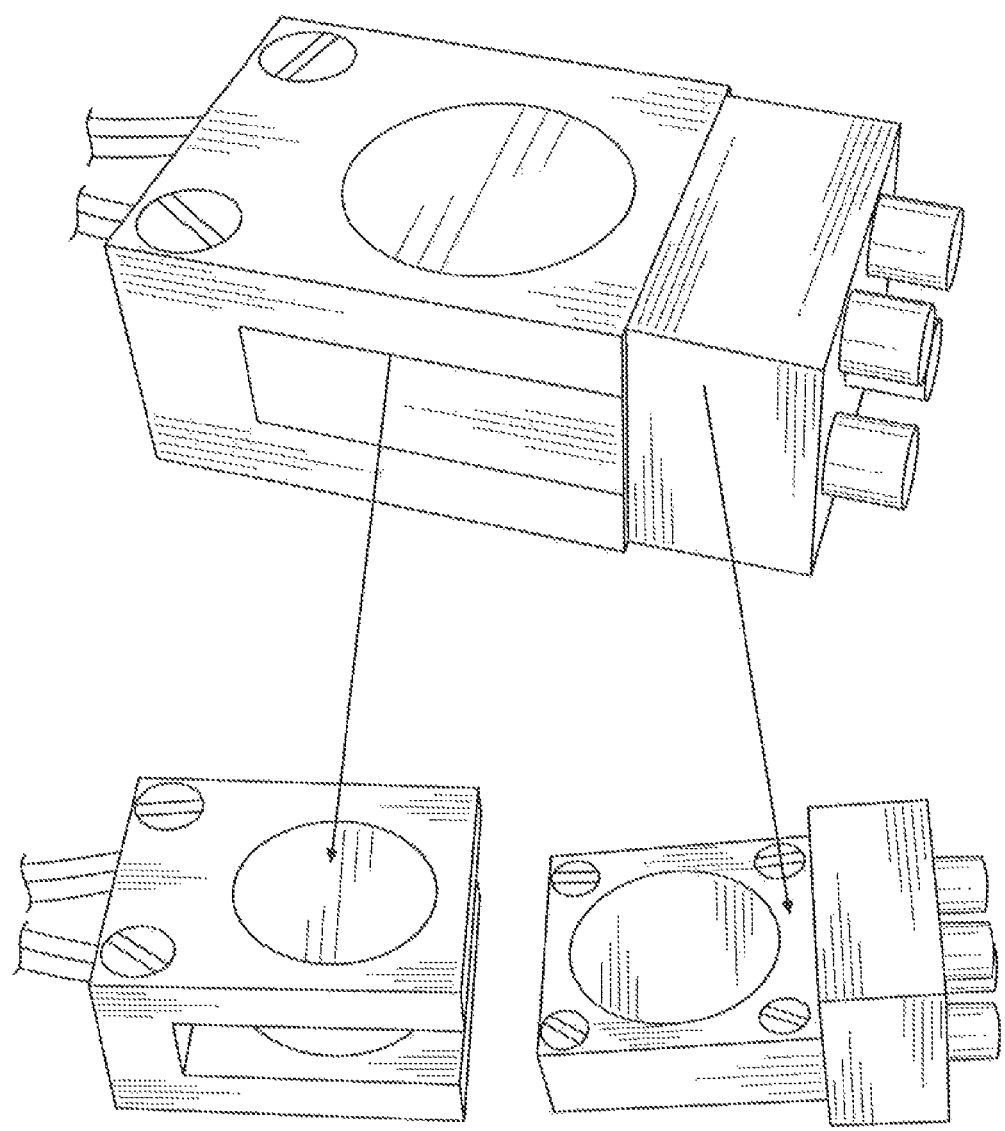
FIG. 21 is a photographic illustration of a preferred embodiment of a micropump illustrating the two-part construction thereof.

Referring now to FIGS. 20 and 21, the tooling and method of manufacture enables creation of an improved, disposable pump assembly 12 for use with a micropump 10 adaptable for use with a catheter (not shown). The pump inlets 22, 28 and outlets 24, 30 communicate with manifolds 162 sized to fit tubing 164 from the catheter (not shown).

Control electronics 166 are provided as shown in FIG. 22. As shown in the lower portion of the drawing, the circuit board 168 used with the micropump 10 (not shown) is sized to fit the micropump. As disclosed, the circuit board 168 is about 17 mm (about 0.67 inches) wide and about 26 mm (about 0.67 inches) long. In the center of FIG. 22, the soldering diagram is shown. An example circuit diagram is shown at the top of FIG. 22.

A description of the custom electronic driver circuit is as follows. The electronic driver circuit provides a mechanism for driving and controlling the micropump in a manner which allows for precise volumetric delivery of fluids. The circuit includes a dsPIC30F3012 microcontroller manufactured by Microchip which controls the operations and peripherals and simultaneously monitors the information obtained by the feedback sensors. While the microcontroller determines the timing and magnitude required to drive the pump coils, the actual power required by the pump can exceed the drive capabilities of the microcontroller itself. This problem is addressed by the addition of the Si9986 Buffered H-Bridge manufactured by Vishay Siliconix, which is capable of handling much higher drive currents and voltages (up to 1 Amp and 13.2 Volts). The circuit is also configured to regulate voltage levels, stabilize transients, and for signal conditioning.

The microcontroller firmware is provided with the custom operating system. The system monitors system parameters and makes real-time adjustments to keep the system in balance around the desired control point. The control scheme implemented is that of a proportional-integral-differential (PID) controller. The driver magnets' position feedback data is acquired using a linear Hall-effect sensor positioned in an offset position to minimize signal noise. This placement provided precise yet low-cost and contactless sensing, which in turn made possible separating the pump into a disposable pump-portion and a non-disposable electronic control system.

The preferred embodiment is battery powered; therefore overall efficiency is desired. To increase driver efficiency, the entire output is digital, including the H-Bridge. The signal is pulse-width modulated (PWM) internally within the microcontroller and fed to the inputs of the bridge. The PWM chop frequency is 50 kHz, a frequency well above the range of human hearing (thus ensuring the coils will not produce any audible noise) yet low enough so that the transistors are still within their efficient switching frequency range. Moreover, the microcontroller is put to sleep (i.e. in an ultra-low power state) whenever possible to eliminate unnecessary power consumption.

For external communication, a serial port interface was also incorporated within the design. This provided a versatile communication port which is compatible with a wide range of existing products and embeddable devices (such as wireless communication modules, PC data transfers and communication, additional sensors, etc.). By developing a PC-based graphical user interface, communication with the electronic driver circuit is provided, issuing commands and monitoring system performance. This permits enhanced testing, tuning, analysis, and demonstrations of pump performance.

A more plenary description of the theory, construction, operation and use of the preferred embodiment follows. As disclosed, the micropump includes actuation, valving, electronics, sensing and control. The architecture and electromagnetic pumping technology provided permits contactless sensing and actuation, which makes it possible to separate the pumping mechanism from the electronic and actuation components. Pump components are preferably fabricated using conventional techniques to reduce production costs, thereby making a disposable product economically more feasible. The micropump is capable of delivering very high flow rates (170 mL/min) and features closed-loop control for therapies requiring a precise volumetric dosage.

There is an increasing interest for embedded systems capable of handling small and precise volumes of fluids, such as in applications like drug delivery systems or µTAS (Micro Total Analysis System) implementations. A. Manz, N. Graber, and H. Widmer, "Miniaturized total chemical analysis systems: a novel concept of chemical sensing," *Sensors and Actuators B*, vol. 1, pp. 244-248, 1990. Micropumps are one of the main components of these systems and are often the limiting factor for size, weight and cost. For this purpose, a number of micropumps have been designed and fabricated utilizing a variety of different technologies.

These include commercial applications involving active micropumps, such as insulin delivery systems, are typically based on classical electrical motors in designs such as syringe pumps or peristaltic pumps. These designs are cost-effective, and trials have been performed to reduce their size. C. Koch, V. Remcho, and J. Ingle, "PDMS and tubing-based peristaltic micropumps with direct actuation," *Sensors and Actuators B*, vol. 135, pp. 664-670, 2009. However, the size of the electric motors which are necessary for delivering the desired forces prevents miniaturization below the 40-50 mm range. This severely limits the scope of applications to only large scale drug delivery systems.

Silicon-based MEMS micropumps have been used, mostly by employing piezoelectric actuation. H. van Lintel, F. V. de Pol, and S. Bouwstra, "A piezoelectric micropump based on micromachining of silicon," *Sensors and Actuators A*, vol. 15, p. 153-167, 1988; N. Nguyen, X. Huang and T. Chuan, "MEMS-micropumps: a review," *Journal of Fluids Engineering*, vol. 124, p. 384-392, 2002; A. Acevedo, *Creation of Dual Chamber Micropump Using Rapid Prototyping*, Milwaukee School of Engineering. However, the material cost of silicon and related fabrication issues burden its use.

Lower cost micropumps have been attempted using materials such as plastic, see, e.g., "Small, powerful, light, precise: micro diaphragm pumps made of plastics," March 2009, [online] http://www.thinxxs.com/main/produkte/micropumps.html; "Bartels micropumps," April 2009, [online] http://www.bartelsmikrotechnik.de/index.php/micropumps.html; and "Precision products," March 2009, [online] http://www.star-m.jp/eng/products/precision/index/html, PDMS or PDMS+PMMA, see, e.g., O. Jeong, S. Park, S. Yang, and J. Pak, "Fabrication of a peristaltic PDMS micropump," *Sensors and Actuators A*, vol. 123-124, pp. 453-458, 2005; C. Yamahata, C. Lotto, E. Al-Assaf, and M. Gijs, "A PMMA valveless micropump using electromagnetic actuation," *Microfluid Nanofluid*, vol. 1, pp. 197-207, 2005; and T. Pan, S. McDonald, E. Kai, and B. Ziaie, "A magnetically driven PDMS micropump with ball check-valves," *J. Micromech. Microeng*, vol. 15, pp. 1021-1026, 2005.

Efforts at disposability have been made. See, e.g., F. Trenkle, S. Haeberle, and R. Zengerle, "Normally-closed peristaltic micropump with re-usable actuator and disposable fluidic chip," Sensors and Actuators B 54, *Science Direct*, vol. 1, pp. 1515-1518, 2011; S. Ha, W. Cho, and Y. Ahn, "Disposable thermo-pneumatic micropump for bio lab-on-a-chip application," *Microelectronic Engineering*, vol. 86, pp. 1337-1339, 2009; and R. Irawan, S. Swaminathan, P. Aparajita, and S. Tjin, "Fabrication and performance testing of disposable micropump suitable for microfluidic chip," in *Intl. Conf. on Biomedical and Pharmaceutical Engineering*, Orchard Hotel, Singapore, December 2006, pp. 252-255. However, the PDMS pumps described are based on expensive microfabrication techniques, which require costly equipment that utilizes an inherently slow process. This limits the ability for manufacturers to mass-produce these types of pumps.

Some studies have focused specifically on reducing fabrication costs by utilizing clever polymer based designs which can be produced with standard fabrication techniques. In M. Zhu, P. Kirby, M. Wacklerle, M. Herz, and M. Richter, "Optimization design of multi-material micropump using finite element method," *Sensors and Actuators A*, vol. 149-1, pp. 130-135, 2009, piezoelectric actuation was used to supply up to 1.8 mL/min with 44×17×8 $mm^3$ pumps. In S. Bohm, W. Olthuis, and P. Bergveld, "A plastic micropump constructed with conventional techniques and materials," *Sensors and Actuators A*, vol. 77-3, pp. 223-228, 1999, both electromagnetic and piezoelectric actuators were used to supply up to 1.8 mL/min with a 10×10×8 $mm^3$ pump (electromagnetic version) and 2.1 mL/min with a 12×12×2 $mm^3$ pump (piezo version). They were successful in reducing manufacturing costs but not to the point desired for disposable systems. In the case of piezoelectric actuators, piezoelectric materials are expensive and they require high operating voltages. This requires the use of specialized, expensive, and bulky electronics, which is especially difficult to incorporate in embedded applications. In the case of electromagnetic actuators, an expensive and bulky coil is required inside the pump. In both cases, electrodes and supply wiring are needed in the pump body itself, which increases the volume and price of the pump.

For drug delivery and µTAS applications, disposable pumps would be especially desirable since it would eliminate the need for cleaning and sterilizing after each use and would decrease the risk of chemical impurities or biological contamination. Unfortunately, the relatively high cost of micropumps today prevents disposable use, which strongly limits the scope of their applications.

Another feature common to all of the aforementioned micropumps is an open-loop control system with flow rates dependent on the driving frequency alone. This often leads to a lack of reproducibility and a lack of flow rate predictability. As a result, the ability to supply precise flow rates and doses is severely impeded making them poorly suited for applications such as drug delivery.

In contrast, the current disclosure facilitates production of an embedded ultra low-cost micropump suitable for disposable use. The pump is fabricated with traditional fabrication techniques, producing reliable pumps as small as 15 mm×9 mm×10 mm including the valves, the actuators, the coils and the external body of the pump. The embedded electronics and electromagnetic coils have been optimized to minimize power consumption, thereby enabling battery powered operation. The pump also has an embedded sensor and closed-loop controller, enabling accurate flow rate control, while maintaining a negligible cost. The obtained flow rates exceeded 170 mL/min.

The following characteristics can be selected from and/or combined to facilitate producing a micropump which is sufficiently inexpensive to manufacture that it may be considered disposable. First, the parts are preferably manufactured using standard fabrication methods, avoiding expensive microfabrication techniques like photolithography. Second, it is preferred to use inexpensive materials wherever possible. Third, the pump body and electronic driver are preferably constructed as two separate parts, with the electronic driver being reusable and the pumping mechanism being disposable. Fourth, electrodes and wiring are preferably maintained in a concealed position within the pump body, and therefore non-contact actuation is desired. Fifth, it is preferred to use low driving voltages, thereby permitting the use of less expensive electronic components and direct battery operation. Finally, it is preferred to have a small physical size for embedded applications, employing simpler methods for miniaturization to accommodate future applications.

The need for non-contact actuation along with low driver voltages leads to the selection of electromagnetic actuation. Fortunately, magnetostatic actuation is known to be one of the most efficient methods for micropump actuation systems. See N. Nguyen and S. Wereley, *Fundamentals and Applications of Microfluidics*, ch. 3, Fabrication Techniques for Microfluidics, pp. 55-115 (Artech House), 2002; Y. Fu, H. Du, W. Huang, S. Zhang, and M. Hu, "Tini-based thin films in mems applications: a review," *Sensors and Actuators A*, vol. 112 (23), pp. 395-408, 2004; D. Laser and J. Santiago, "A review of micropumps," *J. Micromech. Microeng.*, vol. 14(6), pp. 35-64, 2004; S. Vishal, S. Garimella, and A. Raman, "Microscale pumping technologies for microchannel cooling systems," *Appl Mech Rev*, vol. 57 (3), pp. 191-221, 2004 and N. Tsai and C. Sue, "Review of mems-based drug delivery and dosing systems," *Sensors and Actuators A*, vol. 134 (2), pp. 555-564, 2007.

The pump operates by electromagnetically driving the membrane magnets in a reciprocating motion within the pump body. As the magnets and consequently the membrane are displaced, a volumetric change occurs within the pumping chambers. This change in volume results in an increased pressure on one side of the membrane and simultaneously a pressure reduction on the other. These pressure fluctuations drive a set of passive check valves installed in each chamber. The check valves are installed so as to be directionally opposed, which results in a net flow. The high pressure side of the membrane forces the corresponding intake valve closed and drives the fluid through the forward biased outlet valve. At the same time, the low pressure side of the membrane forces the corresponding outlet valve closed and draws fluid in through the forward biased inlet valve. When the direction of the membrane is changed, the role of each chamber is reversed. FIGS. 4 and 2, respectively, depict the architectural principles which have been selected for the micropump.

The pumping principle can be explained as follows. The design incorporates a membrane-based electromagnetic actuation system (FIG. 4). Several micropumps already exist which operate based on similar principles. See S. Bohm, W. Olthuis, and P. Bergveld, "A plastic micropump constructed with conventional techniques and materials," *Sensors and Actuators A*, vol. 77-3, pp. 223-228, 1999; D. Laser and J. Santiago, "A review of micropumps," *J. Micromech. Microeng.*, vol. 14(6), pp. 35-64, 2004; and P. Dario, N. Croce, M. Carrozza, and G. Varallo, "A fluid handling system for a chemical microanalyzer," *J. Micromech. Microeng.*, vol. 6, pp. 95-98, 1996. However, none of these have been engineered with a low-cost objective in mind. Nevertheless, even in regards to the general architectural design, this concept is in many ways very different from what is typically encountered, as explained.

Two discrete electromagnetic coils are preferred. This arises from the fact that magnetic forces F and torques Γ between a coil and a magnet are defined as:

$$F = \int_{V_{mag}} M \cdot (\text{grad}(B_{ext})) dV \quad (1)$$

$$\Gamma \int_{V_{mag}} M \times B_{ext} dV \quad (2)$$

where dV is an elementary volume of the total magnet volume $V_{mag}$ M is the magnet's volume magnetization: $M = \mu_0 B_{rem}$ where $B_{rem}$ is the remanent magnetic field inside the material. $B_{ext}$ is the external magnetic field (i.e. due to all possible sources except the magnet. In this case it represents the magnetic field due to the coils.)

The actuation force F is usable only when the position of the magnet (facing the coil) is stabilized by the torque Γ (i.e. when $B_{ext}$ and M have the same direction). Otherwise, the induced torque tends to flip the magnet. With two coils, the magnet will always be attracted by one of the coils and be drawn to it in a stable configuration. The use of two coils also significantly improves the efficiency of actuation.

Second, double chambers are employed. As the pump has two opposing coils, it is possible to use a double chambered architecture with the coils providing symmetric forces instead of the classical single-chamber configuration. This permits the exploitation of both directions of membrane travel, and hence, allows for a nearly continuous output flow.

Third, dual magnets are used. Double chamber designs inherently favor symmetric components. A thin membrane with a single magnet on each side has been selected as a chamber divider and actuation system. This not only provides a symmetric feature but also eases the assembly process by allowing the magnets to be attached to the membrane and held in place by their own magnetic attraction alone. Furthermore, affixing the magnets to the outside of the membrane permits changes to be made to the sizes or shapes of the membrane and magnets independently.

The construction of the preferred embodiment facilitates disposability. As shown in FIG. 2, the system is constructed and arranged to have two, distinct, interworking parts. The reusable part contains the majority of components: the coils, sensor and electronics. The disposable part contains the fluid, valves, membrane and magnets; everything is sealed with the focus on cost reduction. There is no physical contact between the reusable section and the magnets (or the fluid).

By providing a dual-coil arrangement, selection and design of the membrane can be made with a greater range of choice. The dual coils eliminate the need for a strong elastic force in the membrane; this is currently required in many micropump designs or the membrane will not return to the rest position. As a result, an optimal membrane preferably has elastic properties which are negligible compared to the magnetic driving force yet strong enough to prevent deformation from fluid pressure.

Optimal materials which satisfy these requirements are soft elastomers like Latex or PDMS (silicone) (see Table I). For biological applications, Dow Corning Silastic PDMS membrane Q7-4750 or Q7-4840 may be selected, as they have desirable mechanical properties and also have been approved as bio-compatible by the Food and Drug Administration. For non-biological applications, classical latex membranes, as in latex gloves, can be used to further reduce cost.

TABLE I

MATERIAL PROPERTIES OF SELECTED MEMBRANES

| Material | Thickness (mm) | Young's Modulus (MPa) (based on 200% elongation for all Modulus tests) | Elongation (%) |
|---|---|---|---|
| Latex | 0.10 | 0.6 | 400 |
| Q7-4750 | 0.15 | 2.1 | 930 |
| Q7-4840 | 0.13 | 2.6 | 540 |

A benefit of the Silastic-based membrane is the improved lifespan. While latex tends to deteriorate over time (especially after being exposed to fluids), Silastic based membranes have been operated for long periods of time with few signs of degradation. Furthermore, experimental testing showed only a small reduction in performance of the Silastic vs. the latex and a similar frequency response.

As a result of the extensive experimental testing and compatibility issues, the preferred membrane composition for this insulin delivery pump was determined to be Silastic PDMS membrane Q7-4840. However, the initial development was done using Silastic Q7-4750. Comparison of key parameters and data showed that Silastic Q7-4750 and Silastic Q7-4840 are interchangeable in this device. This membrane material was tested for several different thicknesses, with a thickness of 0.006 inches (0.15 mm) performing the best.

Referring now to the preferred magnet selection and arrangement, the following was determined. To obtain the optimum actuation properties, the selected magnets need to possess the greatest possible magnetization. The mass of the magnets is of little importance since the magnetic force is much larger than the inertial effects. In the case of typical rare earth magnets with a remnant flux density $B_{rem}>1.2$ T and a mass density $\rho \approx 7500$ kg·m$^{-3}$, one obtains a magnetic force density of $F_m = \nabla(M \cdot B_{coils}) > 800,000$ N·m$^{-3}$ with a magnetic field gradient $\nabla(B_z) = 0.8$ T·m$^{-1}$ emanating from the coils; the gravitational force is $F_g = g \cdot \rho \approx 75,000$ N·m$^{-3}$. This results in an acceleration of several G's; as a consequence, the velocity of the magnets in a fluid reaches steady-state conditions in just a few tens of microseconds, confirming that the inertia of the magnet may be neglected. Therefore, the optimal choice is the magnet which provides the greatest magnetization possible but at a reasonable price (for disposable use). In a most preferred embodiment, rare earth magnets Neodymium-Iron-Boron Magnets NdFeB, grade N52, with a remanent flux density of 1.5 T and a cost of just a few cents to a dollar each, depending on size, are preferred at the present time. In trial use, NdFeB magnets have been electroplated with a thin nickel coating to resist corrosion. For use in biological applications and to be FDA compatible for use with Silastic membranes, the magnets will preferably be coated with a thin layer of PDMS or similar biocompatible material.

Three types of valves can generally be adapted for use with a pump: active valves, nozzle/diffuser valves, and check valves. To reduce cost and energy consumption, check valves are preferred. However, there were extensive drawbacks with the existing check valves and hence none were deemed optimal for use with the micropump.

For example, commercial check valves, such as vacuum valves used in the automotive industry, are bulky and cost several dollars. As a result, they cannot be used in the context of ultra low-cost micropumps.

Most of the custom check valves which have been fabricated for micropumps, e.g. as in H. Li, D. Roberts, and et al., "A high frequency high flow rate piezoelectrically driven MEMS micropump," in *Proceedings IEEE Solid State Sensors and Actuators Workshop*, Hilton Head, S.C., June 2000; K. Junwu, Y. Zhigang, P. Taijiang, C. Guangming, and W. Boda, "Design and test of a high-performance piezoelectric micropump for drug delivery," *Sensors and Actuators A*, vol. 121, pp. 156-161, 2005; and H. Ma, B. Hou, H. Wu, C. Lin, J. Gao, and M. Kou, "Development and application of a diaphragm micro-pump with piezoelectric device," *Microsyst Technol*, vol. 14, pp. 1001-1007, 2008, are used with piezoelectric actuators. Unfortunately, the opening pressure is too high to be compatible with reduced-force actuation systems like electromagnetic actuators.

The instant disclosure provides a custom flow assembly having very low cost, reduced dimensions allowing direct integration within the pump body, and a very small opening pressure to ensure compatibility with reduced force actuators, as explained in more detail below.

In a preferred embodiment of a micropump, sensing is preferably accomplished as follows. Implementing closed-loop control is often adapted only for sophisticated and expensive systems, in part because of the traditionally high cost of sensors and associated electronic systems. In the preferred embodiment of a micropump, however, the ability to measure and control the real-time position of the magnet is desired. Fortunately, modern advances in electronic manufacturing techniques permit the production of economical sensors and electronics which actually allow for a reduction in overall cost.

For medical applications of the pump, e.g. embedded drug delivery systems, precise fluidic dosing is desired. This is possible in an open-loop configuration only if the system has highly reproducible characteristics during its use and throughout its lifetime. Systems of this nature are frequently very costly to design and fabricate. It has been found that the performance of these pumps depends on the tension and age of the membrane, the position of the magnets, changes in tubing dimensions, the state of the check valves, the temperature of the coils, the power left in the battery, etc.

The use of closed-loop control eliminates the need to keep these parameters stable and enables great reductions in cost for the disposable portion of the pump. However, this is only true provided the costly sensing and control components are located in the reusable portion of the pump.

To address this condition, a contactless sensing system is provided. A preferred solution is to measure the magnetic field which is emanated by the permanent magnets, the magnitude of which is dependent on their position. An additional benefit of closed-loop control is that it prevents collisions between the magnets and chamber walls, which eliminates damage and reduces noise.

In a preferred embodiment of a micropump, electronics are provided as follows. The primary purpose of the pump electronics is to supply power, recondition the sensor signals, and control the pump at a compact and fully embeddable scale. The electronics are contained within the reusable portion of the pump. In a preferred arrangement, the electronic components are inexpensive, provide high current delivery capabilities (up to 400 mA continuous), consume relatively little energy and have small size (e.g. substantially smaller than the pump body, as described).

For this application, small-outline surface-mount components provide a desired technology. In a preferred arrangement, the circuit can have as few as three IC components: a voltage regulator, an H-bridge, and a microcontroller.

The following is a more specific description of the design criteria employed in the specific embodiment of a micropump, of which the disclosed, preferred embodiment is a part.

As pump dimensions are reduced, the forward pressure drop associated with passive valves becomes more significant. In many cases this pressure drop may be the dominant factor in determining pump efficiency. Many designs which work well at the macroscopic level fail as the scale is reduced. At these reduced scales, common check valve designs, i.e. those incorporating a spring, can virtually eliminate all forward flow. As a result, valves based on free floating actuators (ball/slide/membrane) are usually utilized.

Of the three actuators, the preferred design was determined to be based on a movable membrane, which provided better overall performance than commercial vacuum valves for smaller overall dimensions. The preferred arrangement consists of three components assembled and bonded into a single unit: an inlet port with an inner flat surface, an outlet port with a flat, recessed surface in which a rosette pattern has been machined, and an elastomer membrane sandwiched in between (see FIG. 6).

The device operation consists of two states, off and on. In the off state, the backpressure acts to sweep the membrane toward the flat surface of the inlet port; this causes the membrane to cover the inlet port hole, preventing any further reverse flow. In the on state, the forward pressure acts to sweep the membrane toward the outlet port, however, the rosette pattern machined into its surface allows the fluid to flow around the membrane and continue through to the outlet port.

The magnetic force created by each coil depends only on its size and current density J, not on the number of turns or the diameter of the wire used in the coil. However, for a given J, the associated electric properties will be affected by the gauge of the wire. Each coil will have the following voltage U, current I and power P:

$$U = \{J\}\rho 2\pi\{r\}\frac{S_{coil}}{S_{spire}} \quad (3)$$

$$I = \frac{\{J\}S_{spire}}{\alpha} \quad (4)$$

$$P = \frac{\{J^2\}\rho 2\pi\{r\}S_{coil}}{\alpha} \quad (5)$$

where $\{J\}$ is the average current density inside the coil (taking into account the air and insulative components); p is the volumic resistivity of copper; $\{r\}$ is the average radius of the spires of the coil; $S_{coil}$ is the total cross-sectional area of the coil and $S_{spire}$ is the copper surface of each spire. $\alpha$ is the proportion of the coil cross section occupied by the copper: for a coil in the most compact arrangement, the wires occupy $\pi/(2\sqrt{3})$ of the cross-section; taking into account the insulative layer thickness yields $\alpha=(0.9\pi)/(2\sqrt{3})$.

P does not depend on $S_{spire}$; consequently the energetic efficiency of the actuator does not depend on the wire thickness. Its only effect is on U and I levels. A preferred maximum U is 9V for battery powered operation and a preferred maximum I is 200 mA. Thus, the dimensions of the coil become: inner radius: 2 mm; external radius: 9.5 mm; thickness: 2 mm, which yields: $<J_{max}>=1.25*10^7$ A.m.$^{-2}$; $S_{spire}=1.3*10^8$ m$^2$; and wire diameter t=0.135 mm (which corresponds to a 36-37 gauge wire).

For efficient operation and disposable use, the pump body is preferably inexpensive to produce, non-magnetic, incorporates oversized (low resistance) fluid channels, and minimizes the gap between the actuator magnets and driver coils. Furthermore, to maintain a physical size in compliance with typical micropump scales, the pump body should allow for the direct incorporation of check valves. See FIG. 1. The clamshell preferably permanently houses the electromagnetic coils and feedback sensor while also facilitates receipt of the insertable pump body.

Conversion of the current pump to full insulin compatibility required the appropriate selection of materials. In a preferred embodiment, the pump body material was selected to be a medical grade transparent Polypropylene Homopolymer. This material is commonly used within the pharmaceutical and medical industries. Because of the suitable melt flow rate and melt volume flow rate this material is also popular in the injection molding industry. Having a relatively narrow molecular weight distribution makes it particularly suitable for distortion-free molding. Medical grade transparent polypropylene Homopolymer is also used to manufacture barrels for insulin syringes. This material was used in the prototyping of the pumps for testing purposes.

The pump membrane is produced using bio-compatible PDMS, for example Dow Corning Silastic Q7-4840. This is an elastomer that can be casted to the desired geometry. In a preferred embodiment, the membrane can serve two purposes: it can act as a diaphragm and also act as a sealant in between the two halves of the pump body, similar to an O-ring seal. This would simplify the design and reduces the number of parts required.

The pre-stressed valve membranes are now produced using bio-compatible PDMS, for example Dow Corning Silastic Q7-4840. They are formed to an arc-shaped cross-section to ensure proper sealing. Advantages of this geometry are explained below.

The pre-stressed membranes which have been developed to improve upon the flat plate free floating valve membranes offer a number of distinctive advantages. First; they provide enhanced sealing. With a thin and flexible portion of the membrane already pre-stressed against the inlet port and a dome shape designed to catch reverse fluid flow, the new pre-stressed membranes offer exceptional sealing even under very low operating pressures.

Next, they offer improved frequency response. Because the membrane is pre-stressed, it is biased to return to a closed/sealed position. This provides very rapid closure times in the presence of any reverse bias conditions. As a result, the pre-stressed valves can be operated at much higher frequencies while still maintaining excellent low frequency operation.

Additionally, the pre-stressed membranes provide superior back pressure sustainability. As a result of a reduction in port size and the superior mechanical properties of the Silastic membrane, back pressure sustainability problems have been substantially reduced.

In a preferred arrangement, the sensor provided is an A1301 linear Hall effect sensor manufactured by Allegro Microsystems. The A1301 has a sensitivity of 2.5 mV/Gauss. The control hardware is based on a dsPIC30F3012 microcontroller manufactured by Microchip.

Figure 23:
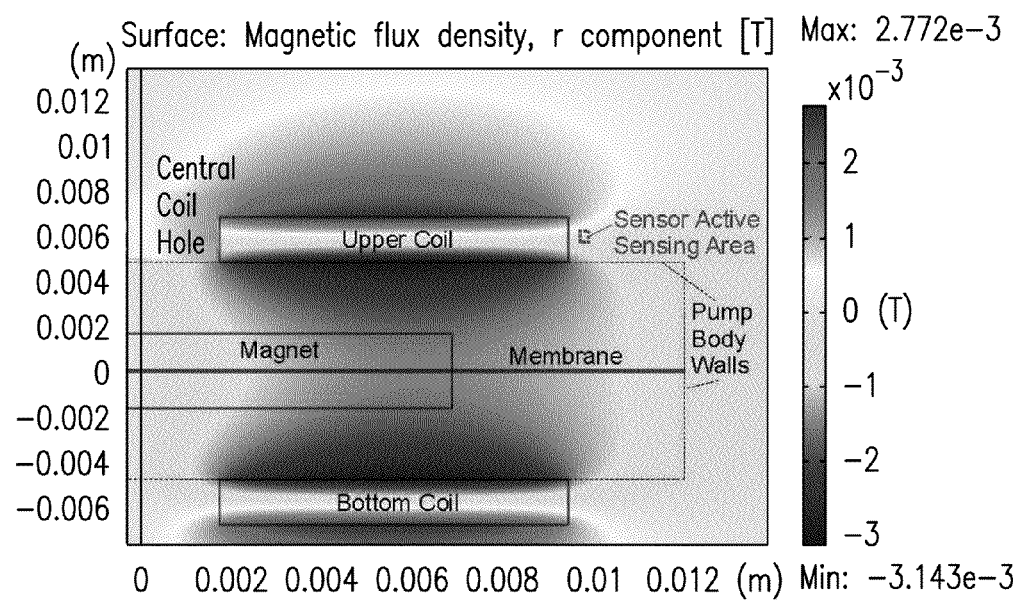
FIG. 23 is a graphical representation of data showing the magnitude of $B_r$ created by the coils of a preferred embodiment of a micropump.
Figure 24:
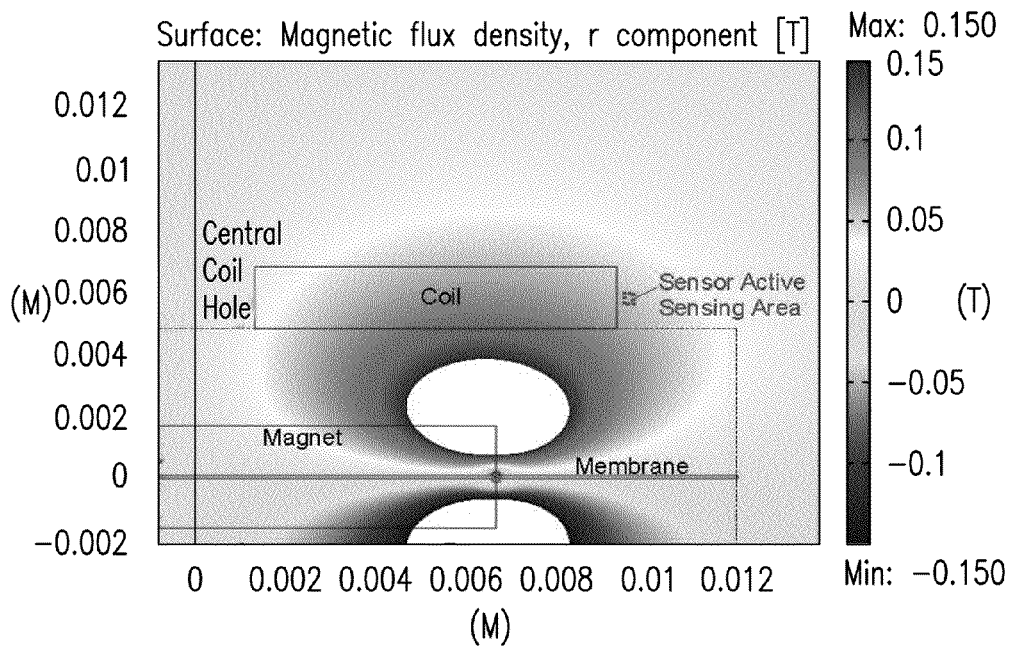
FIG. 24 is a graphical representation of data showing the magnitude of $B_r$ created by the magnets of a preferred embodiment of a micropump.

The Hall sensor is specifically oriented to only be sensitive to the radial component of the magnetic field $B_r$. It is positioned in an area where only the permanent magnet creates a non-negligible value of $B_r$. See FIGS. 23, 24, which show the cartography around the pump depicting the magnitude of $B_r$. FIG. 23 illustrates the magnitude of $B_r$ created by the coils. FIG. 24 depicts the magnitude of $B_r$ created by the magnets. In this particular sensor location, $Br_{coil}$ is negligible and $Br_{magnet}$ is maximized, as compared to any other possible location outside the pump body.

Figure 25:
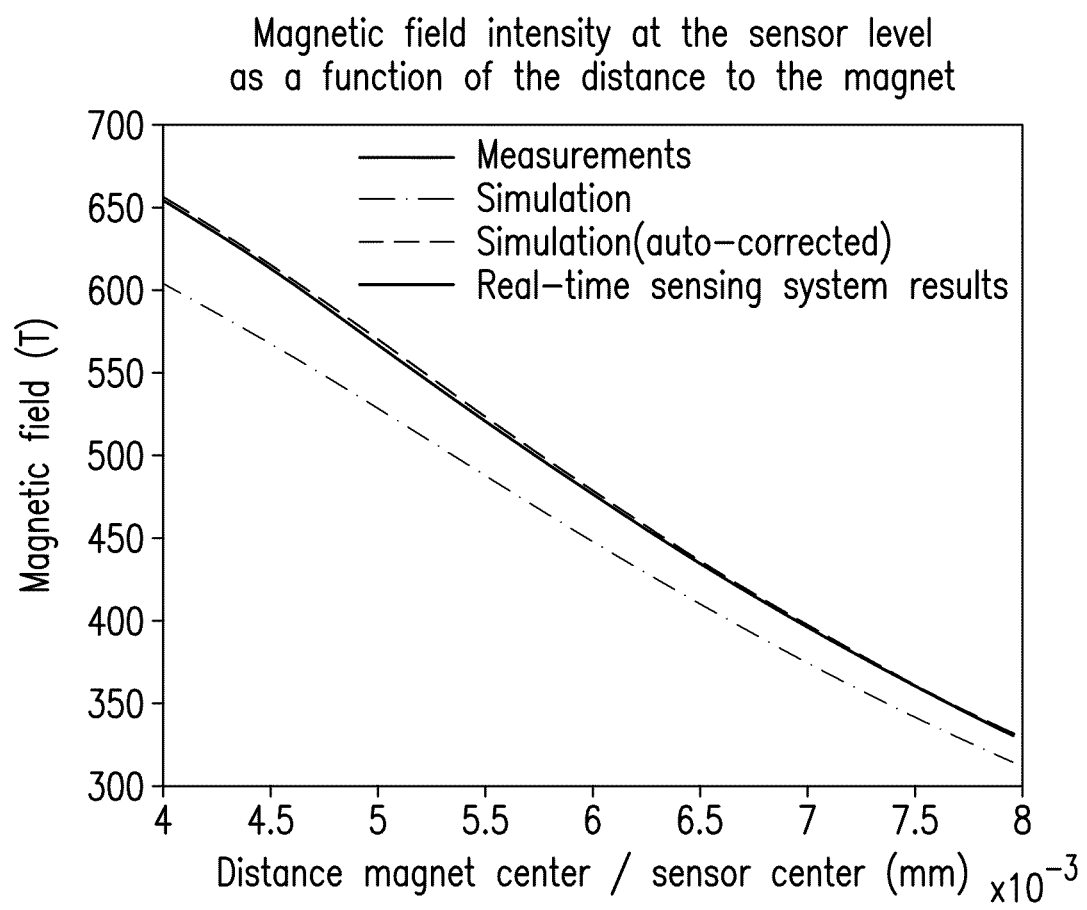
FIG. 25 is a graphical representation of data showing the experimentally measured magnetic field as a function of the position of the magnets, compared with the simulation, the corrected simulation, and the real-time sensing system results of a preferred embodiment of a micropump.

The magnetic field $B_r$ created by the magnet is not linear as a function of its distance to the sensor. For this reason, the signal is compared to values in a lookup table to obtain the position. In the present disclosure, the values are obtained using a model corrected at the pump level during an autocalibration step. Details of the measurement principle are shown in the figure. Results of the position sensing are depicted in FIG. 25, illustrating the experimentally measured magnetic field as a function of the position of the magnets, compared with the simulation, the corrected simulation, and the real-time sensing system results.

Figure 27:
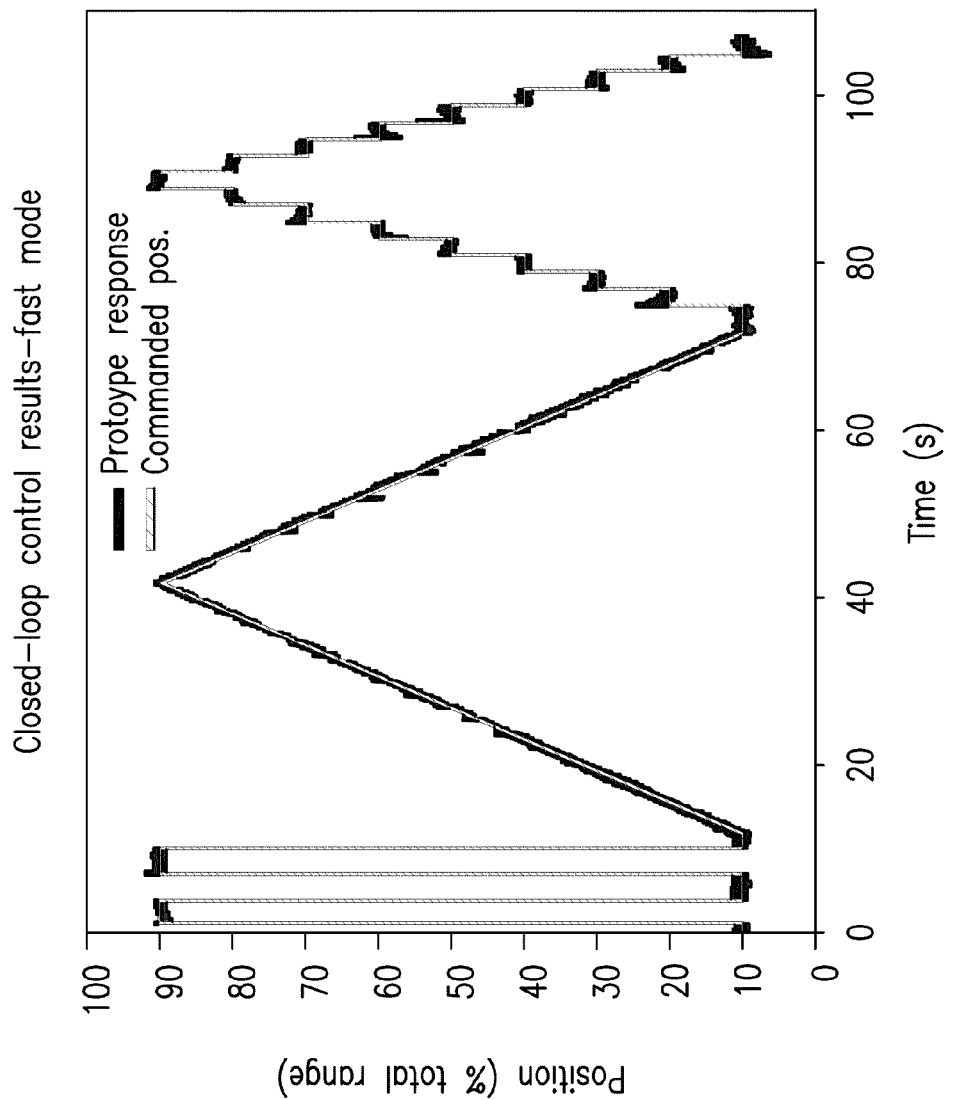
FIG. 27 is a graphical representation of data showing the results of the control strategy depicted in FIG. 26.

Control is accomplished through the implementation of a modified PID controller. The modification mainly consists of restricting the change in setpoint rate to avoid oscillations which would otherwise result from the tilting of the magnet. This method is effective at removing the oscillations because the tilting of the magnet is mainly caused by the quick inversion of the surrounding magnetic field. FIG. 26 illustrates a flow chart depicting the principle of control; results of this control strategy are depicted in FIG. 27, showing controller performance evaluated for a variety of classical setpoint progressions.

To the extent possible, micropump components were fabricated using standard machining techniques and equipment. This provides lower development costs and, ultimately, low mass production costs. This is especially desirable with respect to the disposable portion of the pump, which is ideally produced with simple, inexpensive, and rapid fabrication techniques to maintain low costs whenever possible.

The pump body and clamshell are of a unique design and therefore are custom fabricated. Preferably, they can be made from acrylic plastic, to increase the flexibility of production. In industry, there are two standard methods which can be used for their fabrication: (a) using traditional machine fabrication tools, such as a Computer Numerical Controlled (CNC) mill; and (b) plastic injection molding.

In making prototypes of a preferred embodiment, the pumps were produced with a CNC mill. This was desired because, with only a limited number of prototypes, it was desired to maintain flexibility for making changes to the dimensions throughout the manufacturing run. In mass production, however, it is believed that plastic injection molding will yield a less expensive and faster method to produce these parts.

Because the check valves are integrated within the pump body itself, they were fabricated by machining the appropriate recessed membrane housings and rosette channel patterns into the side of the pump body. Similar patterns were then machined into the plastic valve cover. The membranes were then inserted and the plastic valve cover was permanently bonded to the pump body.

The electromagnetic coils were fabricated by winding 37 gauge magnet wire around a brass bobbin; during winding, a binder was continually added to the wire feeding the spool. This resulted in electromagnetic coils with a resistance of about 42 Ohms and an inductance of about 3.8 mH.

Surface-mount printed circuit boards were fabricated using direct resist transfer and hot gas convection reflow of a 63Sn/37Pb SMD solder paste. The resulting printed circuit board has dimensions of about 17 mm width by about 26 mm length. See FIG. 22.

To achieve low-cost manufacture, a preferred arrangement uses the following assembly process. First, the magnets are centered on the membrane and held in place by their own magnetic attraction. Second, the membrane is cut directly from a latex sheet or a Dow Corning Q7-4840 sheet or a Dow Corning Q7-4750 sheet and placed between the two components of the pump body. The two sections of the pump body are then fastened together. This can be accomplished using screws, or an adhesive binder.

Next, the plastic check-valve covers are permanently bonded to the pump body. Then, the coils are glued into the clamshell and the coil supply leads are routed through the body and soldered to the PCB board. Finally, the sensor is glued into its dedicated position within the clamshell and connected to the PCB board.

Once assembled, performance of the micropump has been characterized for both envisaged membranes (Latex and biocompatible PDMS) using open-loop control for a better measurement of the intrinsic properties of the pump. The following characteristics were studied.

Figure 28:
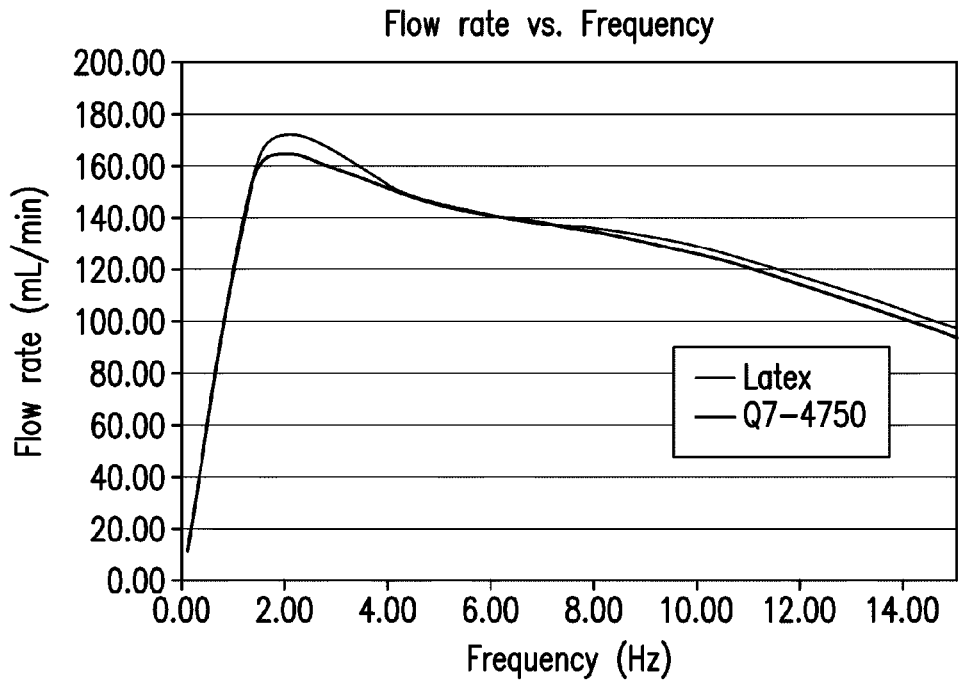
FIG. 28 is a graphical representation of data showing the results of a plot of the flow rate as a function of the excitation frequency for a preferred embodiment of a micropump.

To plot the relationship between flow rate and oscillation frequency, the flow rate as a function of the excitation frequency was measured. See FIG. 28, showing the experimental results of flow rate versus frequency trials for each of the membranes tested (200 mA per coil). The driving signal is a square wave of amplitude I=200 mA sent to each coil. The results shown are the average value of ten measurements.

Figure 29:
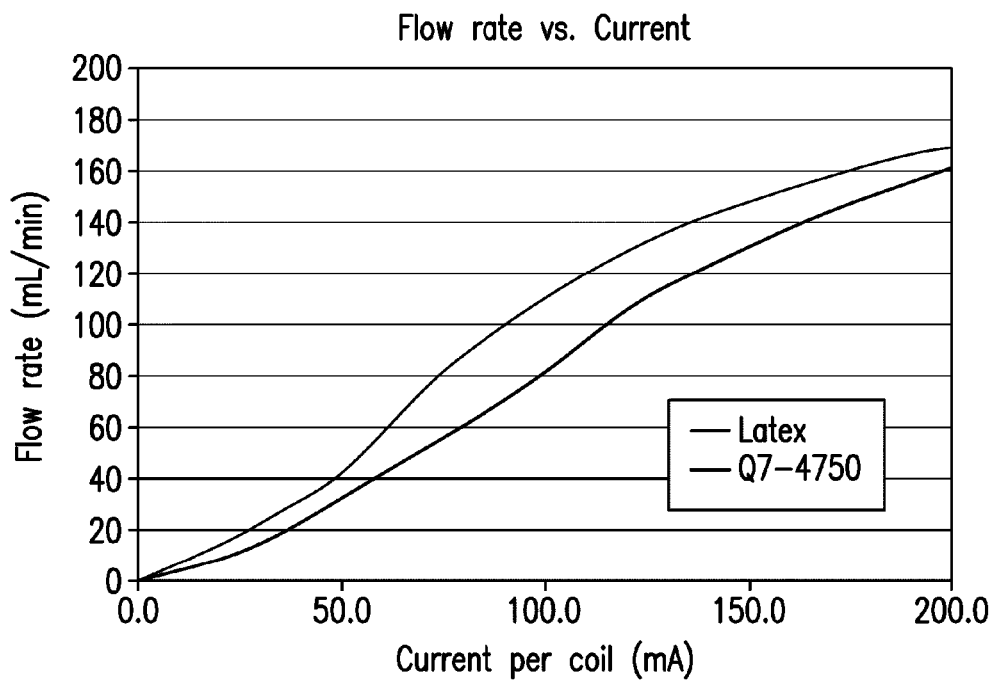
FIG. 29 is a graphical representation of data showing the results of a plot of the volumetric flowrate versus the drive current for a preferred embodiment of a micropump.

To plot the relationship between flow rate and current, the flow rate as a function of the electric current was measured. See FIG. 29, showing the experimentally determined volumetric flowrate versus the drive current. The signal is a square wave of frequency v=2 Hz, the previously determined optimum frequency for square waves. Again, the results shown are the average value of ten measurements.

Figure 30:
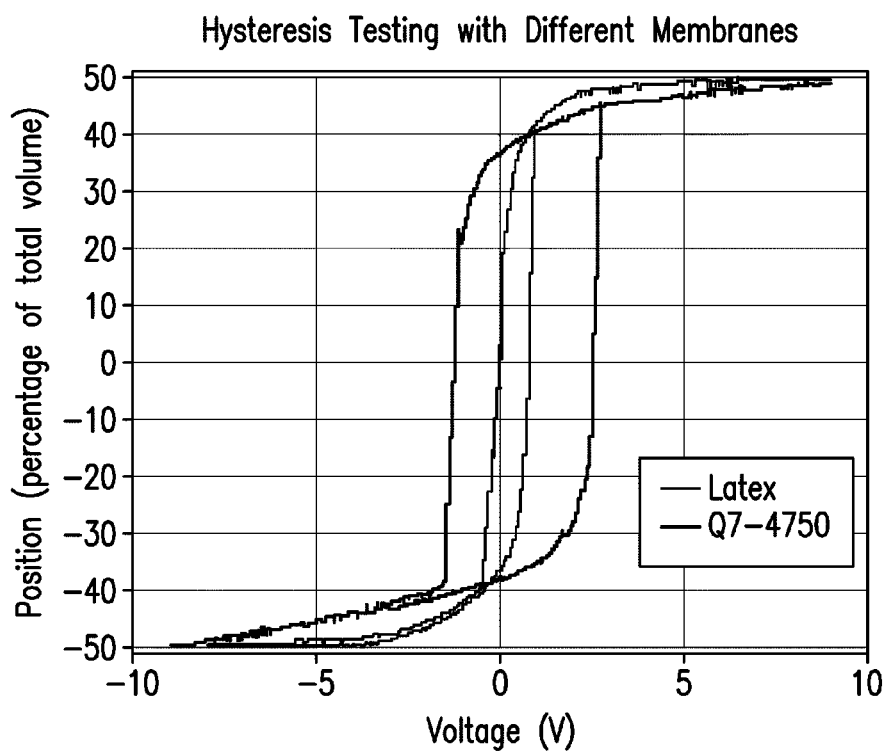
FIG. 30 is a graphical representation of data showing the results of a plot of the hysteresis curves for a preferred embodiment of a micropump.

The hysteresis cycles were measured by utilizing the sensing techniques described above. See FIG. 30, showing the experimentally determined hysteresis curves for each of the membranes tested. Each cycle has a duration of ten minutes. As before, the results shown are the average value of ten measurements.

The fluid pressure was measured as a function of the current. See Table II. The experimental method consists of pumping water into the base of a graduated cylinder, and measuring the maximum height obtained (where 1 cm of water=100 Pa).

TABLE II

FLUID PRESSURE AS A FUNCTION OF DRIVE CURRENT

| Membrane | I = 200 mA Max. Pressure (Pa) | I = 100 mA Max. Pressure (Pa) | I = 50 mA Max. Pressure (Pa) |
|---|---|---|---|
| Latex 0.10 mm | 2550 | 1545 | 834 |
| Q7-4750 0.15 mm | 2501 | 1471 | 686 |

The general principal employed to determine volumetric flow rate involves the pumping of a fluid of known density from a large reservoir to a small sampling beaker. The collected fluid is then weighed on a precise digital scale. The volumetric flow rate is determined from the mass, density, and elapsed time. To minimize the effects of changing fluid levels on pumping performance, a relatively large reservoir was used such that the changes in fluid height throughout the tests were negligible. The fluid collection container was much smaller than the reservoir, facilitating the use of a precision digital scale without invoking overload conditions. After the fluid collection and weighing of each sample, the sampling container was carefully cleaned and dried and then returned for the next collection. The results are summarized in Table III.

The micropump produced flow rates up to 170 mL=min, fluid pressures of 2.5 kPa, and dimensions (including the electronic driver) of 35 mm×25 mm×18 mm.

TABLE III

SUMMARY: PERFORMANCE OF THE LOW-COST MICROPUMP

| Membrane | Max. Flow Rate (mL/min) | Max. Pressure (Pa) | Hysteresis Area (V · mm) | Pump Dimensions (mm × mm × mm) |
|---|---|---|---|---|
| Latex | 172.14 | 2550 | 2.46 | 35 × 25 × 18 |
| Q7-4750 | 164.73 | 2501 | 12.02 | 35 × 25 × 18 |

These results are competitive with other micropumps of similar dimensions. Cf., e.g., M. Zhu, P. Kirby, M. Wacklerle, M. Herz, and M. Richter, "Optimization design of multi-material micropump using finite element method," *Sensors and Actuators A*, vol. 149-1, pp. 130-135, 2009 (flow rate 1.8 mL/min, dimensions 44 mm×17 mm×8 mm—not including electronics); S. Santra, P. Holloway, and C. Batich, "Fabrication and testing of a magnetically actuated micropump," *Sensors and Actuators B*, vol. 87, pp. 358-364, 2002 (flow rate 0.25 mL/min, dimensions 20 mm×16 mm×16 mm—not including electronics); S. Bohm, W. Olthuis, and P. Bergveld, "A plastic micropump constructed with conventional techniques and materials," *Sensors and Actuators A*, vol. 77-3, pp. 223-228, 1999 (flow rate 2.1 mL/min, dimensions 10 mm×10 mm×8 mm—not including electronics); or M. Shen, C. Yamahata, and M. Gijs, "Miniaturized pmma ball-valve micropump with cylindrical electromagnetic actuator," *Microelectronic Engineering*, vol. 85, pp. 1104-1107, 2008 (flow rate 6 mL/min, dimensions 36 mm×25 mm×14.5 mm—not including electronics).

Additional detail regarding development and testing of the micropump membrane is as follows. Results for Latex 0.10 mm, Dow Corning Silastic Q7-4750 0.15 mm, 0.25 mm, 0.38 mm are shown. First, referring now to Tables IV and V, the following flow rate reproducibility data is shown. Table IV shows data for a fixed drive current used for the following frequencies: 0.5 Hz., 1 Hz, and 2 Hz. See Table IV. The specified drive currents are per coil; each measurement was performed 10 times and average data was presented.

TABLE IV

REPRODUCIBILITY DATA FOR A FIXED DRIVE CURRENT

| Trial | Minimum (mL/min) | Average (mL/min) | Maximum (mL/min) | Std. Deviation (σ) |
|---|---|---|---|---|
| 200 mA, 0.5 Hz | 60.8 | 60.25 | 60.54 | 0.17 |
| 200 mA, 1.0 Hz | 118.17 | 118.61 | 119.07 | 0.32 |
| 200 mA, 2.0 Hz | 163.82 | 164.20 | 164.64 | 0.31 |

Table V shows data for fixed frequency over different drive currents. Thus, data for constant frequency for the following drive currents is presented: 50 mA, 100 mA, and 200 mA per coil. See Table V. Again, each measurement was performed 10 times, and average data was presented.

TABLE V

REPRODUCIBILITY DATA FOR A FIXED DRIVE CURRENT

| Trial | Minimum (mL/min) | Average (mL/min) | Maximum (mL/min) | Std. Deviation (σ) |
|---|---|---|---|---|
| 1.0 Hz, 200 mA | 118.17 | 118.61 | 119.07 | 0.32 |
| 1.0 Hz, 100 mA | 98.67 | 99.11 | 99.36 | 0.27 |
| 1.0 Hz, 50 mA | 51.17 | 51.35 | 51.59 | 0.18 |

Figure 31:
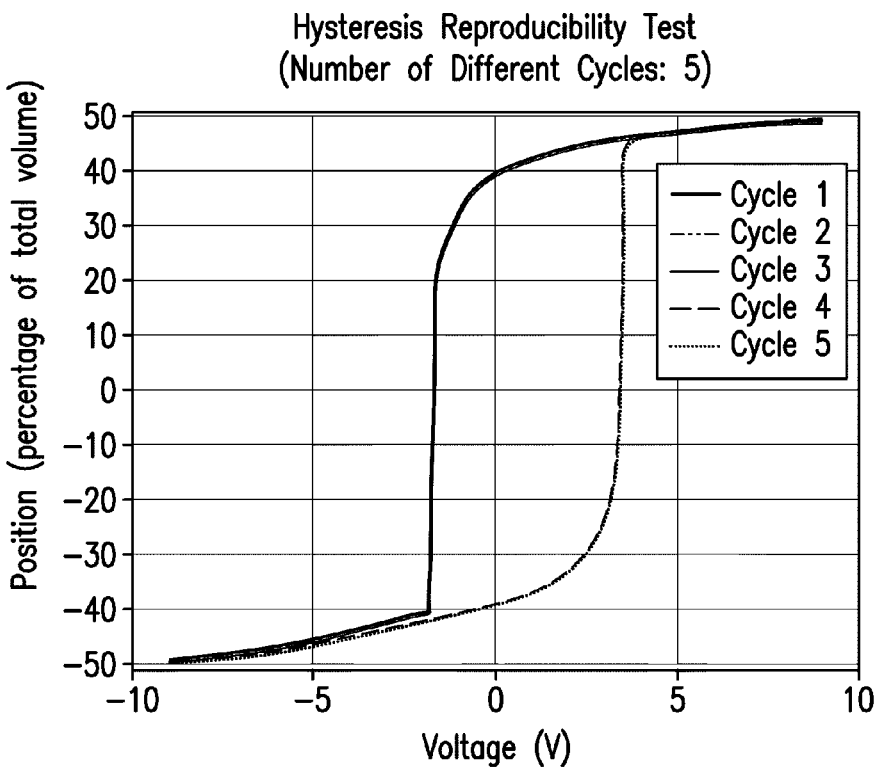
FIG. 31 is a graphical representation of data showing the results of a plot of five consecutive hysteresis measurements performed on the same membrane for a preferred embodiment of a micropump.

Referring now to FIG. 31, data from hysteresis reproducibility tests is presented. The experimental results of five consecutive hysteresis measurements performed on the same membrane are shown. See FIG. 31.

Figure 32:
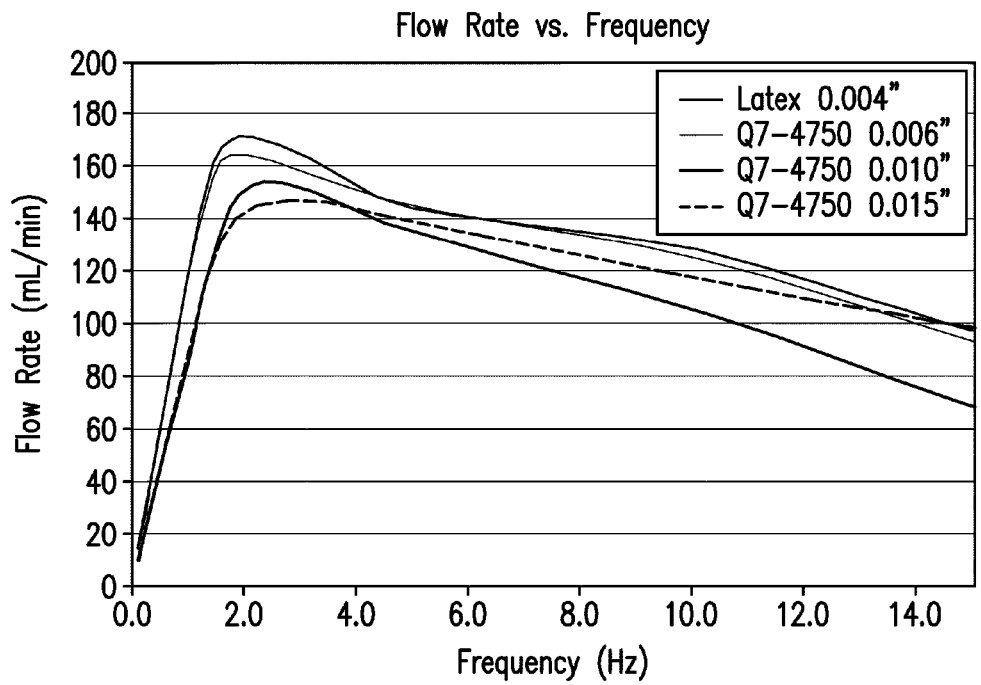
FIG. 32 is a graphical representation of data showing the results of a plot of driving the pump (open-loop) over its entire range of operating frequencies for each of four membranes tested in a preferred embodiment of a micropump.

In FIG. 32, membranes of differing material are tested to show the flowrate as a function of frequency. Results are presented for Latex 0.10 mm (0.004 inches), DowCorning Silastic Q7-4750 0.15 mm (0.006 inches), 0.25 mm (0.010 inches) and 0.38 mm (0.015 inches). As is shown, the pump can be driven over a large range of frequencies. However, there is one particular frequency for which the pump operates best, its resonance frequency This frequency can be easily identified by driving the pump (open-loop) over its entire range of operating frequencies and observing which frequency provides the greatest flow rate. During the tests, the coils were driven at 200 mA (per coil). See FIG. 32, showing the results of driving the pump (open-loop) over its entire range of operating frequencies for each of the four membranes tested.

Figure 33:
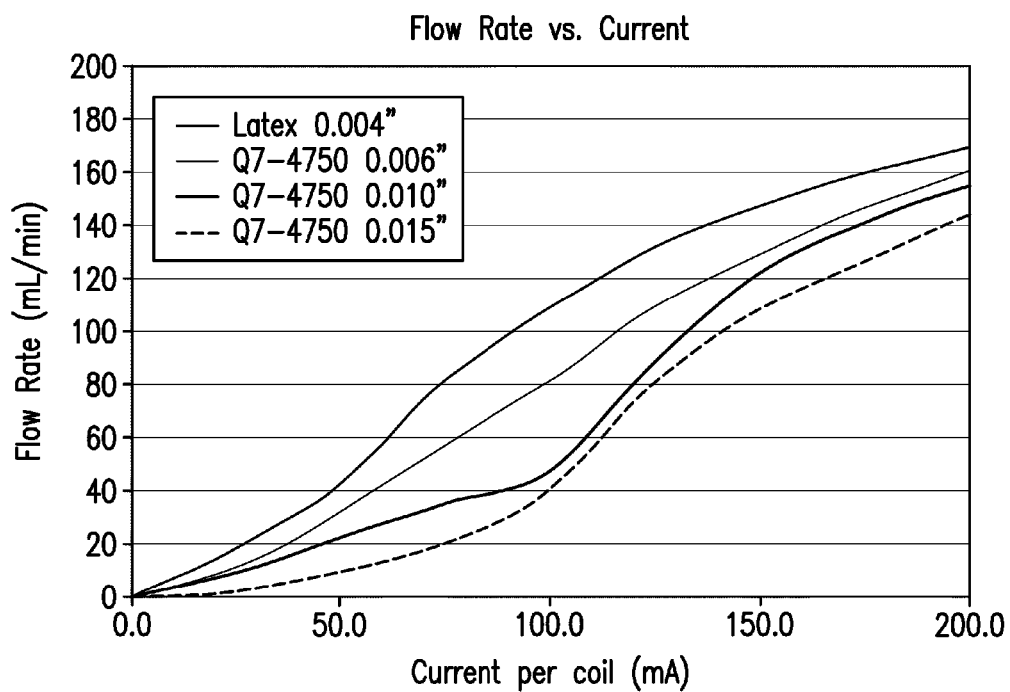
FIG. 33 is a graphical representation of data showing the results of a plot of flowrate as a function of current per coil for membranes of differing material in a preferred embodiment of a micropump.

While it may appear from the data presented in FIG. 32 that all of the membranes tested produce similar flow rates, it is important to note that there is in fact an increased consumption of energy in moving the thicker membranes. To further explore this concept, the volumetric flow rate as a function of drive current was tested. In FIG. 33, membranes of differing material are tested to show the flowrate as a function of current per coil. Results are presented for Latex 0.10 mm (0.004 inches), Dow Corning Silastic Q7-4750 0.15 mm (0.006 inches), 0.25 mm (0.010 inches) and 0.38 mm (0.015 inches).

Figure 34:
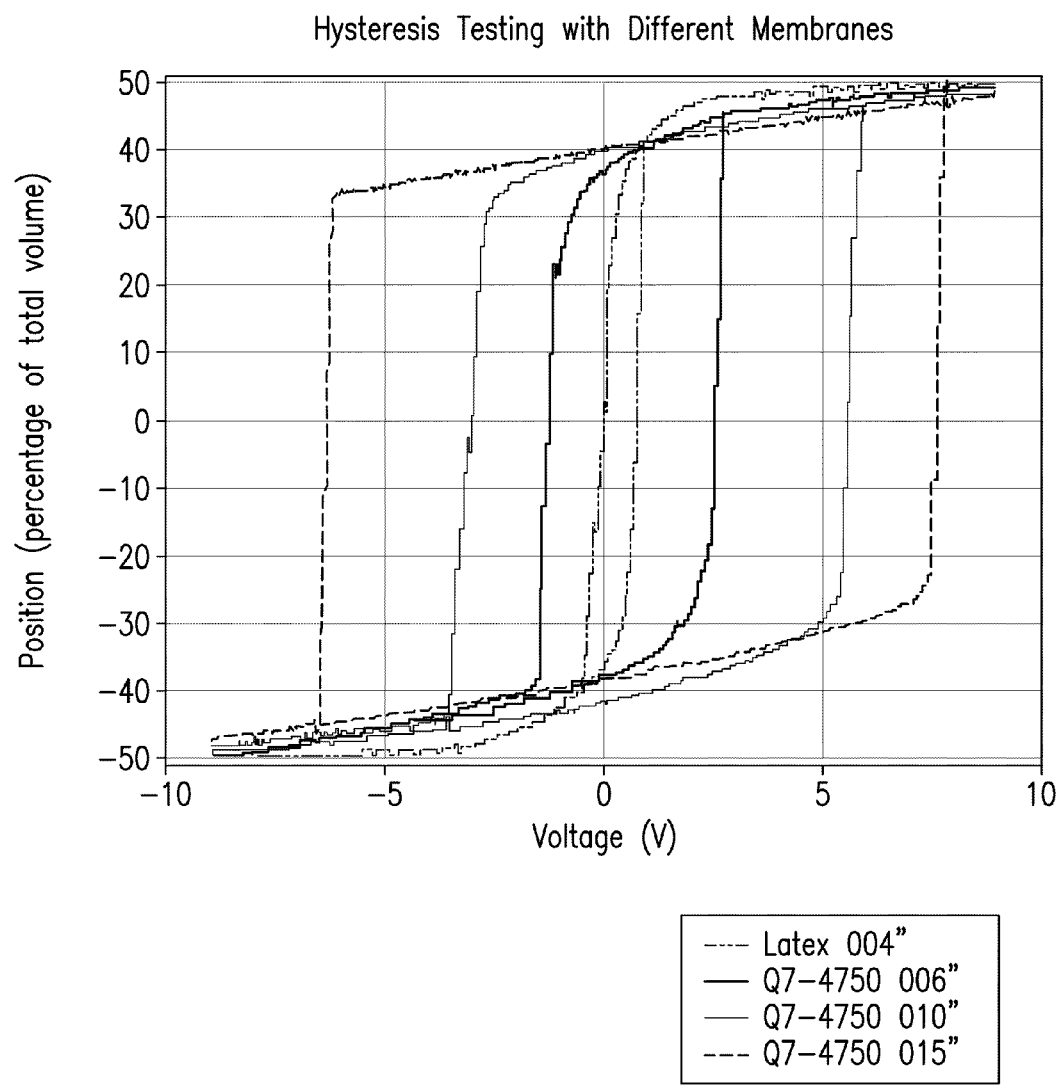
FIG. 34 is a graphical representation of data showing the results of a plot of the voltage used to power the coils versus the position, expressed as percentage of total volume, of the membrane for a preferred embodiment of a micropump.

Further examining the effects of hysteresis, additional testing was performed. Systems that exhibit hysteresis typically exhibit path-dependence. In the case of membrane pumps, path-dependence means that the position depends not only on the driving voltage, but also depends on the direction of travel. In FIG. 34, the experimentally determined hysteresis of each membrane is shown. Again, results are presented for Latex 0.10 mm (0.004 inches), Dow Corning Silastic Q7-4750 0.15 mm (0.006 inches), 0.25 mm (0.010 inches) and 0.38 mm (0.015 inches). FIG. 34 plots the voltage used to power the coils versus the position, expressed as percentage of total volume, of the membrane.

Another performance criterion of the assembly that was tested was the influence of the membrane. As before, results are presented for Latex 0.10 mm (0.004 inches), DowCorning Silastic Q7-4750 0.15 mm (0.006 inches), 0.25 mm (0.010 inches) and 0.38 mm (0.015 inches). The resilience of the membrane to tear failure is recorded by determining the maximum strain reached with respect to the maximum (breaking) elongation.

Figure 35:
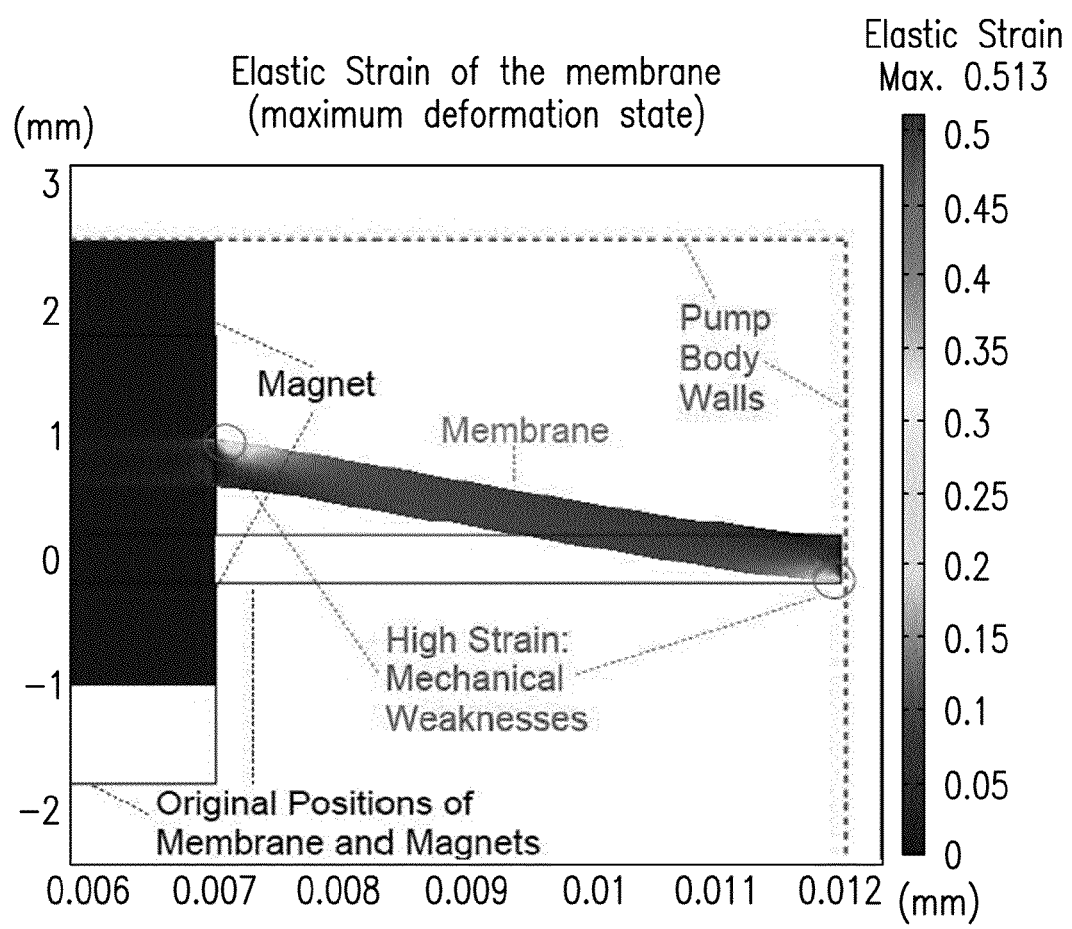
FIG. 35 is a graphical representation of data showing the results of a plot of the maximum strain attained during the deformation of selected membranes for a preferred embodiment of a micropump

As shown in FIG. 35, the distribution of strain inside the membrane while held at the maximum possible deformation (deformed until reaching a wall) is shown. Even at the weakest points, the strain experienced by the membrane is much lower than the break strain. Table VI presents data showing the maximum strain attained during the deformation of the selected membranes.

TABLE VI

MAXIMUM STRAIN ATTAINED DURING THE
DEFORMATION OF THE SELECTED MEMBRANES

| Membrane | Thickness (mm) | Maximum Strain Attained (%) | Failure (%) |
|---|---|---|---|
| Latex | 0.10 | 30 | 400 |
| Q7-4750 0.006" | 0.15 | 32 | 930 |
| Q7-4750 0.010" | 0.25 | 40 | 930 |
| Q7-4750 0.015" | 0.38 | 51 | 930 |

From the data presented in Table VII, the latex membrane provided the best overall performance, providing the greatest possible flow rate and the maximum output fluid pressure, exhibiting the least amount of strain, and exhibiting the best hysteresis characteristics of the membranes tested, the latex gave superior results.

TABLE VII

COMPARISON OF SELECTED PARAMETERS
FOR EACH MEMBRANE TESTED

| Membrane | Maximum Flow Rate (mL/min) | Maximum Pressure (Pa) | Maximum Strain (%) | Hysteresis Area (V · mm) |
|---|---|---|---|---|
| Latex | 172.14 | 2550 | 30 | 2.46 |
| Q7-4750 0.006" | 164.73 | 2501 | 32 | 12.02 |
| Q7-4750 0.010" | 152.45 | 2452 | 40 | 29.33 |
| Q7-4750 0.015" | 147.80 | 2010 | 51 | 45.24 |

Limiting the selection to bio-compatible membranes only, however, the Q7-4750 0.006 membrane performed the best. As seen in Table VIII that the latex membrane provided the best current and power consumption for a given flow rate, but among the bio-compatible membranes the Q7-4750 0.006 membrane performed the best.

TABLE VIII

THE CURRENT AND POWER CONSUMPTION OF
EACH MEMBRANE FOR SELECTED FLOW RATES

| | Current Consumption (mA) | | Power Consumption (W) | |
|---|---|---|---|---|
| Membrane | Flow Rate 70 mL/min | Flow Rate 140 mL/min | Flow Rate 70 mL/min | Flow Rate 140 mL/min |
| Latex | 67.89 | 138.22 | 0.215 | 0.874 |
| Q7-4750 0.006" | 88.25 | 165.24 | 0.361 | 1.246 |
| Q7-4750 0.010" | 113.62 | 173.33 | 0.593 | 1.366 |
| Q7-4750 0.015" | 118.10 | 193.47 | 0.639 | 1.705 |

As thus described, a compact micropump for fluidic/drug delivery applications is disclosed. The micropump can be assembled at low relative cost and provides a disposable pump having a two-component architecture, non-contact actuation, and using standard microfabrication techniques to the extent possible. Closed-loop control of the micropump is achieved by adding inexpensive and accurate sensors to the reusable component without adding the burden of additional cost to the disposable component. Despite its low fabrication cost and small physical size, the micropump performance exceeds design expectations. This is largely due to the pump geometry and dimensions. The micropump this disclosed is small and compact, including the actuators, the pump with fully incorporated check valves, and the electronic driver circuit.

Thus, a method of making a membrane for use with a flow control system is disclosed. First, a mold female body portion having a cylindrical elongate lower portion extending along an axis and having a diameter D, and a centered, concave upper face having substantially the same diameter D and having a radius of curvature R, the upper face being oriented substantially perpendicularly to the axis of the elongate lower portion and extending therefrom, in a substantially vertical, upwardly extending position, is provided. A male mold body portion having a cylindrical elongate upper portion with a lower terminus extending along an axis, the upper portion thereof having a diameter substantially equal to D and a central cylindrical portion having a height H extending from the lower terminus along the axis of the upper portion, the central portion has a diameter of D−G, wherein G is the annular thickness of a spacing gap extending radially outward from the central portion, the male mold body portion further having a centered, convex lower face having a diameter substantially equal to D−G, a radius of curvature substantially equal to R and being oriented substantially perpendicularly to the axis of the elongate upper portion; downwardly to within a predetermined distance Th from the female body portion is provided. A body portion support member having a generally elongated, tubular configuration and further having an inner diameter slightly greater than D, the body portion support member being configured to receive at least a portion of the female body portion and at least a portion of the male body portion, so that the female and male body portions are maintainable along the same axis and the convex face and concave face are positioned in cooperative relation with one another is provided. The female and male body portions are separated from one another and each is lubricated with a lubricant. A sufficient amount of membrane manufacturing material is provided to the concave portion of the lower portion of the female mold body portion. The sleeve is moved down the shaft to cover the joint between the upper and lower half of the mold. The lower mold portion is lowered until it is 0.005" short of its final intended position. Excess membrane manufacturing material, if any, is removed from around the seam of the mold. The upper mold portion is lowered the remaining distance so that the two mold portions are separated by the exact distance desired for the final membrane thickness. The assembly is heated to a desired temperature $T_{heat}$ for a desired time $t_{heat}$. The assembly is allowed to cool for a desired time $t_{cool}$. The membrane is removed.

The described embodiments are to be considered in all respects only as illustrative and not restrictive, and the scope of the invention is, therefore, indicated by the appended claims rather than by the foregoing description. Those of skill in the art will recognize changes, substitutions and other modifications that will nonetheless come within the scope of the invention and range of the claims.

What is claimed is:

1. A method of making a membrane having a reinforcement annulus for use with a flow control system, the method comprising:
providing a mold female body portion having a cylindrical elongate lower portion extending along an axis and having a first diameter, and a centered, concave upper face having a second diameter that is substantially equal to the first diameter and having a first radius of curvature, the upper face being oriented substantially perpendicularly to the axis of the elongate lower portion;

providing a male mold body portion having a cylindrical elongate upper portion with a lower terminus extending along an axis, the upper portion thereof having a third diameter substantially equal to the first diameter and a central cylindrical portion having a height extending from the lower terminus along the axis of the upper portion, the central portion has a fourth diameter and a spacing gap having an annular width extending radially outward from the central portion, wherein the fourth diameter is substantially equal to the first diameter minus the annular width of the spacing gap on each side, the male mold body portion further having a centered, convex lower face having a fifth diameter substantially equal to the fourth diameter and a second radius of curvature substantially equal to the first radius of curvature, and the lower face being oriented substantially perpendicularly to the axis of the elongate upper portion;

moving the male body portion to within a predetermined distance from the female body portion;

providing a body portion support member having a generally elongated, tubular configuration and further having an inner diameter slightly greater than the first diameter, the body portion support member being configured to receive at least a portion of the female body portion and at least a portion of the male body portion, so that the female and male body portions are maintainable along the same axis and the convex face and concave face are positioned in cooperative relation with one another;

separating the female and male body portions from one another and lubricating each with a lubricant;

providing a predetermined amount of membrane manufacturing material to the concave face of the lower portion of the female mold body portion;

covering the area between the male and female mold body portions with the body portion support member;

dropping the male mold body portion until it is 0.005" short of its final intended position;

removing any excess membrane manufacturing material from around the area between the male and female mold body portions;

dropping the male mold body portion the remaining distance so that the two mold portions are separated by the distance desired for the final membrane thickness to cooperatively effect manufacture of the membrane having a reinforcement annulus along a periphery of the membrane, wherein the width of the reinforcement annulus substantially equals the annular width of the spacing gap;

heating the assembly to a predetermined temperature for a first predetermined length of time;

allowing the assembly to cool for a second predetermined length of time; and removing the membrane.

2. The method of making a membrane of claim 1, wherein the first diameter is about 0.25 inches and the annular width is about 0.025 inches.

3. The method of making a membrane of claim 1, wherein the first diameter is about 0.1875 inches and the annular width is about 0.020 inches.

4. The method of making a membrane of claim 1, wherein the premixed membrane manufacturing material is an elastomer.

5. The method of making a membrane of claim 1, wherein the premixed membrane manufacturing material contains silicone.

6. The method of making a membrane of claim 1, wherein the premixed membrane manufacturing material is an enhanced-tear-resistant silicone elastomer.

7. The method of making a membrane of claim 1, wherein the premixed membrane manufacturing material is further prepared by mixing it in a prescribed ratio of a base to a reagent and allowing it to sit for a third predetermined time sufficient to allow the substantial majority of air bubbles to exit the surface.

8. The method of making a membrane of claim 7, wherein the prescribed ratio of base to reagent is about 10:1.

9. The method of making a membrane of claim 8, wherein the third predetermined time is about ten minutes.

10. The method of making a membrane of claim 7, wherein the prescribed ratio of base to reagent is about 1:1.

11. The method of making a membrane of claim 10, wherein the third predetermined time is about ten minutes.

12. The method of making a membrane of claim 7, wherein the third predetermined time is about ten minutes.

13. The method of making a membrane of claim 1, wherein the annular width is about 0.010 inches.

14. The method of making a membrane of claim 1, wherein the annular, width is about 0.015 inches.

15. The method of making a membrane of claim 1, wherein the annular width is about 0.013 inches.

16. The method of making a membrane of claim 1, wherein the lubricant is silicone.

17. The method of making a membrane of claim 1, wherein the predetermined temperature is about 300 F and the first predetermined length of time is about 14 minutes.

18. The method of making a membrane of claim 1, wherein the predetermined temperature is about 302 F, and the first predetermined length of time is about 5 minutes.

19. The method of making a membrane of claim 1, wherein the second predetermined length of time is about two minutes.

20. A method of making a membrane having a reinforcement annulus for use with a flow control system, the method comprising:

providing a mold female body portion having a cylindrical elongate lower portion extending along an axis and having a first diameter equal to about 0.1875 inches, and a centered, concave upper face having a second diameter that is substantially equal to the first diameter and having a first radius of curvature, the upper face being oriented substantially perpendicularly to the axis of the elongate lower portion and extending therefrom, in a substantially vertical, upwardly extending position;

providing a male mold body portion having a cylindrical elongate upper portion with a lower terminus extending along an axis, the upper portion thereof having a third diameter substantially equal to the first diameter and a central cylindrical portion having a height extending from the lower terminus along the axis of the upper portion, the central portion has a fourth diameter and a spacing gap having an annular width of about 0.020 inches extending radially outward from the central portion, wherein the fourth diameter is substantially equal to the first diameter minus the annular width of about 0.020 inches on each side, the male mold body portion further having a centered, convex lower face having a fifth diameter substantially equal to the fourth diameter and a second radius of curvature substantially equal to the first radius of curvature, and the lower face being oriented substantially perpendicularly to the axis of the elongate upper portion;

moving the male body portion downwardly to within a predetermined distance from the female body portion, wherein the predetermined distance is about 0.013 inches;

providing a body portion support member having a generally elongated, tubular configuration and further having an inner diameter slightly greater than the first diameter, the body portion support member being configured to receive at least a portion of the female body portion and at least a portion of the male body portion, so that the female and male body portions are maintainable along the same axis and the convex face and concave face are positioned in cooperative relation with one another;

separating the female and male body portions from one another and lubricating each with a silicone lubricant;

premixing a predetermined amount of membrane manufacturing material in a ratio of 1:1 base to reagent and allowing it to sit for about ten minutes;

providing the predetermined amount of the premixed membrane manufacturing material to the concave face of the lower portion of the female mold body portion;

covering the area between the male and female mold body portions with the body portion support member;

dropping the male mold body portion until it is about 0.005 inches short of its final intended position;

removing any excess membrane manufacturing material from around the area between the male and female mold body portions;

dropping the male mold body portion the remaining distance so that the two mold portions are separated by the exact distance desired for the final membrane thickness and to cooperatively effect manufacture of the membrane having a reinforcement annulus along a periphery of the membrane, wherein the width of the reinforcement annulus substantially equals the annular width of the spacing gap;

heating the assembly to a temperature of about 302 F for about 5 minutes;

allowing the assembly to cool for about two minutes; and removing the membrane.

21. A method of making a membrane having a reinforcement annulus for use with a flow control system, the method comprising:

providing a mold female body portion having a cylindrical elongate lower portion extending along an axis and having a first diameter, and a centered, concave upper face having a second diameter that is substantially equal to the first diameter and having a first radius of curvature, the upper face being oriented substantially perpendicularly to the axis of the elongate lower portion;

providing a male mold body portion having a cylindrical elongate upper portion with a lower terminus extending along an axis, the upper portion thereof having a third diameter substantially equal to the first diameter and a central cylindrical portion having a height extending from the lower terminus along the axis of the upper portion, the central portion has a fourth diameter and a spacing gap having an annular width extending radially outward from the central portion, wherein the fourth diameter is substantially equal to the first diameter minus the annular width of the spacing gap on each side, the male mold body portion further having a centered, convex lower face having a fifth diameter substantially equal to the fourth diameter and a second radius of curvature substantially equal to the first radius of curvature, and the lower face being oriented substantially perpendicularly to the axis of the elongate upper portion;

providing a body portion support member having a generally elongated, tubular configuration and further having an inner diameter slightly greater than the first diameter, the body portion support member being configured to receive at least a portion of the female body portion and at least a portion of the male body portion, so that the female and male body portions are maintainable along the same axis and the convex face and concave face are positioned in cooperative relation with one another;

providing a predetermined amount of membrane manufacturing material to at least one of the concave upper face and the convex lower face;

positioning the body support portion to receive at least a portion of the female body portion and at least a portion of the male body portion; and moving the male and female mold body portions within a predetermined distance from each other to cooperatively effect manufacture of the membrane having a reinforcement annulus along a periphery of the membrane, wherein the width of the reinforcement annulus substantially equals the annular width of the spacing gap, and wherein the predetermined distance between the two mold portions corresponds to a thickness of the membrane.

* * * * *